United States Patent
Luoma et al.

(10) Patent No.: US 9,351,907 B2
(45) Date of Patent: May 31, 2016

(54) PACKAGING SYSTEMS AND METHODS

(75) Inventors: Roy S. Luoma, Fallbrook, CA (US);
Mark C. Doyle, Del Mar, CA (US);
Linda S. Luoma, Fallbrook, CA (US)

(73) Assignee: ID-CON, LLC, Temecula, CA (US)

( * ) Notice: Subject to any disclaimer, the term of this patent is extended or adjusted under 35 U.S.C. 154(b) by 887 days.

(21) Appl. No.: 13/553,796

(22) Filed: Jul. 19, 2012

(65) Prior Publication Data

US 2013/0066463 A1  Mar. 14, 2013

Related U.S. Application Data

(60) Provisional application No. 61/509,509, filed on Jul. 19, 2011.

(51) Int. Cl.
*A61J 7/00* (2006.01)
*A61J 7/04* (2006.01)
*A61J 1/03* (2006.01)
*G06F 19/00* (2011.01)

(52) U.S. Cl.
CPC ........... *A61J 7/0084* (2013.01); *A61J 1/035* (2013.01); *A61J 7/04* (2013.01); *A61J 2200/30* (2013.01); *A61J 2205/30* (2013.01); *A61J 2205/60* (2013.01); *G06F 19/3462* (2013.01)

(58) Field of Classification Search
CPC ..... A61J 7/0445; A61J 7/0436; A61J 7/0427; G07F 17/0092; G06F 19/3462
USPC ........................................................ 700/236
See application file for complete search history.

(56) References Cited

U.S. PATENT DOCUMENTS

| 2,758,710 | A | 8/1956 | Arens |
| 3,311,229 | A | 3/1967 | Troll et al. |
| 3,410,450 | A | 11/1968 | Fortenberry |
| RE29,705 | E | 7/1978 | Compere |
| 4,274,550 | A | 6/1981 | Feldstein |
| 4,305,502 | A | 12/1981 | Gregory et al. |
| 4,307,955 | A | 12/1981 | Cocco et al. |
| 4,340,141 | A | 7/1982 | Fischer |
| 4,537,312 | A | 8/1985 | Intini |
| 4,664,262 | A | 5/1987 | White |

(Continued)

FOREIGN PATENT DOCUMENTS

| JP | 2011-005321 A | 1/2011 |
| WO | 2005/022323 A2 | 3/2005 |

(Continued)

*Primary Examiner* — Patrick Cicchino
(74) *Attorney, Agent, or Firm* — Mark D. Wieczorek; Mayer & Williams PC

(57) ABSTRACT

Systems and methods are provided for delivering single-dose packages sequentially from a substantially continuous strip having a first dispensing end and a second end, e.g., contained within a cassette or other dispenser. The strip includes a cover layer attached to a base layer to define a plurality of blisters therebetween that have one or more medications therein. The blisters are aligned in single file generally along the longitudinal axis between the first and second ends and/or otherwise arranged in single-dose packages adjacent one another, e.g., at least some of the single-dose packages including a plurality of blisters having different types of medications therein. A first single-dose package at the first dispensing end may be separable from a second adjacent single-dose package such that individual single-dose packages may be removed successively from the first dispensing end.

5 Claims, 46 Drawing Sheets

(56) References Cited

U.S. PATENT DOCUMENTS

| | | | |
|---|---|---|---|
| 4,669,613 A | 6/1987 | Collens | |
| 4,733,797 A | 3/1988 | Haber | |
| 4,838,425 A | 6/1989 | O'Brien et al. | |
| 4,884,693 A | 12/1989 | Bruesch | |
| 4,905,866 A | 3/1990 | Bartell et al. | |
| 4,911,291 A | 3/1990 | Iwata et al. | |
| 4,958,736 A | 9/1990 | Urheim | |
| 5,788,974 A | 8/1998 | D'Amico et al. | |
| D414,106 S | 9/1999 | Anderson | |
| D421,900 S | 3/2000 | Eneroth et al. | |
| 6,131,738 A | 10/2000 | DeJonge | |
| 6,244,442 B1 | 6/2001 | Inoue et al. | |
| 6,345,717 B1 | 2/2002 | Flewitt | |
| 6,357,593 B1 | 3/2002 | Bolnick et al. | |
| 6,375,956 B1 | 4/2002 | Hermelin et al. | |
| 6,527,138 B2 | 3/2003 | Pawlo et al. | |
| 6,598,745 B2 | 7/2003 | Bolnick et al. | |
| 6,920,974 B2 | 7/2005 | Reynolds et al. | |
| 6,945,400 B2 | 9/2005 | Bolnick et al. | |
| 7,210,580 B2 | 5/2007 | Elliott | |
| 7,489,594 B2 | 2/2009 | Simon et al. | |
| 7,661,530 B1 | 2/2010 | Hewitt | |
| 7,959,004 B2 | 6/2011 | Tsao | |
| 8,135,497 B2* | 3/2012 | Joslyn | 700/237 |
| 8,161,968 B2* | 4/2012 | Augustyn et al. | 128/203.15 |
| 8,511,304 B2* | 8/2013 | Anderson et al. | 128/203.25 |
| 8,989,896 B2* | 3/2015 | Brown | 700/242 |
| 2002/0153278 A1 | 10/2002 | Pirro et al. | |
| 2002/0162768 A1 | 11/2002 | Bolnick | |
| 2003/0111535 A1 | 6/2003 | Sacchetti et al. | |
| 2003/0168376 A1 | 9/2003 | Taneja et al. | |
| 2003/0200726 A1 | 10/2003 | Rast | |
| 2004/0011693 A1 | 1/2004 | Prenger et al. | |
| 2004/0026293 A1 | 2/2004 | Hughes | |
| 2004/0040881 A1 | 3/2004 | Grosskipf | |
| 2004/0117062 A1* | 6/2004 | Bonney et al. | 700/237 |
| 2004/0158350 A1 | 8/2004 | Ostergaard et al. | |
| 2004/0178112 A1 | 9/2004 | Snyder | |
| 2004/0188312 A1 | 9/2004 | Stepowany | |
| 2004/0188314 A1 | 9/2004 | Rock et al. | |
| 2005/0011804 A1 | 1/2005 | Zanden et al. | |
| 2005/0061825 A1 | 3/2005 | Willoughby | |
| 2005/0087472 A1 | 4/2005 | Elliott | |
| 2005/0145532 A1 | 7/2005 | Kancsar et al. | |
| 2005/0150897 A1 | 7/2005 | Fabricius et al. | |
| 2005/0154491 A1* | 7/2005 | Anderson et al. | 700/236 |
| 2006/0042988 A1 | 3/2006 | Hjalmarsson | |
| 2006/0065670 A1 | 3/2006 | Doublet et al. | |
| 2006/0283749 A1 | 12/2006 | Wolfe et al. | |
| 2006/0289328 A1 | 12/2006 | Hession | |
| 2007/0007162 A1 | 1/2007 | Buller | |
| 2007/0039851 A1 | 2/2007 | Rasanen et al. | |
| 2007/0056876 A1 | 3/2007 | Jones | |
| 2007/0080090 A1 | 4/2007 | Gherdan et al. | |
| 2007/0084746 A1 | 4/2007 | Udo et al. | |
| 2007/0084747 A1 | 4/2007 | Gherdan et al. | |
| 2007/0095715 A1 | 5/2007 | Simon et al. | |
| 2007/0151893 A1 | 7/2007 | Barndt et al. | |
| 2007/0151894 A1 | 7/2007 | Gherdan, Jr. et al. | |
| 2007/0221534 A1 | 9/2007 | Initini | |
| 2007/0235367 A1 | 10/2007 | Initini | |
| 2007/0235369 A1 | 10/2007 | Perell | |
| 2007/0241552 A1 | 10/2007 | Watson et al. | |
| 2007/0289258 A1 | 12/2007 | Jung et al. | |
| 2007/0289893 A1 | 12/2007 | Williams, Jr. | |
| 2008/0035520 A1 | 2/2008 | Caracciolo et al. | |
| 2008/0047230 A1 | 2/2008 | Jung et al. | |
| 2008/0110791 A1 | 5/2008 | Specker | |
| 2008/0155941 A1 | 7/2008 | Williams-Hartman | |
| 2008/0230432 A1 | 9/2008 | Bobbett et al. | |
| 2008/0271417 A1 | 11/2008 | Drost et al. | |
| 2008/0289989 A1 | 11/2008 | Kalvelage et al. | |
| 2008/0302695 A1 | 12/2008 | Meeren et al. | |
| 2009/0008285 A1 | 1/2009 | Miller et al. | |
| 2009/0127154 A1 | 5/2009 | Jeannin et al. | |
| 2009/0127155 A1 | 5/2009 | Nottoli et al. | |
| 2009/0134053 A1 | 5/2009 | Jeannin et al. | |
| 2009/0139893 A1 | 6/2009 | McGonagle et al. | |
| 2009/0152155 A1 | 6/2009 | Pasbrig | |
| 2009/0184022 A1 | 7/2009 | Coe et al. | |
| 2009/0188828 A1 | 7/2009 | Strub et al. | |
| 2009/0230013 A1 | 9/2009 | Born et al. | |
| 2009/0242451 A1 | 10/2009 | Kessler | |
| 2009/0277815 A1 | 11/2009 | Kohl | |
| 2009/0283438 A1 | 11/2009 | Bourque | |
| 2009/0283439 A1 | 11/2009 | Barndt et al. | |
| 2009/0301924 A1 | 12/2009 | Rondeau | |
| 2010/0000899 A1 | 1/2010 | Burg et al. | |
| 2010/0044269 A1 | 2/2010 | Arnold et al. | |
| 2010/0065464 A1 | 3/2010 | Elliott | |
| 2010/0089791 A1 | 4/2010 | Rosenbaum et al. | |
| 2010/0089937 A1* | 4/2010 | Luciano et al. | 221/1 |
| 2010/0108559 A1 | 5/2010 | Kohl | |
| 2010/0108677 A1 | 5/2010 | Loftin et al. | |
| 2010/0270324 A1 | 10/2010 | Blum et al. | |
| 2011/0121019 A1* | 5/2011 | Peer et al. | 222/1 |
| 2011/0262589 A1 | 10/2011 | Safarik | |
| 2012/0083666 A1* | 4/2012 | Waugh et al. | 600/300 |
| 2014/0114471 A1* | 4/2014 | Kim | 700/236 |
| 2014/0346184 A1* | 11/2014 | Bae et al. | 221/1 |
| 2015/0148943 A1* | 5/2015 | Sullivan | 700/231 |

FOREIGN PATENT DOCUMENTS

| | | |
|---|---|---|
| WO | 2008/135823 A1 | 11/2008 |
| WO | 2011/023941 A2 | 3/2011 |

* cited by examiner

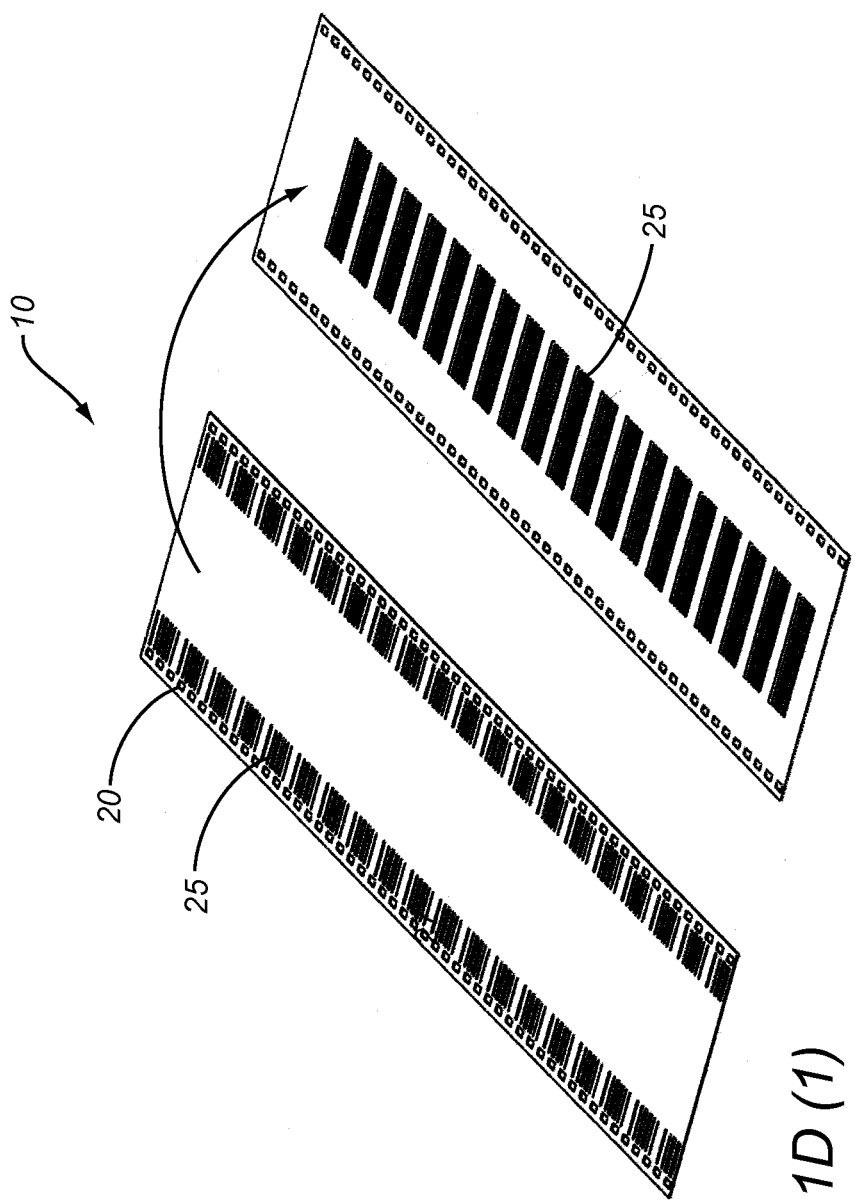
FIG. 1D (2)
FIG. 1D (1)

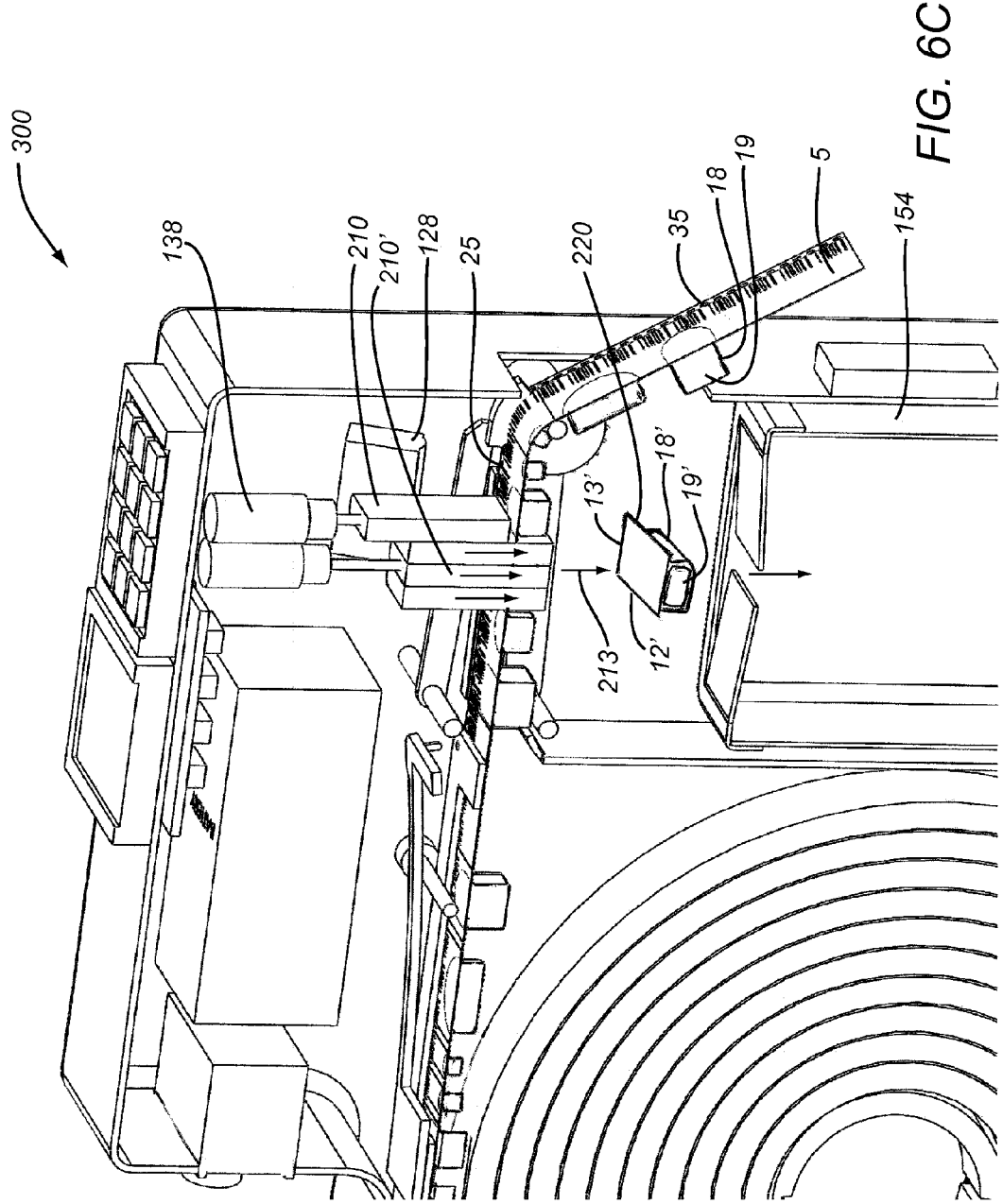

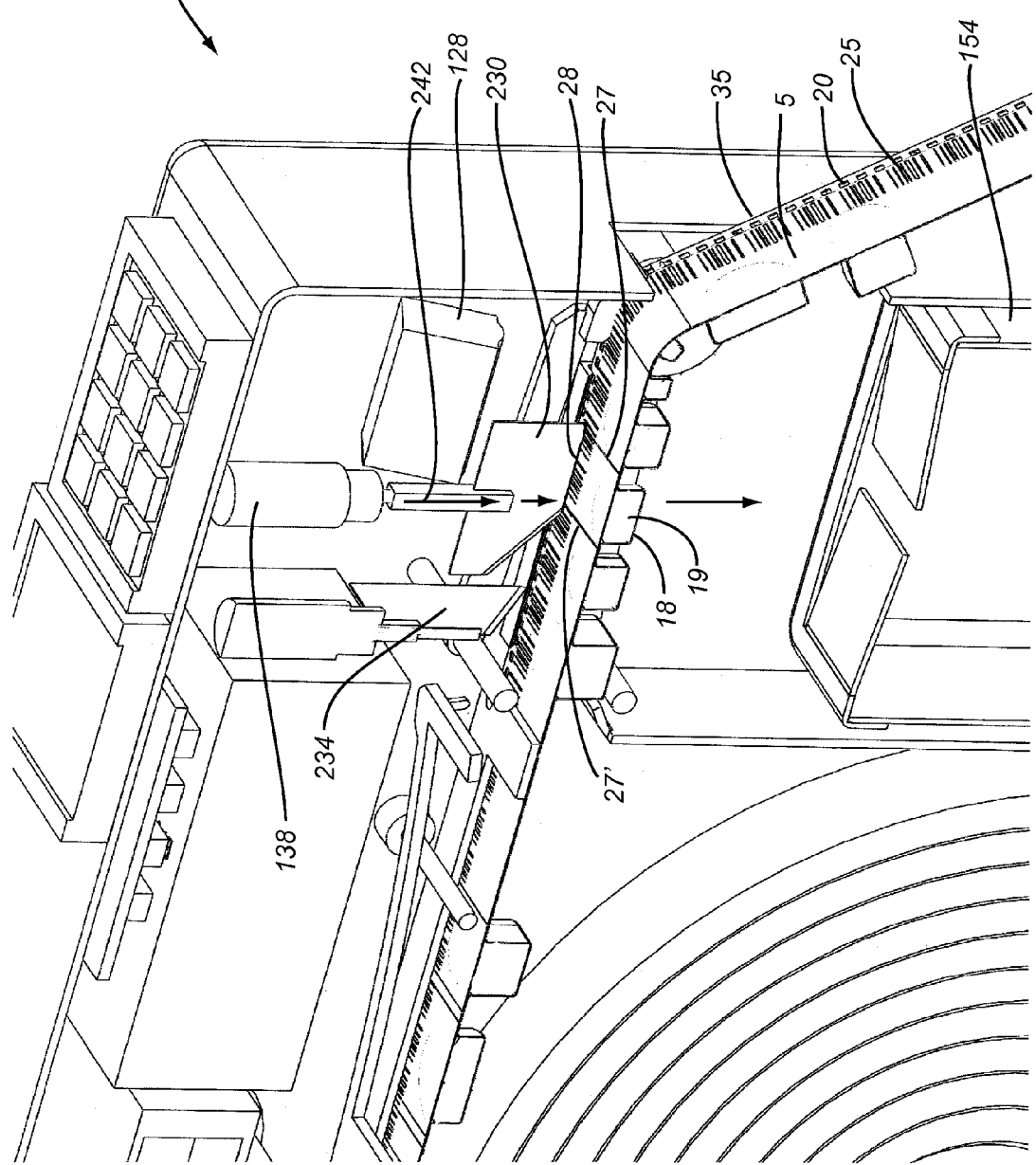

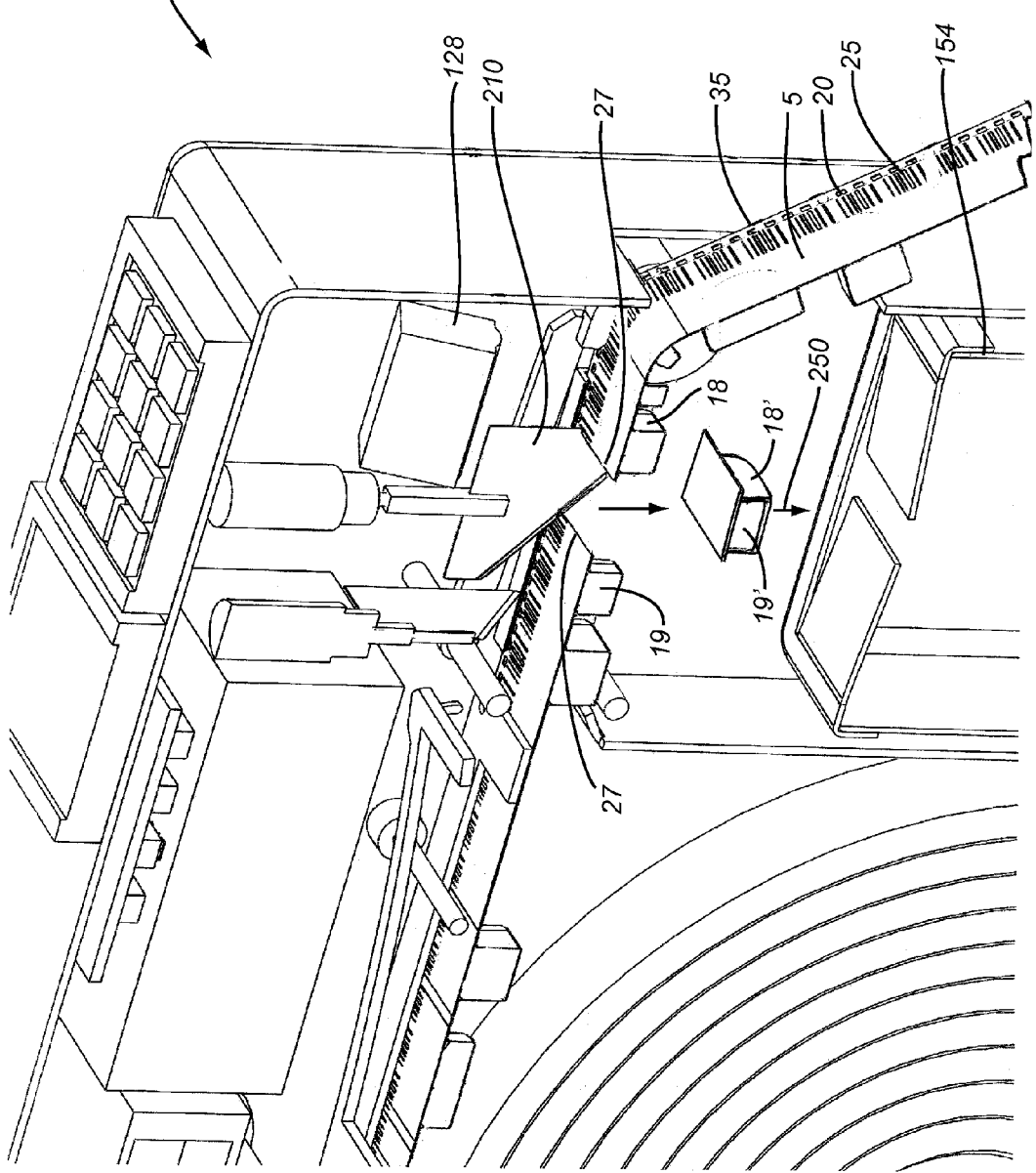

PACKAGING SYSTEMS AND METHODS

RELATED APPLICATION DATA

This application claims benefit of provisional application Ser. No. 61/509,509, filed Jul. 19, 2011, and is also related to application Ser. No. 13/090,209, filed Apr. 19, 2011, and published as U.S. Publication No. 2012/0145585. The entire disclosures of these applications are expressly incorporated by reference herein.

BACKGROUND

Patients undergoing multiple drug regimens, or their caregivers, are required to manage multiple prescriptions and supplements. This includes ensuring that multiple tablets are ingested at predetermined times, in differing arrangements or dose groupings. For example, a patient taking four different medications may have to take all four in the morning, one at mid-day, and three at night. In many cases, the number of prescriptions exceeds ten, and patients or their caregivers may add non-prescription medications, such as aspirin and calcium. Often, different medications are taken at different intervals, such as once a day, three times a day, or four times a day.

Managing so many medications and administration times is often challenging, especially for impaired patients and overworked caregivers. The medications are typically supplied in multiple containers, each containing a single prescription medication, and the user must properly remove the medications from the containers, organize them into a dose grouping (dose), and administer them at the correct time. Errors are frequent, resulting in many health effects, and can result in re-hospitalization and death.

Various organization devices have been suggested to reduce errors, such as pill organization boxes, but these require the user to correctly load the box in order for them to be effective, a time consuming and inexact process. Thus, there is a need for a practical methods for pre-organizing medications to reduce labor and/or errors.

SUMMARY

The present application relates to packaging systems, and to methods for making and using customized packages, e.g., single-dose packages provided together, e.g., in a container, strip, and the like. More particularly, the present application is directed to dispenser apparatus and to systems and methods for dispensing and administering medications, e.g., from a strip of single-dose packages that may be dispensed in a predetermined sequential order.

In one embodiment, various medications intended to be ingested at a given date and time are packaged together in a single easily identifiable and open-able dose package (e.g., a "single-dose package"). In an exemplary embodiment, the dose package may provide the medications disposed in a single-file arrangement, i.e., with a single blister or medication across the width of the package and one or more blisters or medications, e.g., a plurality of blisters, arranged along the length of the package. In another embodiment, the dose package may be part of a continuous coil or strip of detachable sequential dose packages.

In another embodiment, the dose package is separated from the next dose package by a perforation. In another embodiment, the dose package is disposed to peel open to release the medications. In another embodiment, the dose package is labeled with the information required for proper administration by the user and/or dispensing from a dispenser apparatus (e.g., patient name, scheduled or intended administration date of dose, scheduled or intended administration time of dose, medications within respective packages and/or individual blisters, and the like). In another embodiment, the package includes tamper-evidence and childproofing features. In another embodiment, the dose package includes adhesion features to attach at least a portion of the dose package to a surface. In another embodiment, the dose package includes a peel-able cover with a layer of adhesive or one or more other features to attach the cover to a surface, such as a patient's record or chart. In another embodiment, the dose package includes machine-readable information to permit automated dispensing of the dose packages and/or verification of administration. In another embodiment, the dose package includes holes, notches, and other physical features that assist in automated dispensing of the package.

An embodiment of the dose package constructed as a coil of detachable sequential dose packages may be well adapted to be supplied in a box, cassette, or other container. In such an embodiment, the coil is contained within the box or cassette ("cassette") such that a first dispensing end of the coil is accessible and is easily manipulated, which allows the coil to be removed far enough from the cassette to permit the user to remove the next dose package.

In another embodiment, the cassette may include all pertinent patient and medication information. In another embodiment, the cassette may include machine readable information, codes, strips, chips, and features. In another embodiment, the cassette may include a child proofing feature to prevent or resist dose package removal by children. In another embodiment, the cassette may include a drag feature to prevent the end of the coil from easily falling into the cassette. In another embodiment, the cassette may include a view window to permit viewing of the information of the next dose package.

The aforementioned cassette containing a coil of detachable sequential dose packages may be loaded into or otherwise provided within an automated dispensing machine, herein called a dispenser. The dispenser may hold and locate the cassette, dispense one or more desired dose packages at the appropriate time(s), and/or alert the user that a dose package has been dispensed or is ready to be dispensed. In a first embodiment, the dispenser may include a timing device, a drive system for advancing the coil to present the next dose package, and/or an alert system to inform the user that the dose is dispensed or ready to be dispensed.

In a second embodiment, the dispenser may also include a tablet removal system to remove one or more unwanted medications from the dose packages, e.g., by pushing individual blisters out of the dose package before presenting a dose package. In a third embodiment, the dispenser may also include a tablet removal system to remove one or more unwanted medications from the dose packages, e.g., by cutting individual blisters out of affected dose package. In a fourth embodiment, the dispenser may also include a blister marking system to mark blisters containing one or more unwanted medications in the dose packages for subsequent removal of individual tablets from the dose package by the user.

Various embodiments of the dispenser may include one or more of the following features: a bar code reader(s), a magnetic reader, a RFID reader, an optical reader, one or more control circuits or controllers, an alarm, a display screen, an AC power adapter, a battery power source, a door-closed sensor, a door lock, a communication interface (e.g., telephone, Wi-Fi, cable, 3G, etc.), one or more access control features, a security cover, and a childproof-lock disabling feature. In yet another embodiment, the dispenser may automatically inform the patient's caregiver or doctor when a dose package has not been removed from the dispenser and/or has been removed and opened to administer the medications therein to the patient.

In accordance with a first embodiment, an apparatus is provided for administering medications to a patient that includes a strip comprising a first dispensing end, a second end, and a plurality of blisters aligned in single file generally along a longitudinal axis between the first and second ends and arranged in single-dose packages adjacent one another, at least some of the single-dose packages including a plurality of blisters having different types of medications therein, and a housing for receiving the strip therein such that the first dispensing end extends from an outlet of the housing.

In addition, the apparatus may include a drive mechanism within the housing and coupled to the strip for selectively advancing the strip to dispense single-dose packages sequentially from the outlet. A reader may be provided adjacent the outlet for reading one or more labels on each of the single-dose packages, and a controller may be coupled to the reader and the drive mechanism for analyzing a label on a first single-dose package adjacent the outlet to determine a scheduled administration time for medications in the first single-dose package and for actuating the drive mechanism to dispense the first single-dose package from the outlet at or about the scheduled administration time.

In accordance with another embodiment, an apparatus is provided for administering medications to a patient that includes a strip including a first dispensing end, a second end, and a plurality of blisters aligned in single file generally along a longitudinal axis between the first and second ends and arranged in single-dose packages adjacent one another, at least some of the single-dose packages including a plurality of blisters having different types of medications therein, and a housing for receiving the strip therein such that the first dispensing end extends from an outlet of the housing.

In addition, the apparatus may include a drive mechanism within the housing and coupled to the strip for selectively advancing the strip to dispense single-dose packages sequentially from the outlet, a reader adjacent the outlet for reading one or more labels on each of the single-dose packages; and a communication interface for communicating with a remote server via a network. A controller is coupled to the reader for acquiring data from a label on a first single-dose package adjacent the outlet, the controller coupled to the communication interface for communicating the data to the remote server via the communication interface and receiving instructions regarding a scheduled administration time for medications in the first single-dose package, the controller coupled to the drive mechanism for actuating the drive mechanism to dispense the first single-dose package from the outlet at or about the scheduled administration time.

In accordance with still another embodiment, a method is provided for administering medications to a patient that includes loading a strip comprising first and second ends into a dispenser such that the first end extends from an outlet of the dispenser, the strip comprising a plurality of blisters aligned in single file generally along a longitudinal axis between the first and second ends and arranged in single-dose packages adjacent one another, at least some of the single-dose packages including a plurality of blisters having different types of medications therein; activating the dispenser whereupon the dispenser analyzes one or more labels on a first single-dose package adjacent the outlet to determine a scheduled administration time for medications in the first single-dose package; and removing the first single-dose package after the first single-dose package is dispensed from the outlet at or about the scheduled administration time.

In accordance with yet another embodiment, a method is provided for administering medications to a patient that includes providing a strip comprising first and second ends housed within a dispenser such that the first end extends from an outlet of the dispenser, the strip comprising a plurality of blisters aligned in single file generally along a longitudinal axis between the first and second ends and arranged in single-dose packages adjacent one another, at least some of the single-dose packages including a plurality of blisters having different types of medications therein; analyzing one or more labels on a first single-dose package adjacent the outlet to determine a scheduled administration time for medications in the first single-dose package; and dispensing the first single-dose package from the outlet at or about the scheduled administration time.

In accordance with still another embodiment, a method is provided for administering medications to a patient that includes providing a strip comprising first and second ends housed within a dispenser such that the first end extends from an outlet of the dispenser, the strip comprising a plurality of blisters aligned in single file generally along a longitudinal axis between the first and second ends and arranged in single-dose packages adjacent one another, at least some of the single-dose packages including a plurality of blisters having different types of medications therein; analyzing one or more labels on a first single-dose package adjacent the outlet to acquire data identifying the first single-dose package; communicating the data to a remote server via a network; receiving instructions from the remote server regarding a scheduled administration time for medications in the first single-dose package; and dispensing the first single-dose package from the outlet at or about the scheduled administration time.

In accordance with yet another embodiment, a system is provided for managing administration of medications to a patient that includes a dispenser comprising a housing and a strip comprising a first dispensing en extending from the housing, a second end, and a plurality of blisters aligned in single file generally along a longitudinal axis between the first and second ends and arranged in single-dose packages adjacent one another, at least some of the single-dose packages including a plurality of blisters having different types of medications therein; and a reader for reading labels on single-dose packages dispensed from the dispenser to confirm administration of medications in the dispensed single-dose packages.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIGS. 1D(1) and 1D(2) are perspective views of outer and inner surfaces of a cover that may be included in a single-dose package, such as that shown in FIG. 1A, including machine-readable labels on the respective surfaces.

FIGS. 6A-6E are perspective views of the dispenser of FIG. 3 with a portion of the outer housing removed to show internal punches, showing a method for removing an unwanted blister from a dose package using the punches before dispensing the dose package from the dispenser.

FIGS. 7A-7G are perspective views and details of an alternative embodiment of a dispenser with a portion of the outer housing removed to show internal cutting elements, showing a method for removing an unwanted blister from a dose package using the cutting elements before dispensing the dose package from the dispenser.

DETAILED DESCRIPTION OF THE EXEMPLARY EMBODIMENTS

Figure 1A:
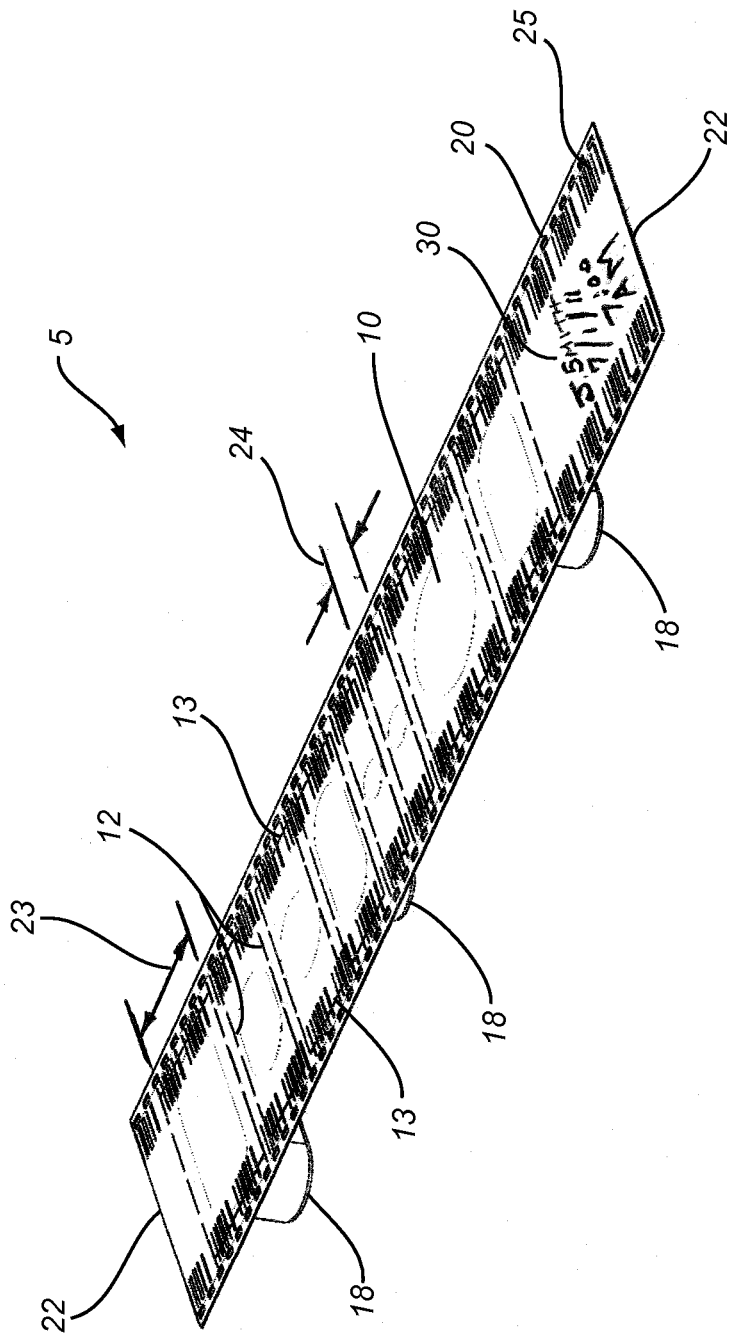
FIG. 1A is a perspective view of a first exemplary embodiment of a single-use package including a cover removably attached to a web or base layer to define a plurality of blisters, the cover including various labels thereon and weakened regions to facilitate separating individual blisters from the rest of the package.

Turning to the drawings, FIG. 1A shows an exemplary embodiment of a dose package 5 that generally includes a cover 10 and a base 15 extending between ends of the package, thereby defining a longitudinal axis for the package (or series of packages, not shown). The cover 10 and base 15 may be formed from substantially continuous lengths of material, e.g., one or more layers of paper, polymer, foil, composite, or other materials, which may be rigid, flexible, clear, opaque, and the like. The base 15 generally includes one or more blisters or cavities 18 that contain tablets, gel caps, or other forms of medication (not shown), hereinafter called "items." The cover 10 is attached to the base 15, e.g., such that the cover 10 may be separated from the base 15 substantially intact as described further below, e.g., using adhesive, welding, and/or other methods. Optionally, the cover 10 may include perforations 20, e.g., between adjacent single-dose packages of a strip of packages (not shown), and one or more machine-readable features 25, e.g., similar to other embodiments herein and in U.S. Publication No. 2012/0145585, the entire disclosure of which is incorporated by reference herein. Similarly, the base 15 may also include perforations 20, e.g., optionally aligned with corresponding perforations in the cover 10. The machine-readable features 25 may include information regarding one or more of the following: patient name, scheduled or intended date of administration of the dose in the package 5, scheduled or intended time of administration of the dose, names and descriptions of items 19, specific locations of items 19, e.g., within each of the blisters 18 of the package 5, scheduled or intended time of administration of the next dose package, etc. The machine-readable features 25 may be aligned with specific blisters 18 in order to aid in removal of unwanted Items 19 and/or identifying contents of each of the blisters 18.

Figure 1B:
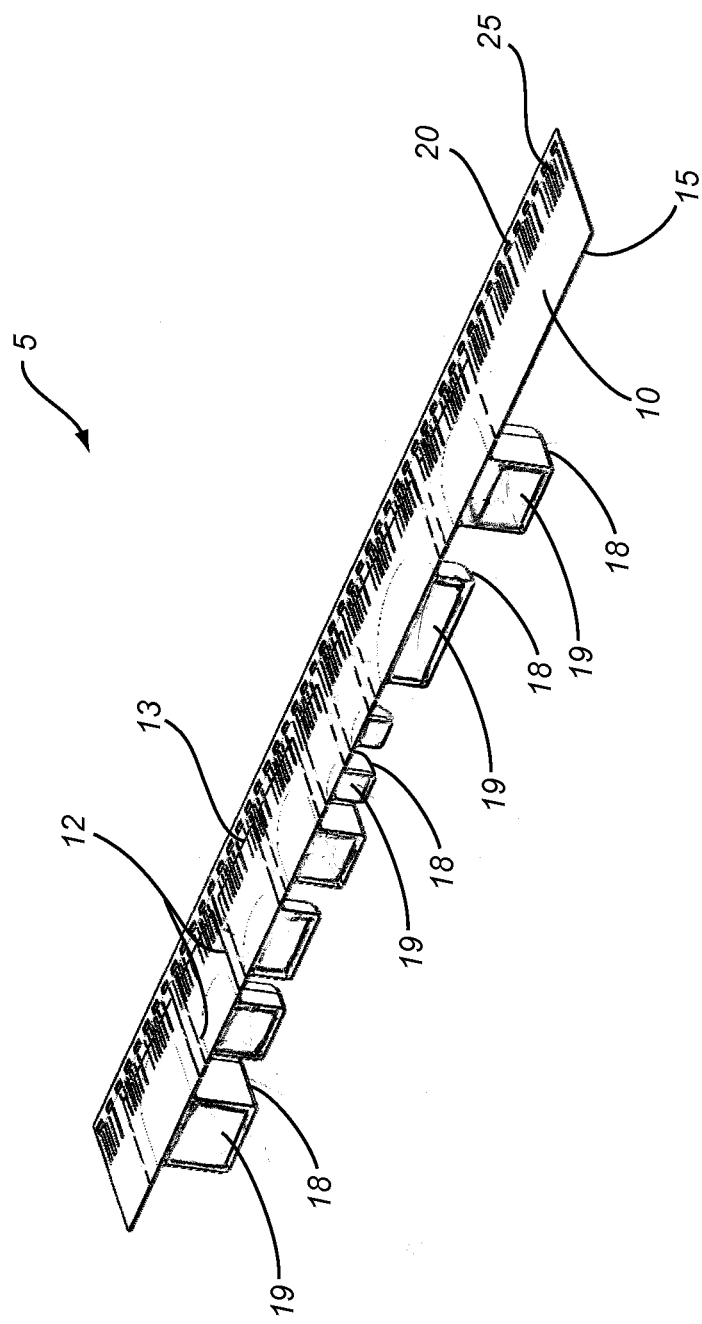
FIG. 1B is a cross-sectional perspective view of the package of FIG. 1A taken along its length, showing blisters defined between the cover and base layer and medications in the blisters.

To administer the dose, a user may peel or otherwise separate the cover 10 from the base 15 to release items 19 from the blisters 18, as described further elsewhere herein and in U.S. Publication No. 2012/0145585. As shown in FIG. 1B, each of the blisters 18 may contain one or more items 19 (for example, a single tablet or other medication), which may be removed and administered to a patient once the cover 10 is separated. As the items 19 may vary in size, the blisters 18 may also vary accordingly in size and/or spacing from one another, e.g., in order to conserve space.

Optionally, as shown in FIG. 1A, each of the blisters 18 may be surrounded by one or more perforations, e.g., including transverse or cross perforations 12 and longitudinal perforations 13, thereby defining a weakened region surrounding each blister 18, e.g., to facilitate removal of unwanted items 19 from the dose package 5 before dispensing and/or administration of the dose. These weakened regions may vary in length, e.g., such that the tabs of material remaining between adjacent weakened regions secure the blisters 18 to the rest of the package 5, and have variable widths to provide greater or lesser resistance to separate the blisters 18 from the rest of the package 5. For example, a longer blister 18 may require a relatively larger longitudinal perforation 13, shown by longitudinal dimension 23, while a smaller blister 18 may only require a relatively shorter longitudinal perforation 13, as shown by longitudinal dimension 24. Thus, the longitudinal perforations 13 may vary according to blister size. Alternatively, the weakened regions may define other shapes, e.g., circular, elliptical, oval, and the like, e.g., surrounding a correspondingly shaped blister (not shown).

Figure 2A:
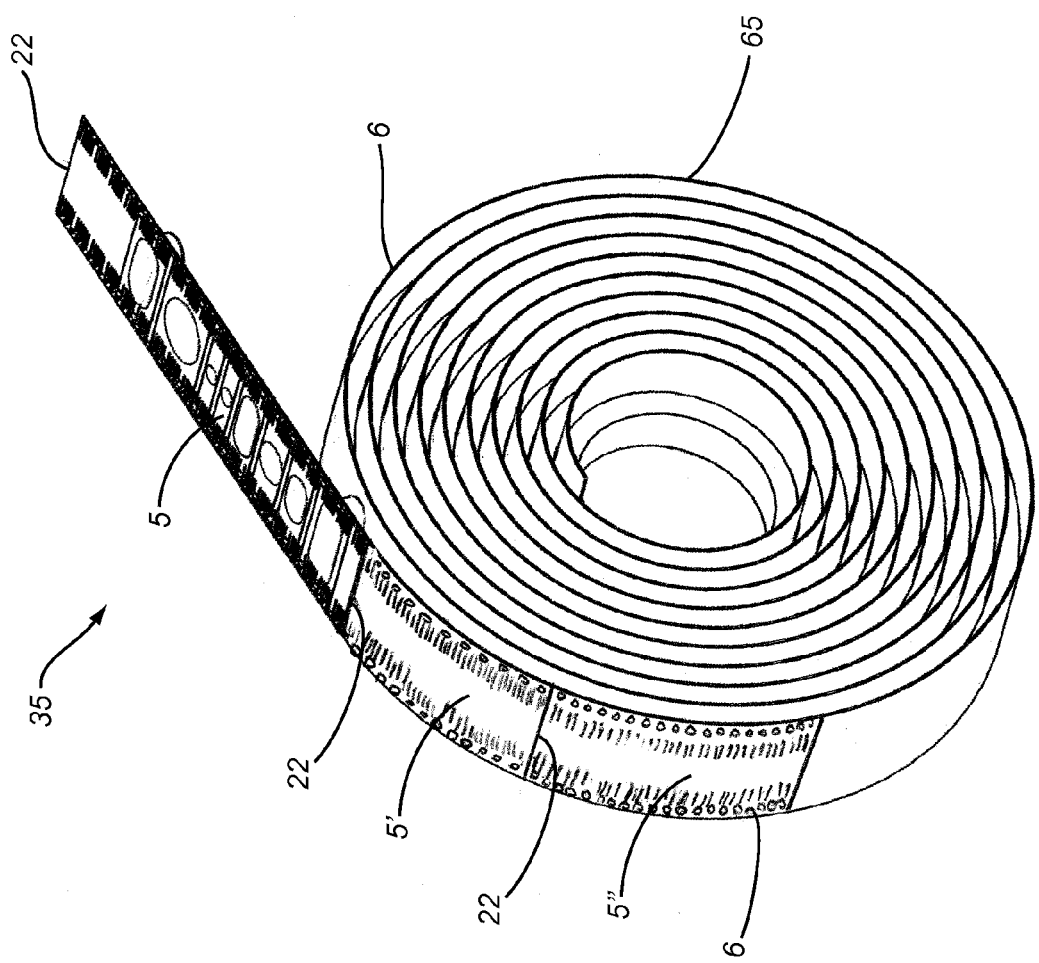
FIG. 2A is a perspective view of an exemplary embodiment of a substantially continuous strip of single-dose packages wound into a coil arrangement.

Still referring to FIG. 1A, the dose package 5 may be joined to adjacent packages (not shown) at respective ends 22 of the package 5. For example, in one embodiment, a series of packages may be formed from a substantially continuous length of cover 10 and base material 15, e.g., extending the entire length of a strip of packages. Optionally, a perforation or equivalent weakened region may be provided at the ends 22, e.g., as shown in FIG. 2A, such that dose packages 5 may be separated from one another by preferential tearing along the weakened region, while the cover 10, base 15, and blisters 18 of each dose package 5 remain substantially intact and/or inseparable (other than optional weakened regions 12, 13). Optionally, adjacent dose packages 5 may include variable numbers of blisters 18 and/or items 19, e.g., as appropriate for a sequence of doses to be administered to a patient, as described elsewhere herein. For example, as shown in FIG. 2A, a first single-dose package 5 may include nine (9) blisters, while the next single-dose package 5' may include fewer or more blisters.

Optionally, the cover 10 may include human-readable information 30, for example, printed information. The human-readable information 30 may include one or more of the intended patient's name, scheduled date of administration of the dose, scheduled time of administration of the dose, names and descriptions of items in respective blisters 18, and/or other desirable information.

Figure 1C:
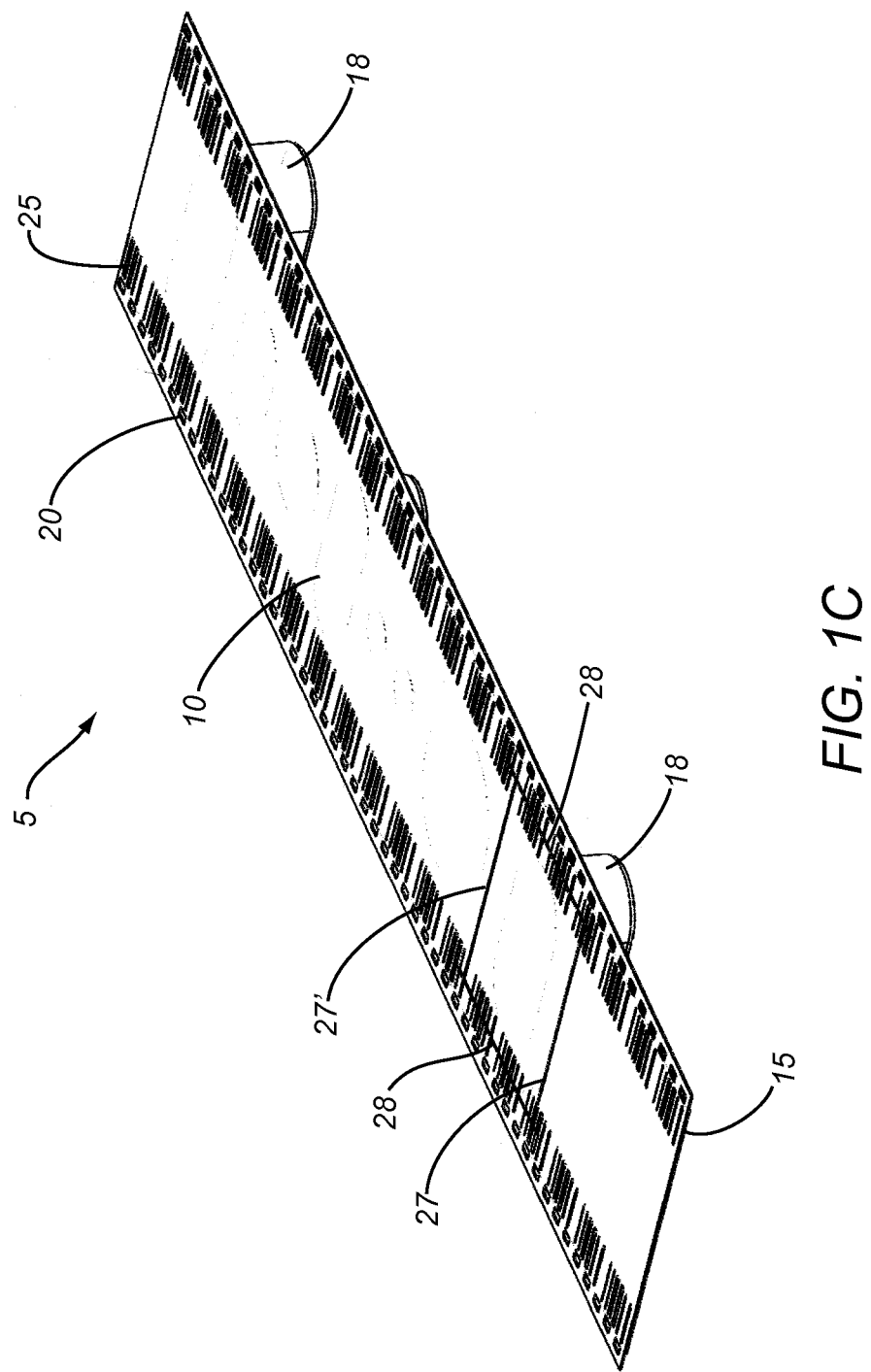
FIG. 1C is a perspective view of an alternative single-dose package similar to that of FIG. 1C, except including a different configuration for separating individual blisters from the rest of the package.

Referring to FIG. 1C, an alternate embodiment of a package 5 is shown that includes a different configuration for removing one or more unwanted items 19 from the package 5, e.g., by cutting through the cover 10 and base 15. Cross cuts 27 and longitudinal cuts 28 may be achieved using one or more blades, dies, Lasers, or other devices, e.g., within a dispenser or other housing (not shown) from which the package 5 is dispensed. For example, the cover 10 and base 15 may be substantially continuous and free from weakened regions around individual blisters 18, and cutting elements in the dispenser may be used to at least partially surround target blisters 18 with sufficient cuts to define a weakened region surrounding the target blister 18, e.g., to facilitate removal of one or more unwanted items 19 from the dose package 5, as described elsewhere herein. These weakened regions may also vary in length and/or other configuration. For example, a larger blister 18 may require a longer longitudinal cut 28, while a smaller blister 18 may only require a shorter longitudinal cut 28. Thus, longitudinal cuts 28 may vary according to blister size.

Turning to FIGS. 1D(1) and 1D(2), optionally, the cover 10 may include machine-readable information 25 on an outer surface of the cover, as shown in FIG. 1D(1), and one or more machine-readable confirmation codes 26 on the underside or inner surface of the cover 10, as shown in FIG. 1D(2). Access to the confirmation code requires the user to peel or otherwise separate the cover 10 from the base 15 (not shown). The use of confirmation code 26 is discussed further below.

The dose packages 5 may be joined to other dose packages 5 to form a substantially continuous strip 35 of sequential doses, e.g., including a plurality of single-dose packages 5 that may be separated from one another, e.g., by a dispenser or other container and/or manually by a user. As shown in FIG. 2A, dose packages 5, 5', and 5" are joined in temporal sequence in the form of a substantially continuous strip 35 with adjacent dose packages separated by connection features, e.g., weakened regions at the ends 22 of each package 5, 5', 5." As shown, the dose packages 5 are formed as a substantially continuous strip that is wound into a coil 65, although the strip may be arranged in other configurations, such as a serpentine or zigzag configuration, and the like (not shown). A given, e.g., first, dose package 5 at a first dispensing end of the strip may be joined to an adjacent, e.g., second, dose package 5,' which is intended for administration after the first dose package 5, e.g., separated by weakened regions and/or other connection features at the ends 22.

Figure 2B:
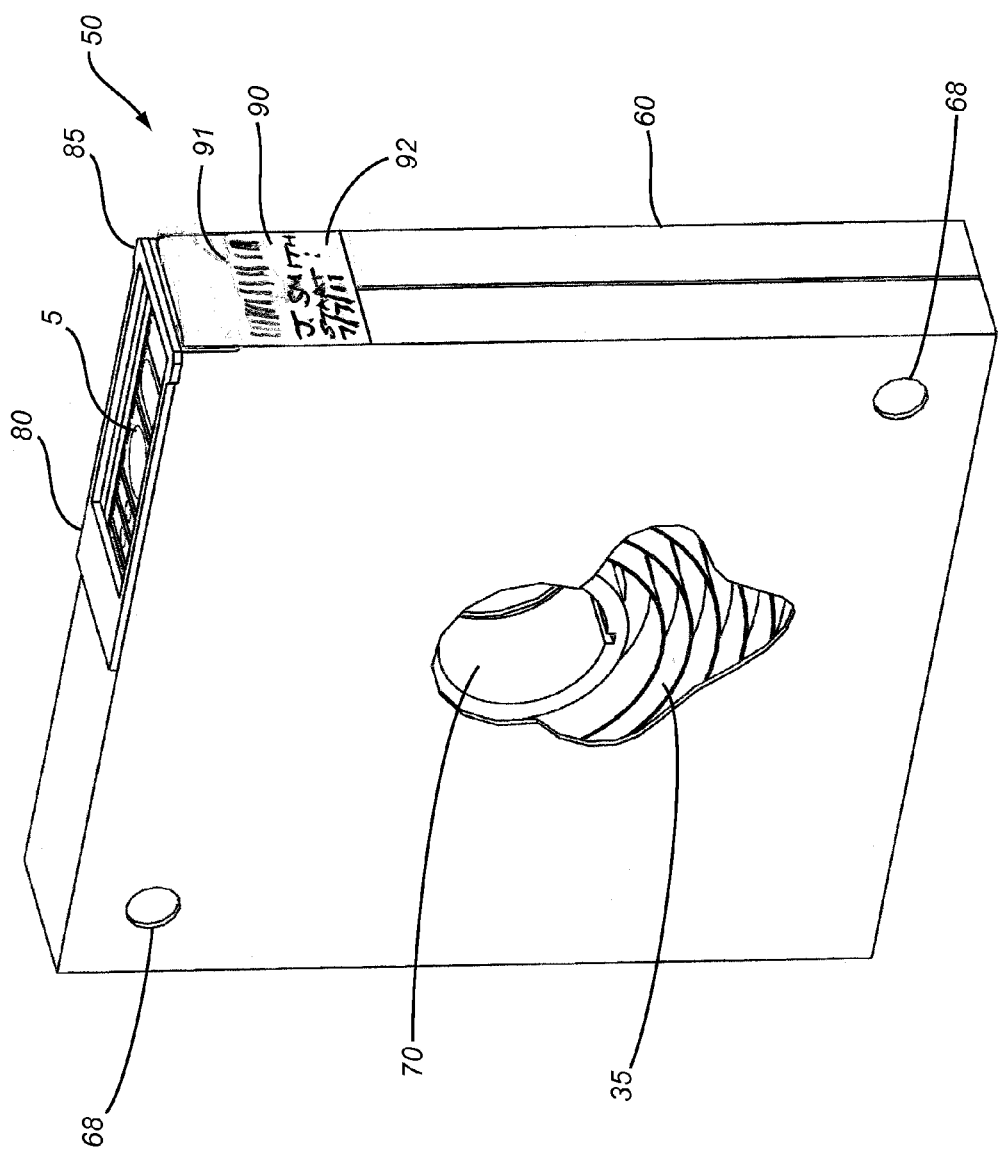
FIG. 2B is a perspective view of an exemplary embodiment of a cassette containing a substantially continuous strip of single-use packages, such as that shown in FIG. 2A.

Optionally, the strip 35 may be housed in a box, cassette, or other container. For example, as shown in FIG. 2B, the strip 35 is contained within a cassette 50. The cassette 50 includes a cassette housing 60 sized to receive the strip 35 in a coiled (or alternatively other) configuration, which may be a box, e.g., a folded structure, molded structure, vacuum formed structure, stamped structure, or equivalent, and may be formed of paper, polymer, metal, composite, or other suitable material. The cassette housing 60 may include optional alignment feature(s) 68, which may be used to align the cassette 50 with a dispenser, such as the dispenser 100 shown in FIG. 3 and described below. A first dispensing end of the strip 35 may extend from the cassette housing 60, e.g., temporarily secured to the cassette housing 60 by a housing label 90, while a second inner end of the strip may be secured to a core 70, e.g., rotatably mounted within the cassette housing 60. The housing label 90 may serve to provide tamper-evidence, and may include machine-readable information 91 and/or human-readable information 92, e.g., identifying the intended patient for the medications carried within the blisters of the strip 35 and/or a date range for the doses in the strip 35. The cassette 50 may also include a child-proofing feature 80, making it difficult for children to remove dose packages 5 from the cassette 50, as described further elsewhere herein.

Figure 2C:
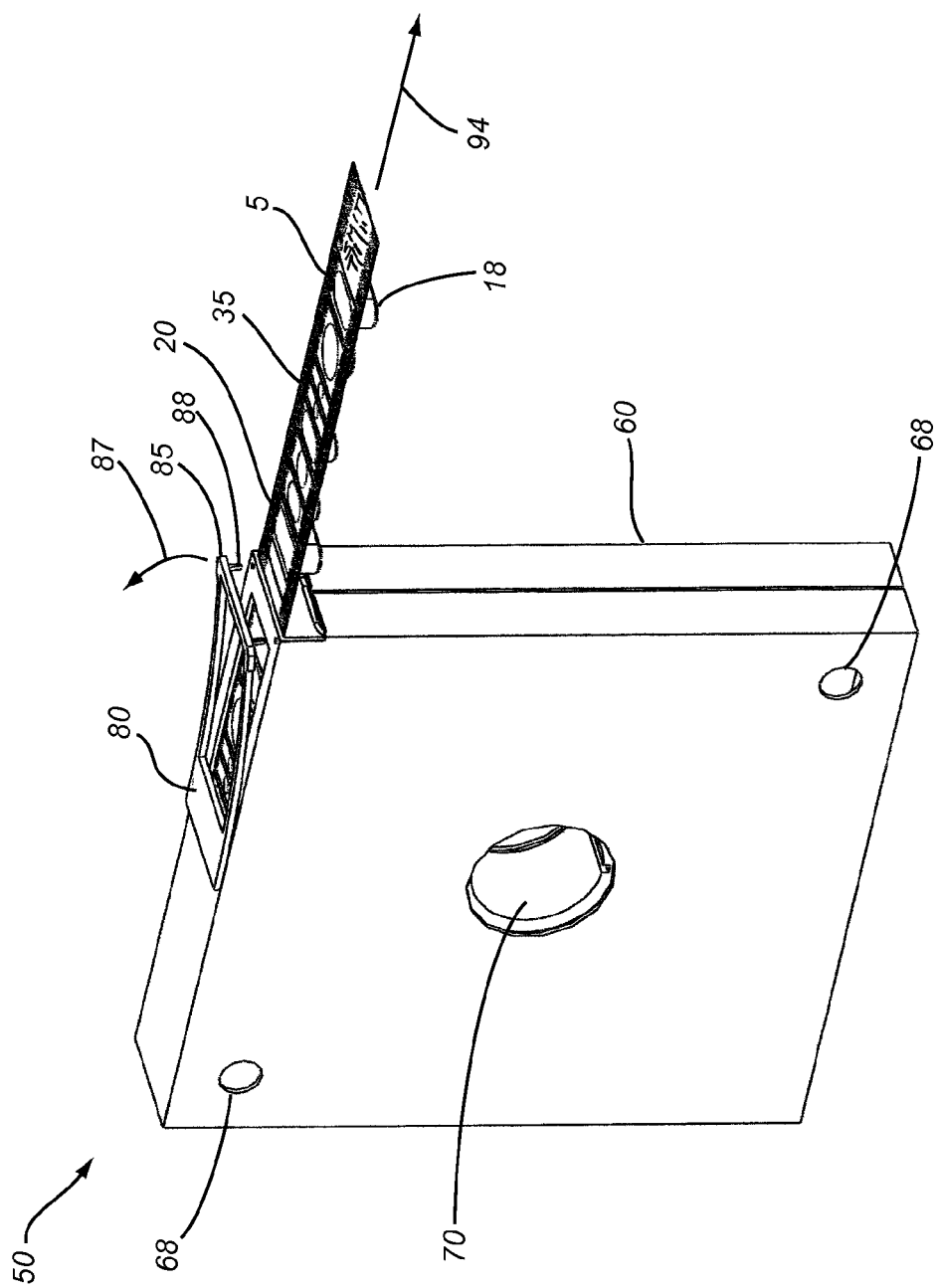
FIG. 2C is a perspective view of the cassette of FIG. 2B, showing a first single-use package on a first end of the strip being pulled from the cassette.

As shown in FIG. 2C, after removing the housing label 90, dose packages 5 may be removed from the cassette 50 by lifting lock tabs 85 of the child-proofing feature 80 along an unlock path 87, thereby pulling lock cleats 88 out of corresponding perforations 20, and permitting the strip 35 to be pulled out of the cassette 50 along strip path 94. This exposes the next dose package 5 on the dispensing end for the user.

Figure 3:
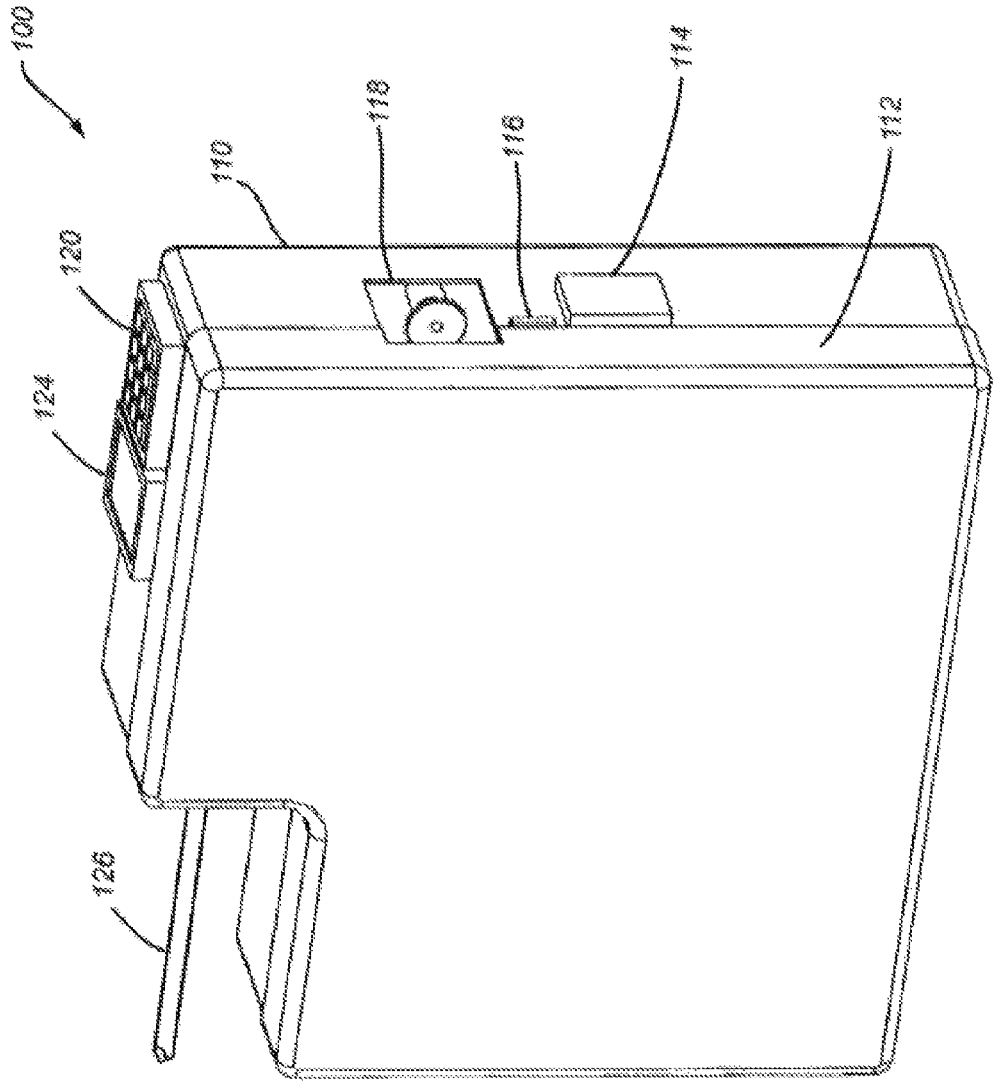
FIG. 3 is a perspective view of an exemplary embodiment of a dispenser for dispensing sequential dose packages, e.g., from a cassette loaded into the dispenser, such as that shown in FIGS. 2B and 2C.

The cassette 50 may be also be used with an automatic dispenser. For example, FIG. 3 shows a dispenser 100, which may be configured to receive the cassette 50 (not shown, see FIGS. 4A-4E) to automatically dispense dose packages 5, e.g., based on scheduled or intended times for administering medications and/or when desired, as described further below. The dispenser 100 generally includes a housing 110, cover 112, door lock 114, dispense aperture 118, power connection 126, user input device 120, and/or display 124. Optionally, a door sensor 116 may also be employed.

Figure 4A:
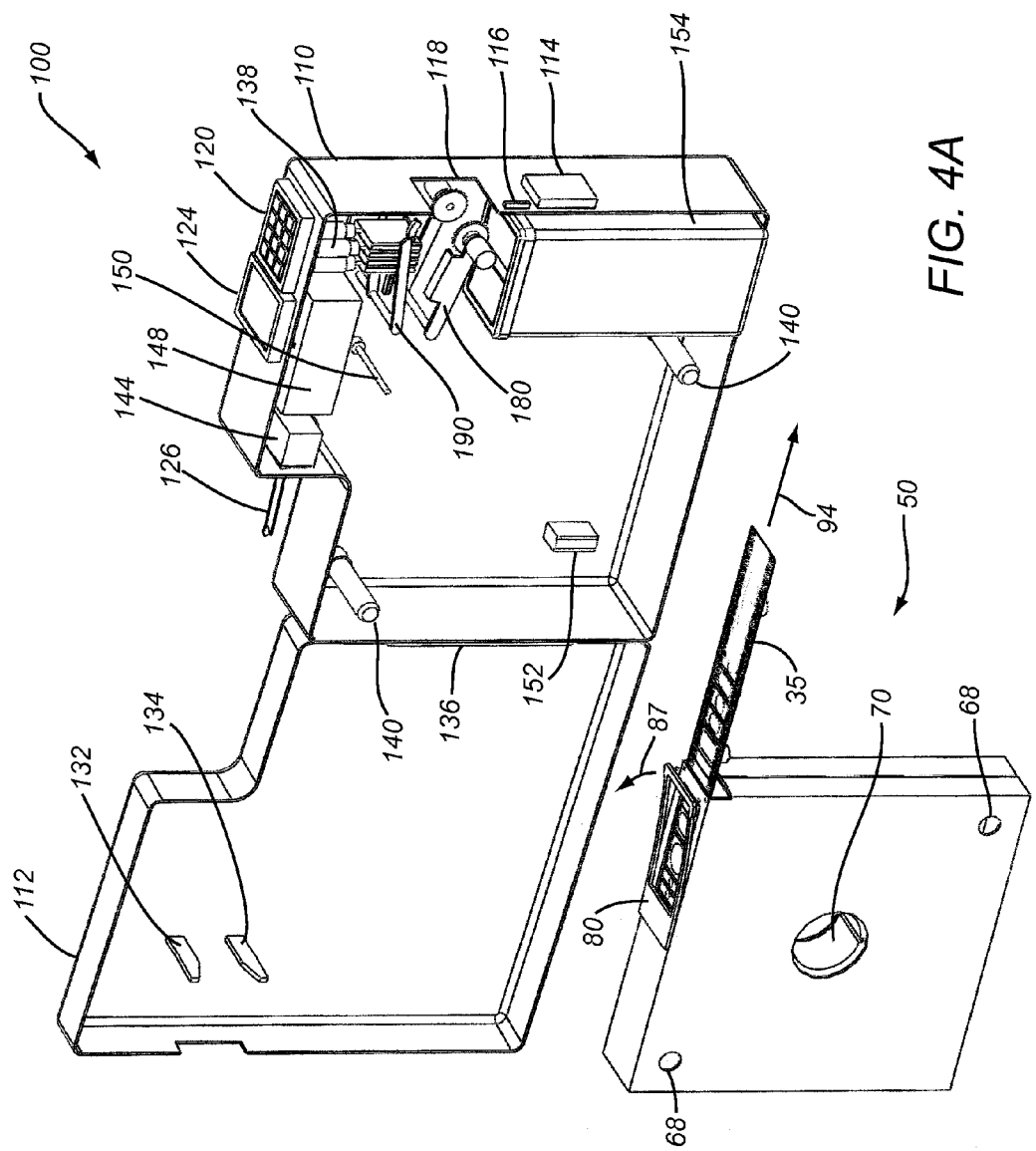
FIGS. 4A-4E are perspective views of the dispenser of FIG. 3, showing a method for loading a cassette including a strip of single-dose packages into the dispenser in preparation for dispensing the packages.

The cassette 50 may be loaded into the dispenser 100 as shown in FIGS. 4A-4E. Alternatively, in a similar manner, a strip wound in a coil configuration may be loaded directly into the dispenser 100 without a cassette 50 (not shown). In FIG. 4A, the dispenser 100 and cassette 50 are shown prior to loading. The cover 112 of the dispenser 100 is open, exposing various internal components or elements of the dispenser 100. A hinge 136 joins the cover 112 and housing 110. Optionally, one or more alignment elements, e.g., pins 140, in the housing 110 may cooperate with one or more corresponding alignment features, e.g., apertures 68, in the cassette 50 to locate and/or stabilize the cassette 50 in the housing 110.

In addition or alternatively, the dispenser 100 may include one or more additional components. For example, the cover 112 may include an upper cam 132 and a lower cam 134, whose use is described below. An optional barcode reader 152 (or other device for acquiring information from the cassette 50, e.g., information on an external label, not shown, on the cassette 50) may be mounted to the housing 110. A waste receptacle 154, whose use is described below, may also be provided. A power connection, e.g., an AC cord 126, may be provided, which may be coupled to electrical components of the housing 110 via AC transformer or module 144. A battery 148 may provide backup and/or mobile power, e.g., in addition to or instead of the cord 126 and module 144. One or more control circuits or controllers 119 may also be provided to manage and direct various functions of the dispenser 100.

Figure 4B:
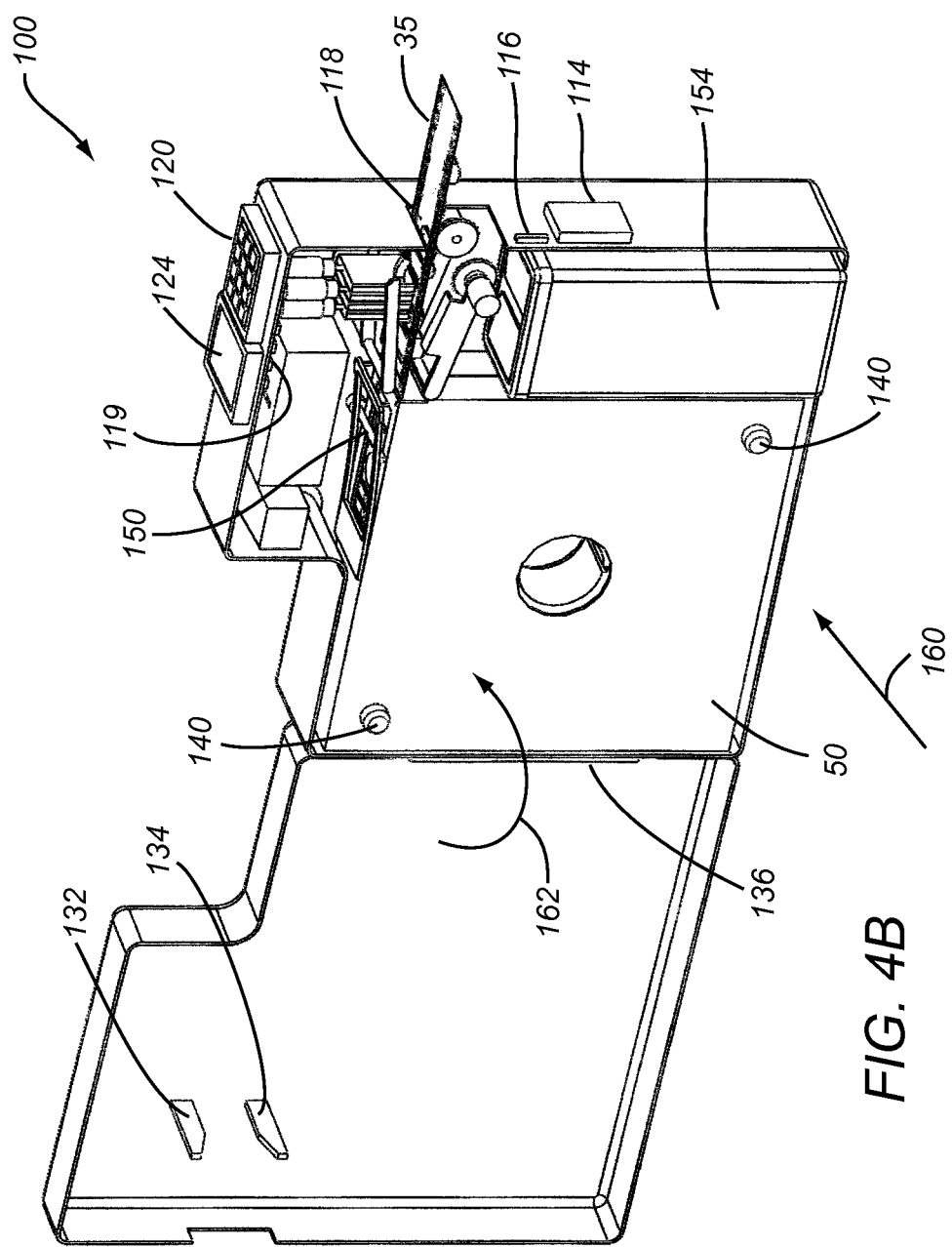
Figure 4C:
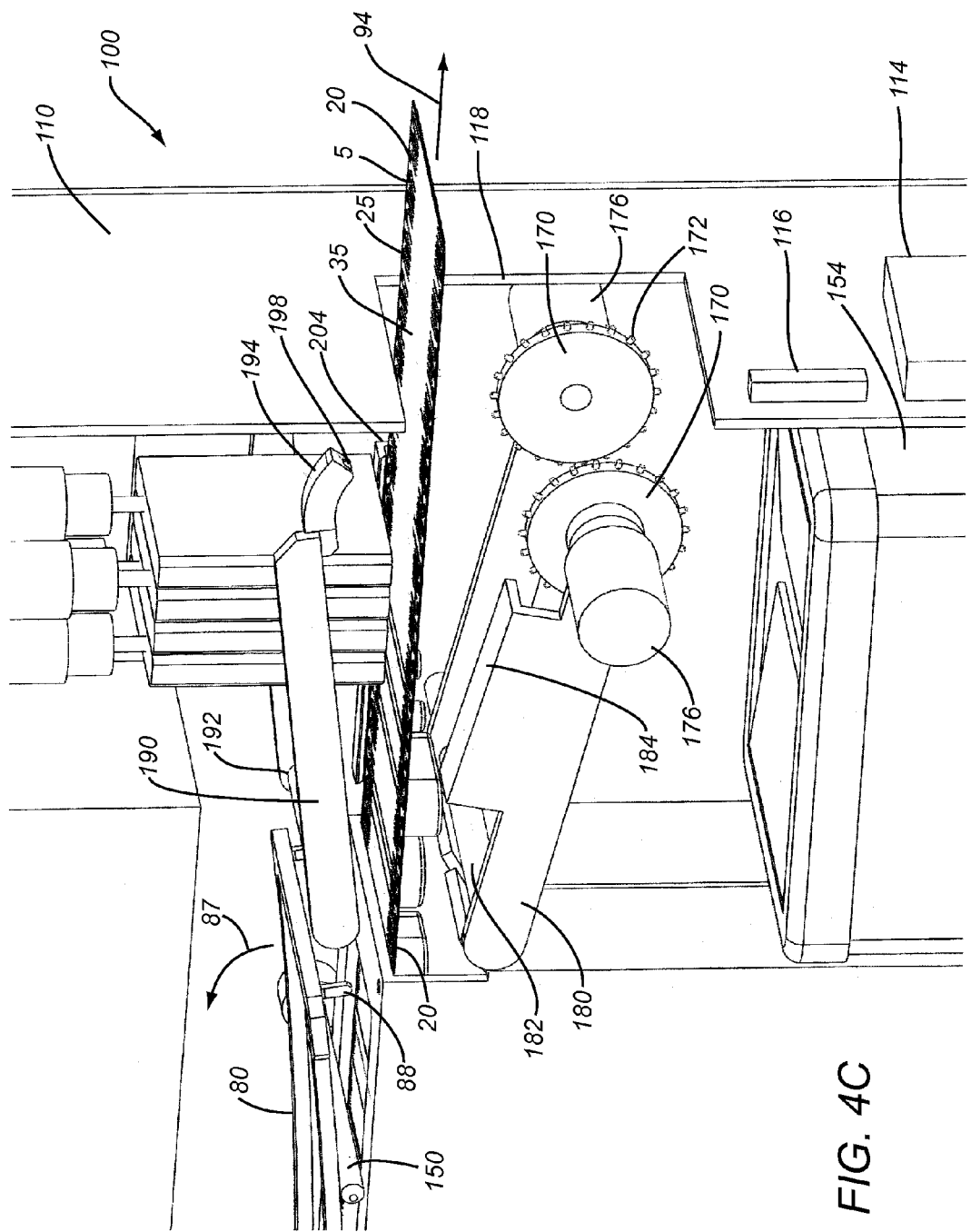

In FIG. 4B, the cassette 50 has been loaded into the dispenser 100. The dispensing end of the strip 35 has been fed through the dispenser 100 and extends partially through the dispense aperture or outlet 118. A closer view of the position of the strip 35 in the dispenser 100 is shown in FIG. 4C. As shown, the child-proofing feature 80 of the cassette 50 may be continuously or selectively held open by a holdback pin 150, thereby holding the lock cleats 88 out of the perforations 20, and permitting the strip 35 to be pulled out of the cassette 50 along the strip path 94. The strip 35 extends between an upper drive arm 190 and lower drive arm 180. The upper drive arm 190 carries guide form 194, which includes guide groove 198. The upper drive arm 190 may pivot about upper axle 192. The lower drive arm 180 carries one or more drive rollers 170 (two shown), which include drive teeth 172 and is coupled to drive motor(s) 176, which is coupled to the controller 119. The lower drive arm 180 also carries a support shelf 184. The lower drive arm 180 may pivot about lower axle 182. Thus, the upper drive arm 190 and lower drive arm 180 may be rotatable or otherwise movable between open positions, e.g., as shown in FIGS. 4A-4C, to facilitate feeding or loading the dispensing end of the strip 35 therebetween, and closed positions, e.g., as shown in FIG. 4D, in preparation for operation and use of the dispenser 100.

Figure 4D:
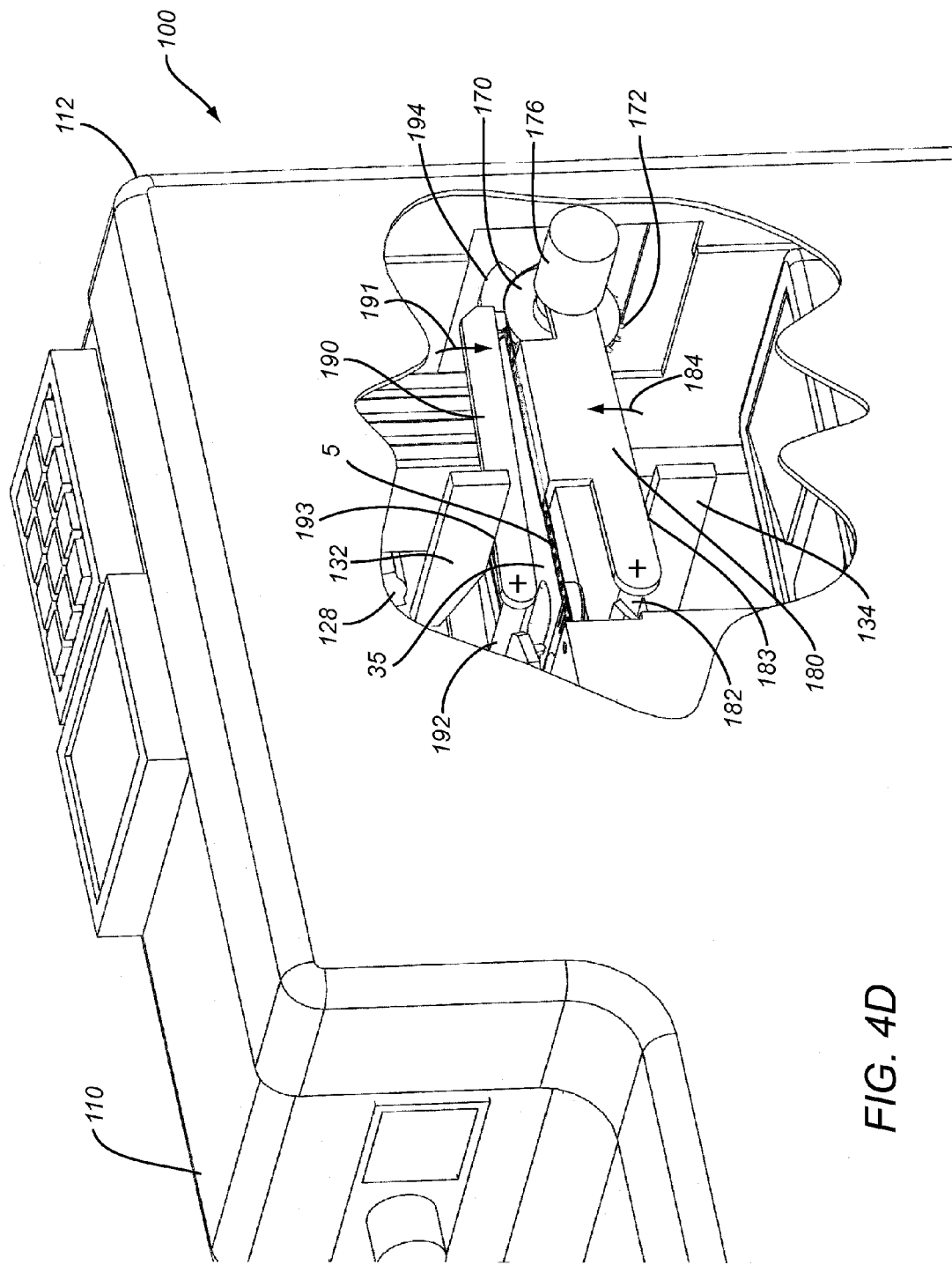

For example, in one embodiment, FIG. 4D shows the effect of closing the cover 112, e.g., by pivoting at the hinge 136 approximately along path 162 (shown for illustration through a hole in the cover 112), to automatically direct the drive arms 190, 180 from the open positions to the closed positions. The upper drive arm 190 is contacted by the ramped surface of the upper cam 132 approximately at upper cam point 193 and is thereby driven down along upper drive arm path 191. Similarly, the lower drive arm 180 is contacted by the ramped surface of the lower cam 134 at lower cam point 183 and is thereby driven up along lower drive arm path 184. The motion of the drive arms causes them to close on the strip 35, thereby engaging the drive roller(s) 170 and guide form 194 with the strip 35, e.g., to permit the strip 35 to be driven forward for dispensing of dose package(s) 5.

Figure 4E:
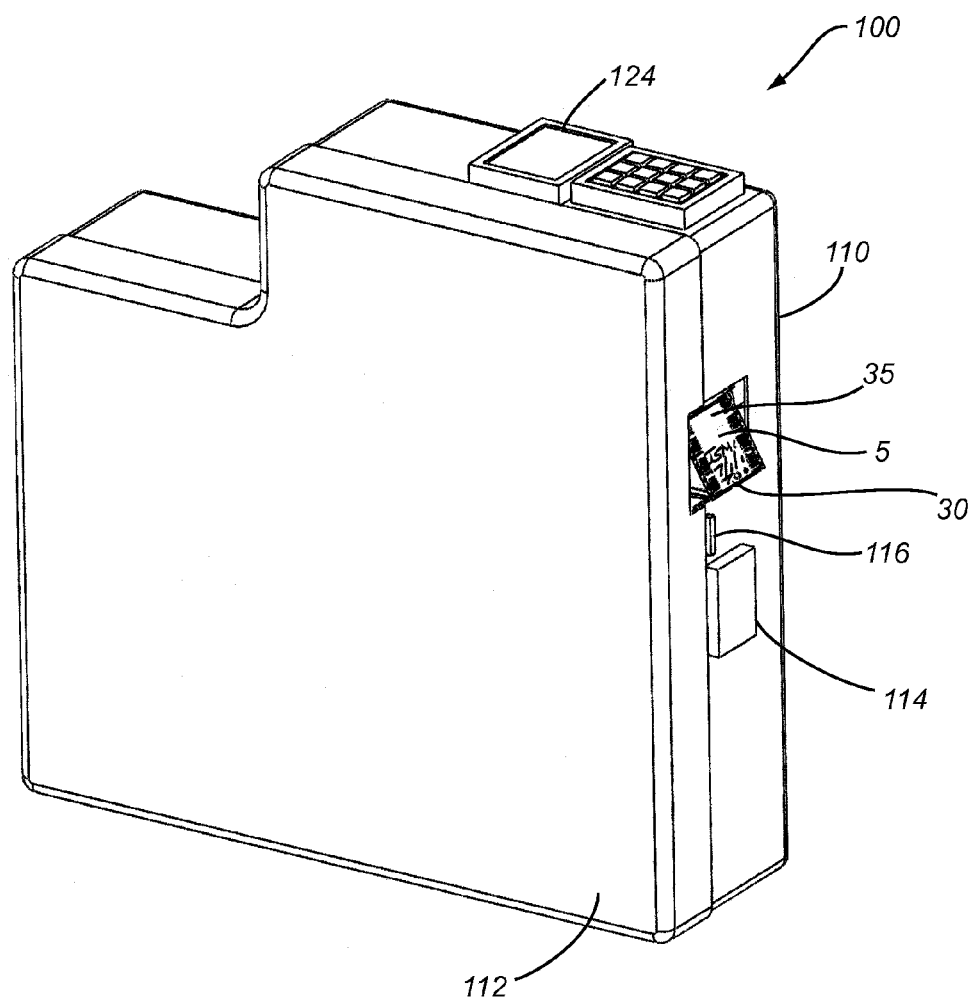

Once the cover 112 is closed, and the drive roller(s) 170 and guide form 194 engage the strip 35, the door lock 114 may be used to secure the cover 112 to the housing 110. An optional door sensor 116 may signal the control circuit 116 (not shown) that the cover 112 is properly closed, and that dispensing may begin, as described below. As shown in FIG. 4E, the dispensing end of the strip 35, and the first dose package 5, may be partially exposed from the outlet 118 and/or otherwise ready for automated dispensing.

Figure 5A:
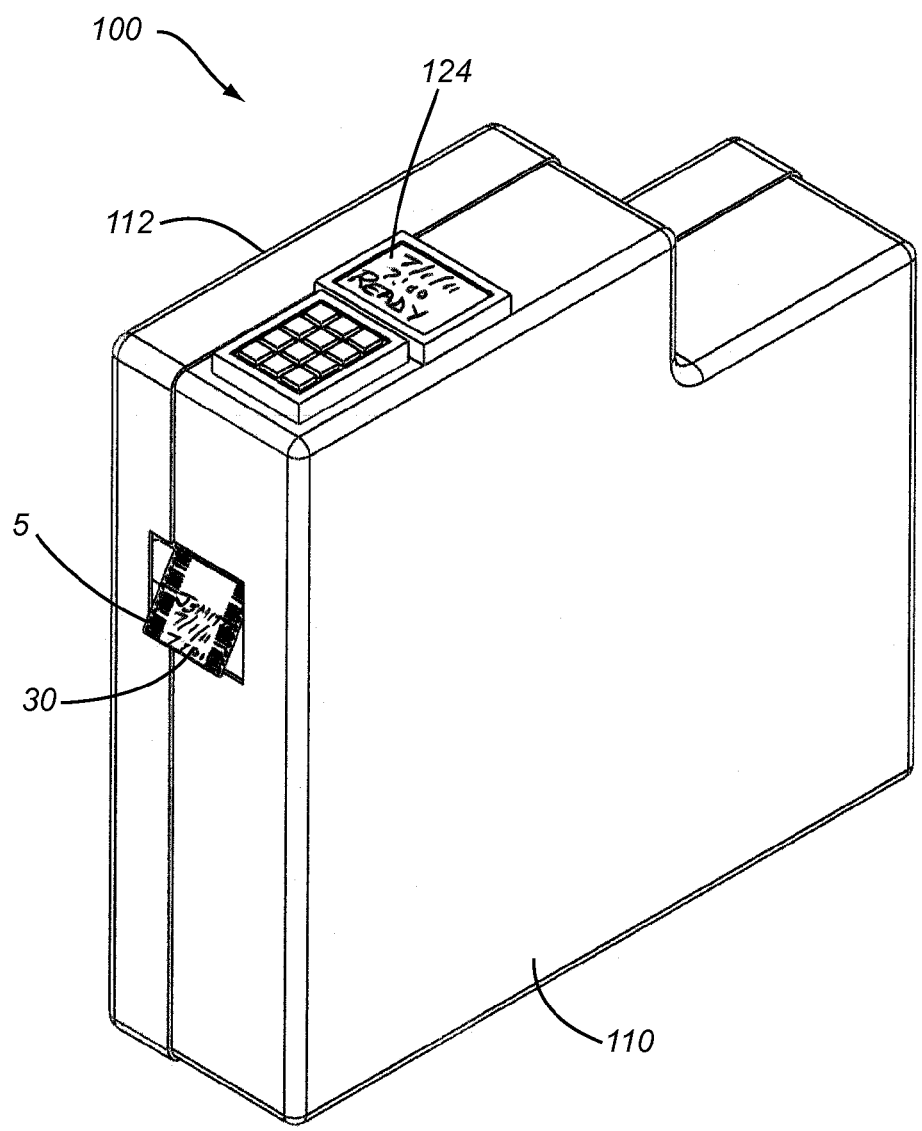
FIGS. 5A-5C are perspective views of the dispenser of FIG. 3, showing a method for dispensing a dose package from a cassette loaded into the dispenser.

Prior to dispensing a first or next dose package, the dispenser 100 may be activated or automatically directed to a "ready" mode, as shown on optional display 124 in FIG. 5A. The end of the first or next dose package 5 may be at least partially visible in the dispense aperture 118. The human-readable information 30 on the dose package 5, e.g., on a leading end of the dose package 5, may also be visible to the user, and thus the intended or scheduled time and date of the next dose may be easily viewed. The date and time of the next dose may also be shown on the optional display 124.

Figure 5B:
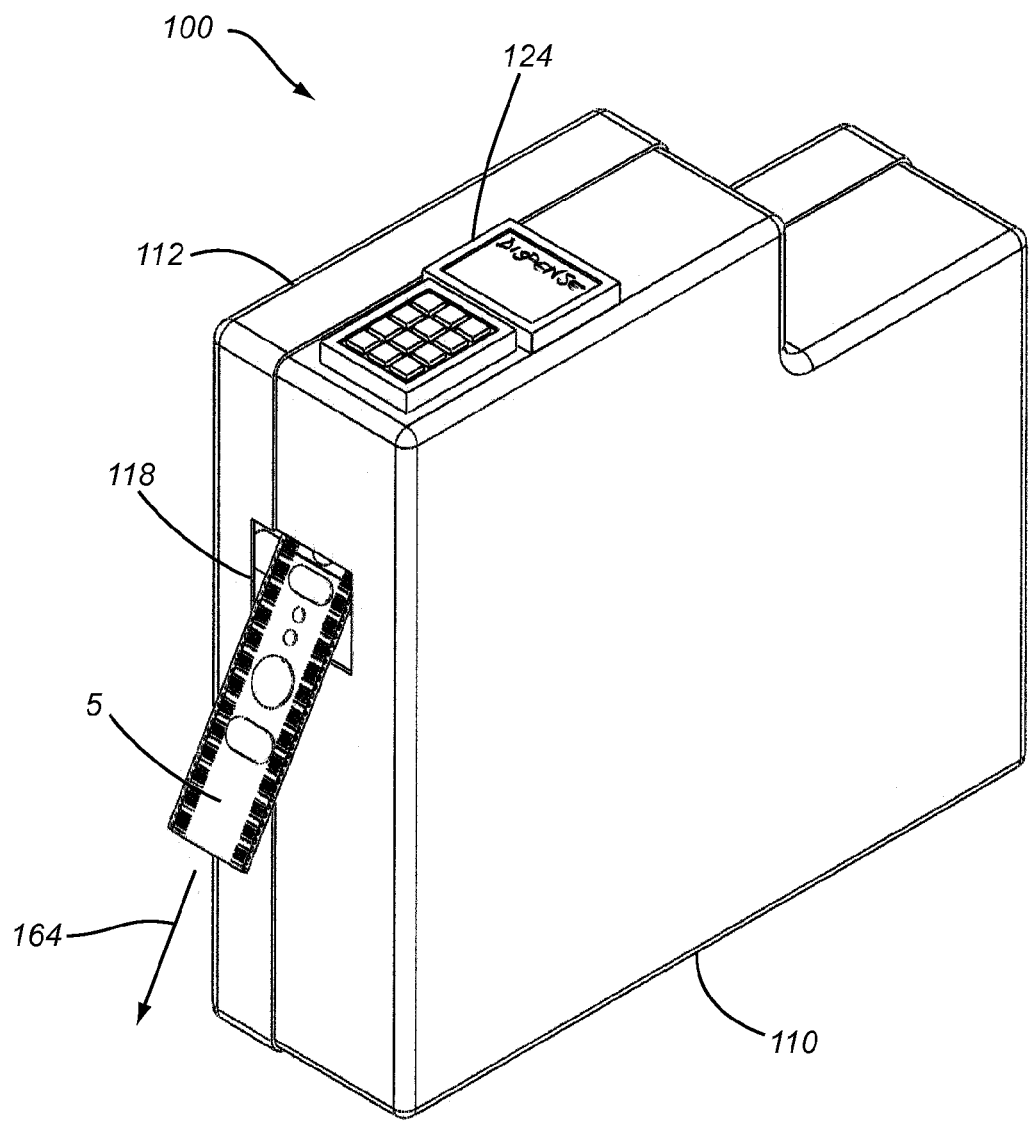
Figure 5C:
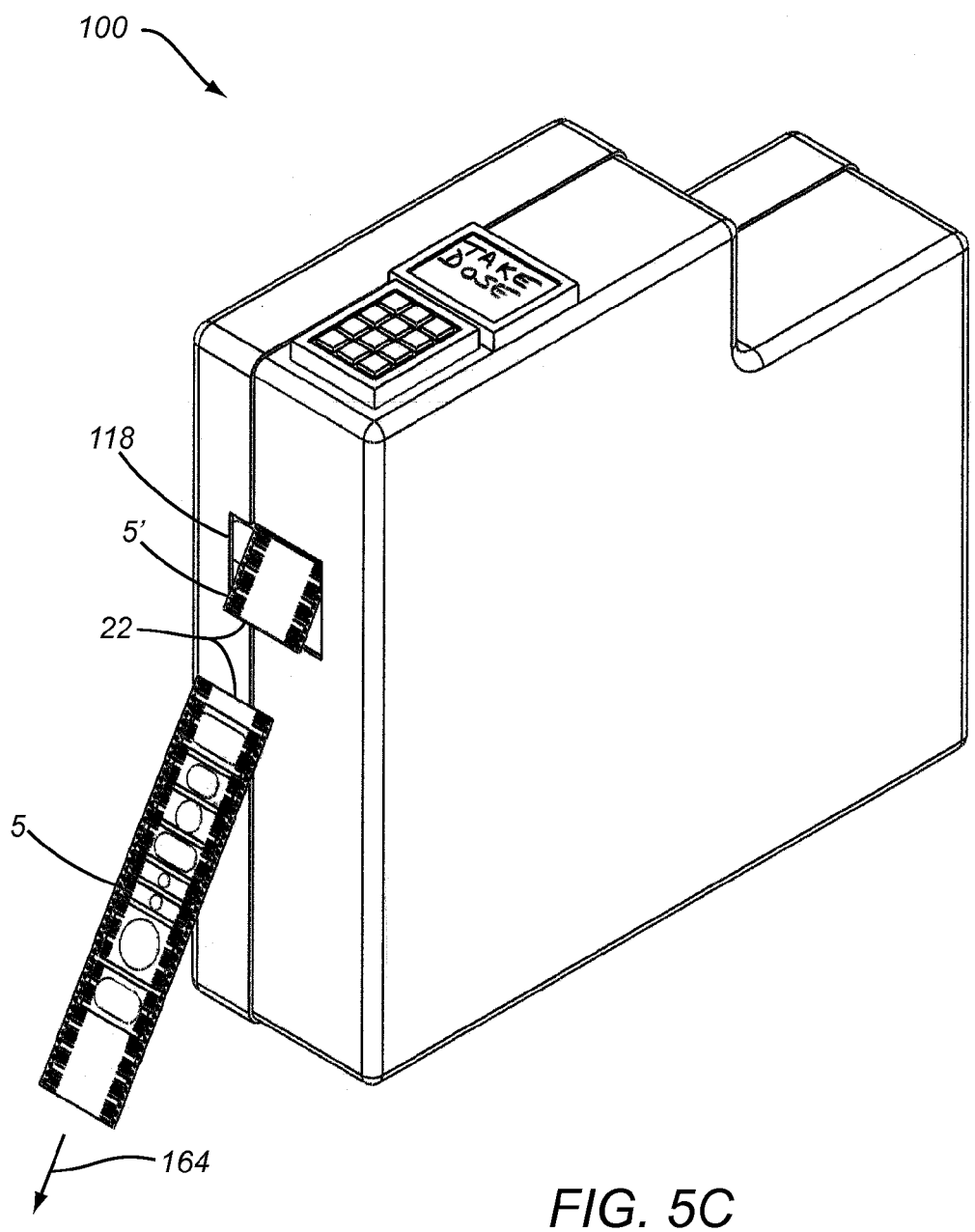

At the appropriate time, the dispenser 100 may advance, release, or otherwise present the entire first or next dose package 5. The dispenser 100 may push the first dose package 5 completely out of the dispense aperture 118 approximately along dispense path 164, as shown in FIG. 5B. Once the dose package 5 is fully dispensed, the user may detach the dose package 5 at weakened region or other connection feature on the trailing end 22, as shown in FIG. 5C. Optionally, one or more blades (not shown) may be provided, e.g., in or adjacent the dispense aperture 118, to cut, sever, or otherwise ease detachment of the dispensed dose package 5 from the next dose package. Optionally the blades may be actuated by means of actuators (also not shown). The dispenser 100 may alert the user that the dose has been dispensed, e.g., using an audible alarm (for example, coupled to control circuit 116), a visual indication (for example, using the display 124), or other indicator. As a result, the next dose package 5' may be left in the "ready" position, e.g., at least partially extending from the dispense aperture 118 of the dispenser 100.

In some cases, it may be desirable to remove undesired items 19 from a dose package, e.g., dose package 5, before presenting the dose package 5 entirely from the dispenser 100. For example, a drug (item) may be causing side effects in the patient or medical conditions may have otherwise changed since the strip 35 and cassette 50 was prepared and loaded into the dispenser 100. For example, as described further elsewhere herein, the dispenser 100 may access a patient database and determine that the patient's medications have changed. In this case, a system and method for removing any unwanted items from the strip 35, e.g., to prevent undesired administration of the unwanted item, would be beneficial.

Figure 6A:
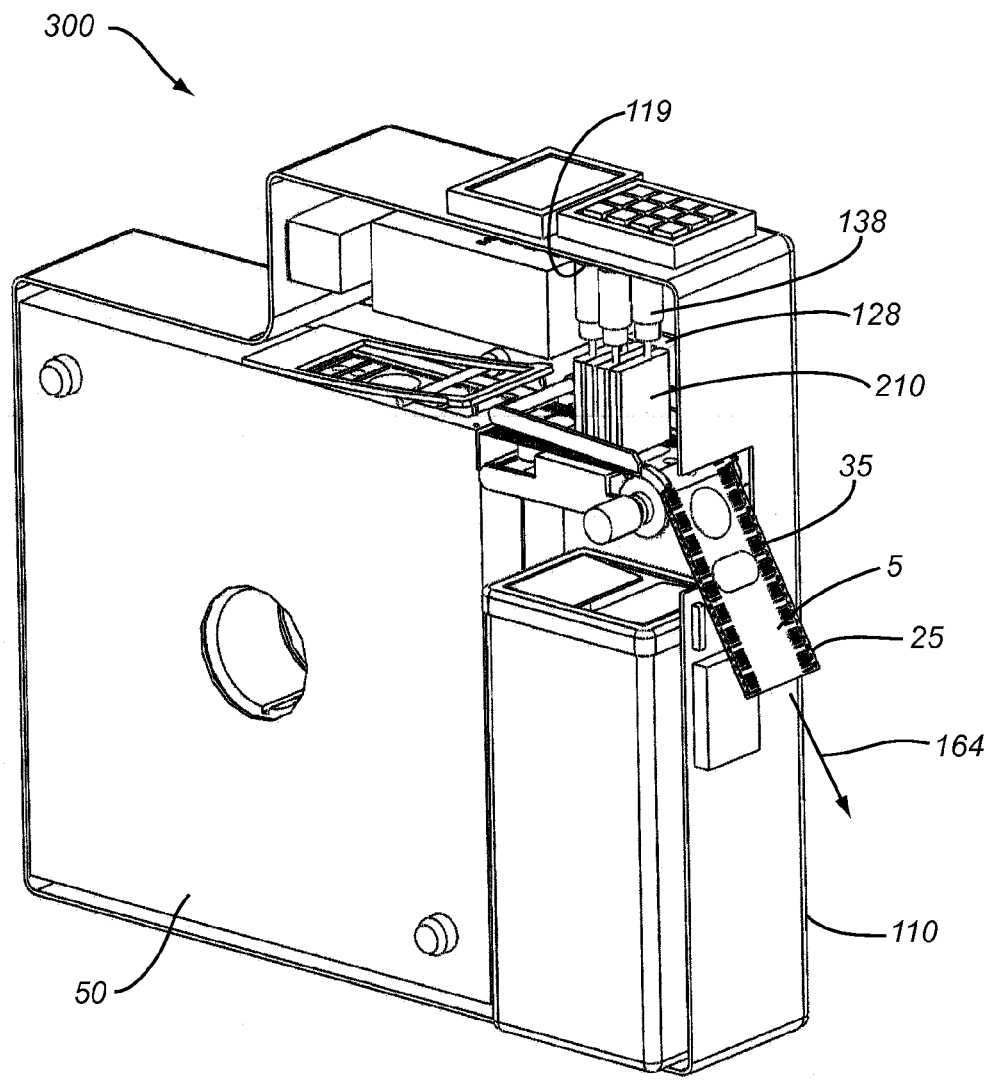
Figure 6B:
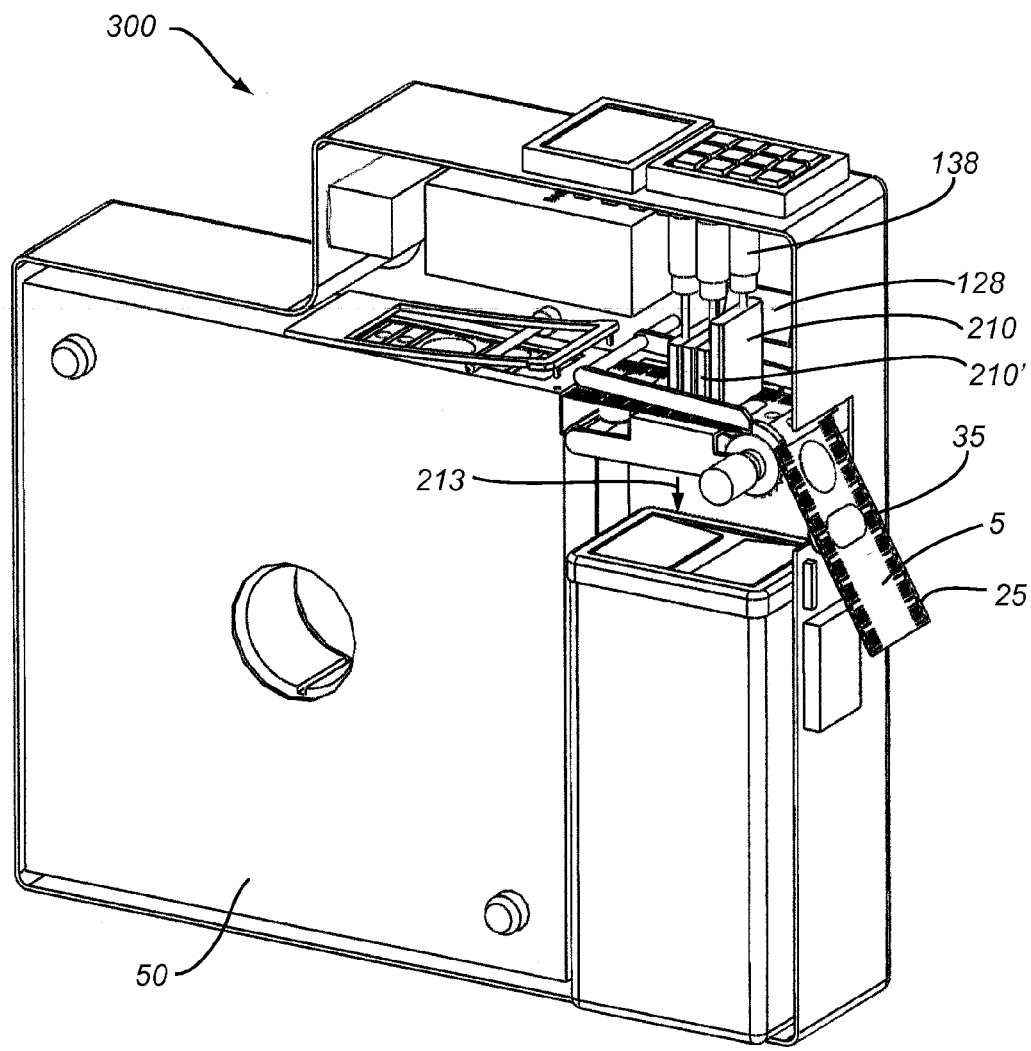

In FIG. 6A, a dispenser 300 is shown (with the cover 112 omitted simply for clarity) that includes one or more features, e.g., punches 210, for removing unwanted items 19 from each dose package before being dispensed. The cassette 50 has been loaded into the housing 110, and the strip 35 of dose packages 5 may be advanced along dispense path 164, as described above. As the strip 35 advances, a machine code sensor 128 (for example, a barcode reader) coupled to the controller 119 may detect and monitor the machine-readable information 25 on each dose package 5, e.g., as it becomes the first dose package adjacent the outlet 118, in order to identify and locate any unwanted items 19 in the dose package 5. For example, the controller 119 may compare the medications in the dose package 5 (based on the information 25) with a schedule of medications for the intended patient, e.g., stored in a patient database in memory of the controller 119 or accessed remotely, to confirm whether all of the medications are scheduled to be administered to the intended patient.

Figure 6D:
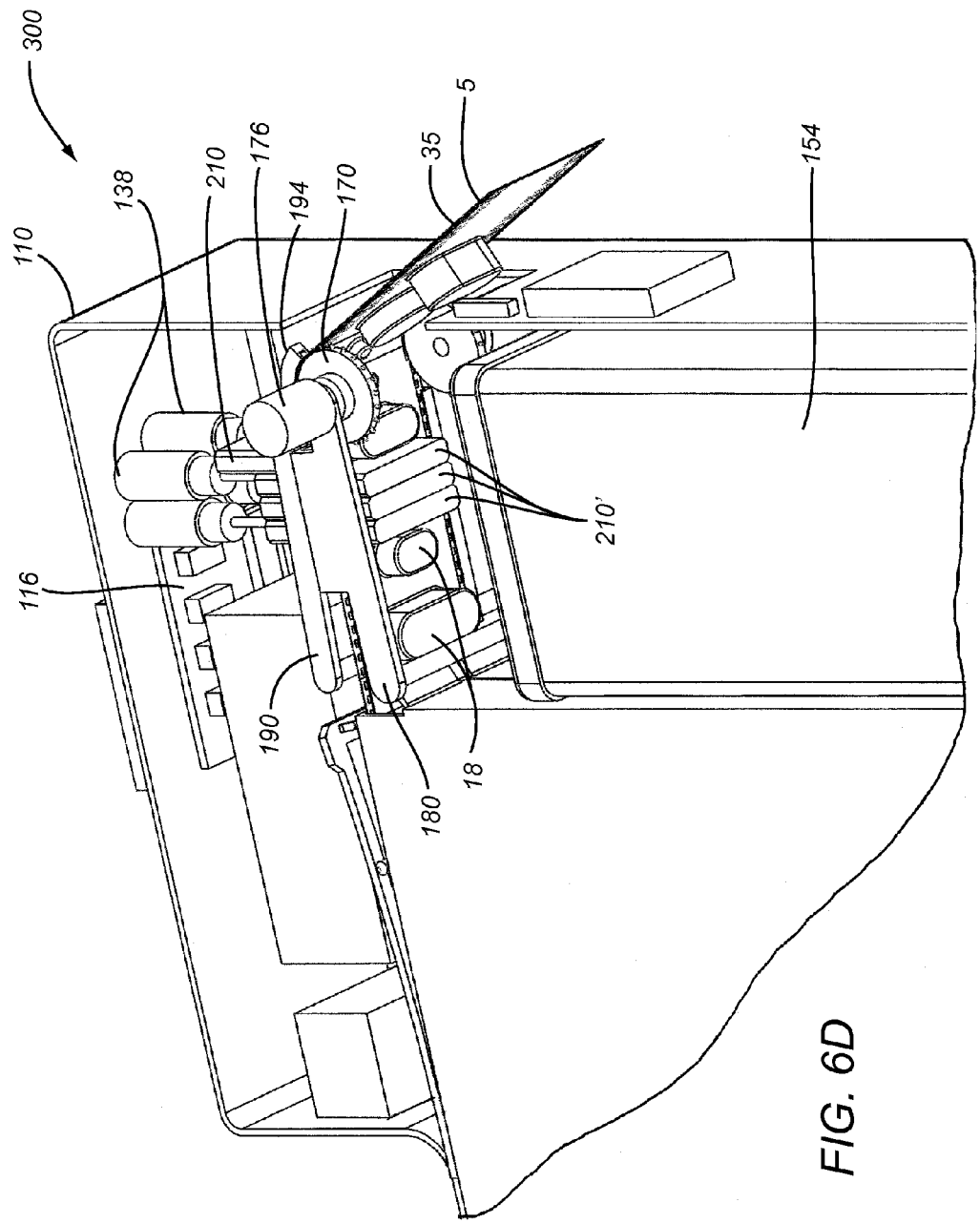

Once an unwanted item 19 has been located and positioned relative to the punches 210, advancement of the strip 35 is stopped by the controller 119, with the target unwanted item 19 in the dose package 5 in position under removal punch(es) 210. The appropriate number of removal punches 210 is driven down approximately along punch path 213 by corresponding actuator(s) 138, e.g., coupled to the controller 119, which are attached to the removal punches 210. The actuated removal punches 210 in FIG. 6D are designated by number 210.' The actuators 138, which actuate removal punches 210, may be solenoid, motorized, electric, pneumatic, or otherwise actuated. FIG. 6C is a section view through the center of the strip 35. The actuated removal punches 210' (in this case three out of four removal punches 210) are shown penetrating through the dose package 5.

The force of the removal punches 210 against the dose package 5 causes separation of the blister 18' containing the unwanted item 19,' e.g., at weakened region surrounding the blister 18' (e.g., defined by perforations 12 and 13 shown in FIG. 1A). As best seen in FIG. 6C, the unwanted item 19,' in its corresponding blister 18,' has separated from the dose package 5 at cross perforations 12 and longitudinal perforations 13 (see FIG. 1A), and been pushed out of the dose package 5 approximately along punch path 213.

The unwanted item 19' still contained within its blister 18' then falls into the waste receptacle 154. As shown, the waste receptacle 154 may include a pair of doors that may be opened when a blister 18' falls against it, and then automatically close. Alternatively, the door(s) to the waste receptacle 154 may be controlled by the controller 119, e.g., to limit access to the waste receptacle 154, e.g., to prevent unauthorized personnel from removing discarded medications received in the waste receptacle 154. Optionally, the waste receptacle 154 may include a door or other access panel that may be locked or the entire waste receptacle 154 may be locked but removable from the housing 110, thereby limiting access to the contents to the waste receptacle 154 to authorized users.

Figure 6E:
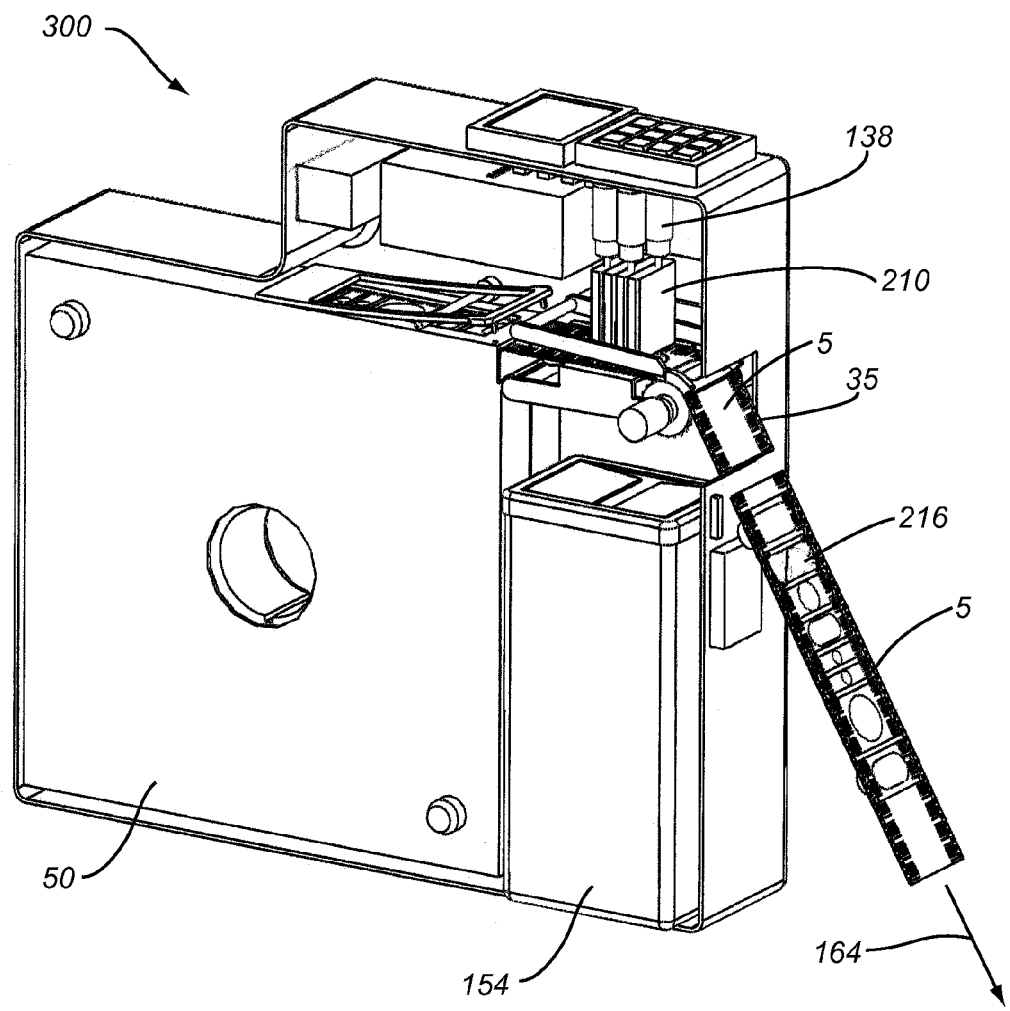

For further clarification of the action of the removal punches 210, FIG. 6D shows the dose package 5 from underneath, with the actuated removal punches 210' extending through the dose package 5, having separated the blister 18' from the dose package 5. The blisters 18 containing desired items 19 still to be administered to the intended patient remain undisturbed in the dose package 5. As shown in FIG. 6E, once the unwanted item 19 has been removed from the dose package 5, the removal punches 210 may be retracted by the actuators 138, and the strip 35 may be advanced along the dispense path 164 when the dose package 5 is dispensed. The dose package 5 now has an aperture 216 where the blister 18' was previously located.

Figure 7A:
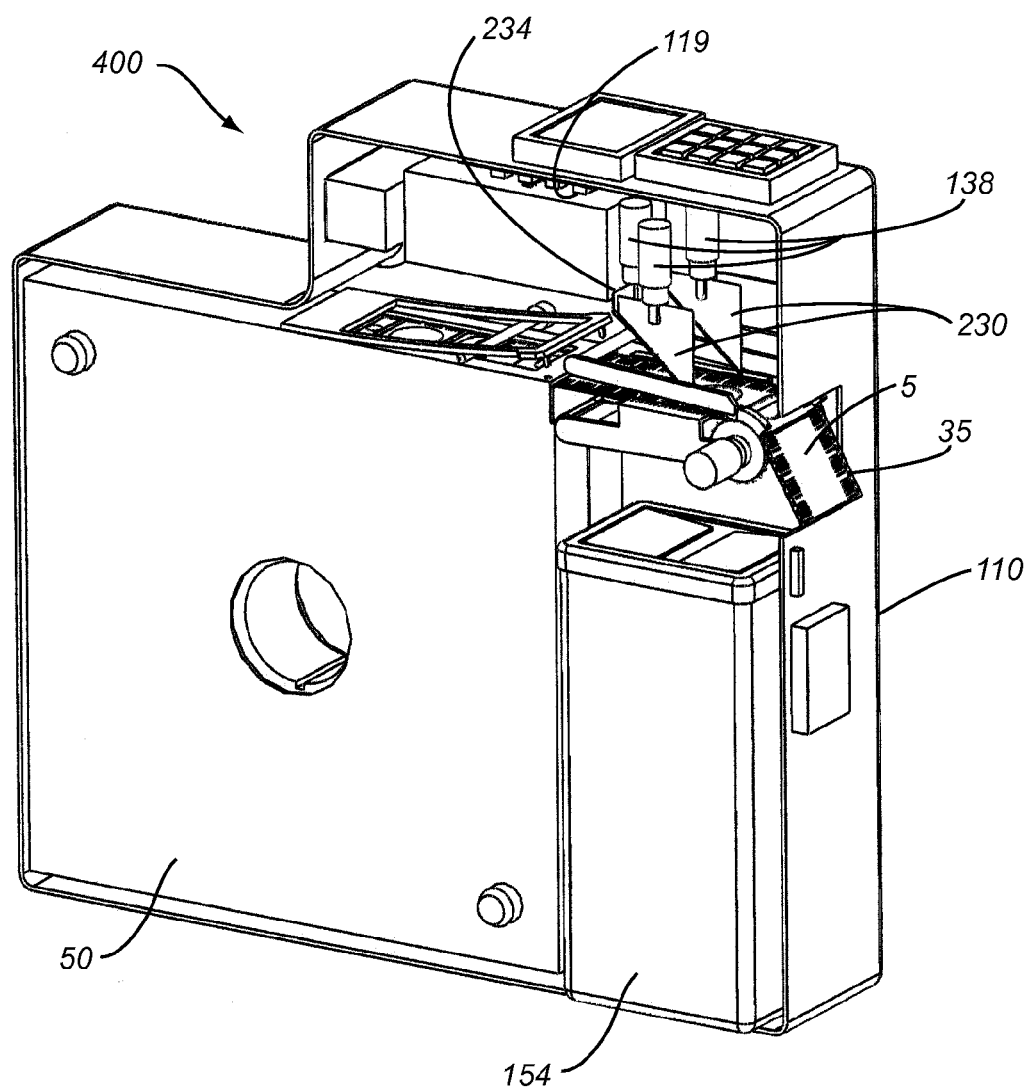
Figure 7B:
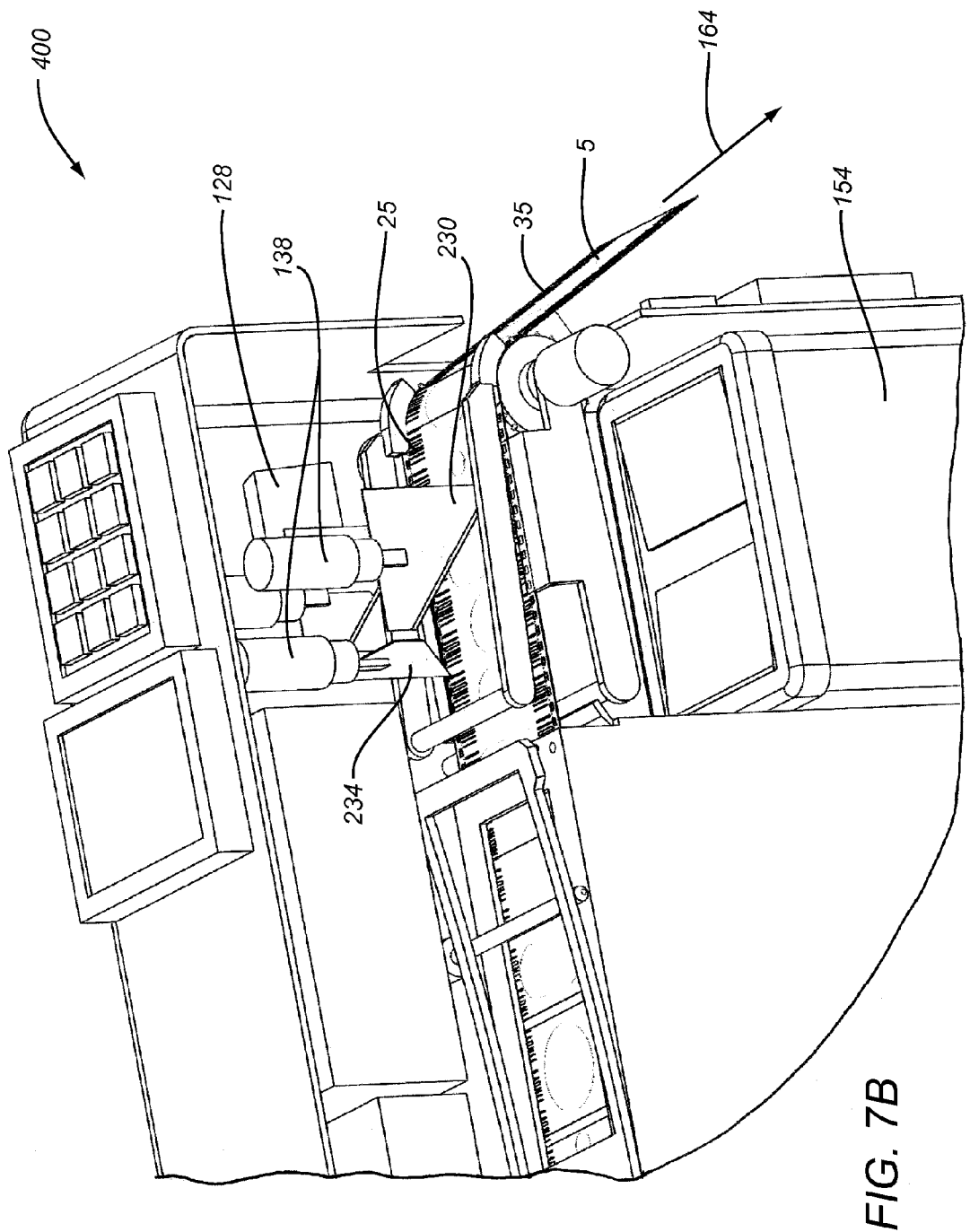

An alternate system and method for removing unwanted items from dose packages 5, e.g., by cutting them out of the dose package 5, is shown in FIGS. 7A-7G. FIG. 7A shows a dispenser 400 that includes one or more cutting elements, e.g., longitudinal blades 230 and cross blade 234, connected to actuators 138 coupled to the controller 119. The actuators 138, which actuate the blades, may be solenoid, motorized, electric, pneumatic, or otherwise actuated. An alternate view is shown in FIG. 7B. As the strip 35 is advanced along the dispense path 164, the machine code sensor 128 (for example, a barcode reader) may monitor the machine-readable information 25 on the dose package 5, in order to locate any specific unwanted items 19 in the dose package 5. Once the unwanted item 19 has been located and positioned, the controller 119 stops advancement of the strip 35 with the unwanted item 19 in the dose package 5 in position under cross blade 234.

Figure 7C:
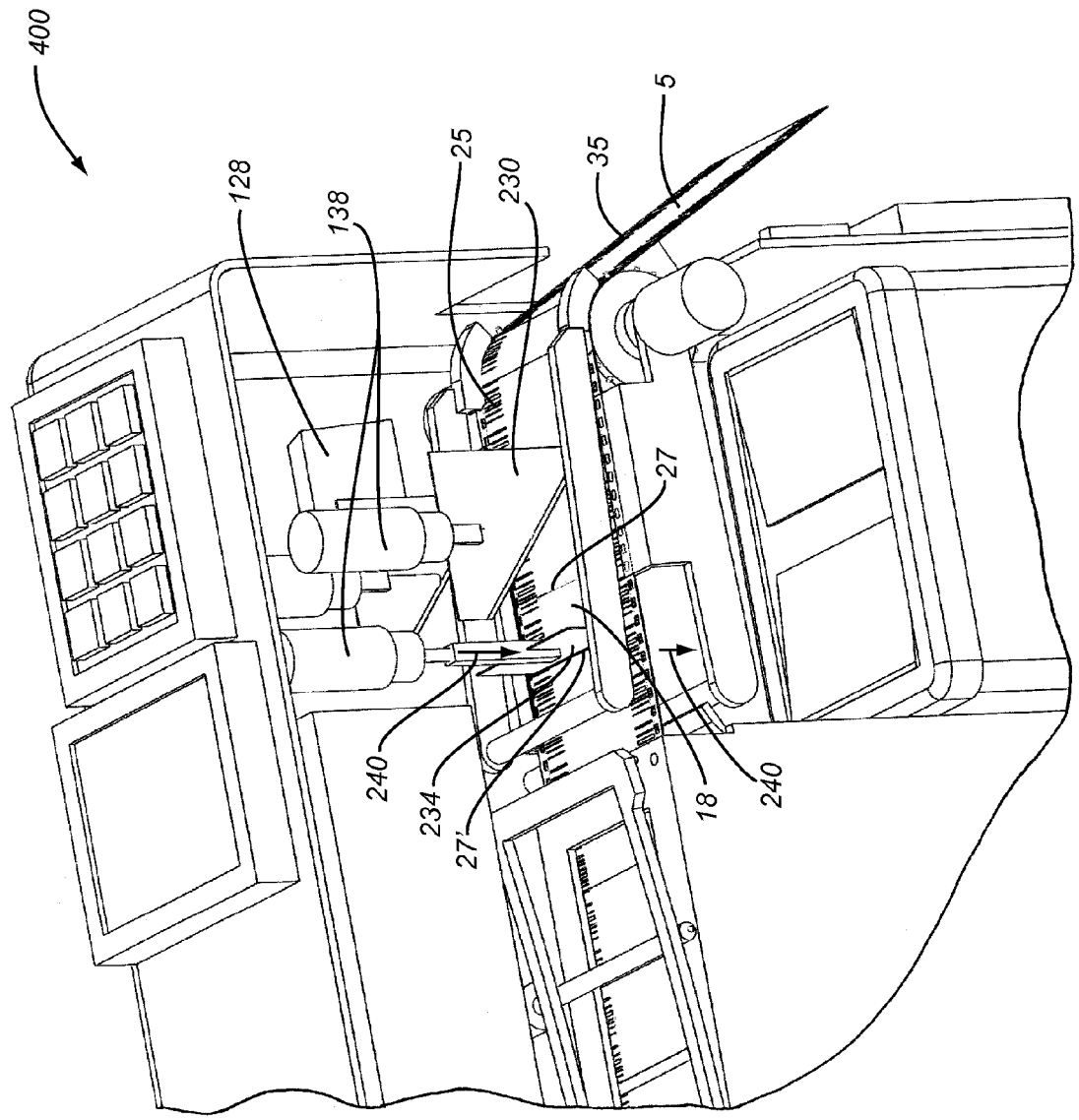
Figure 7D:
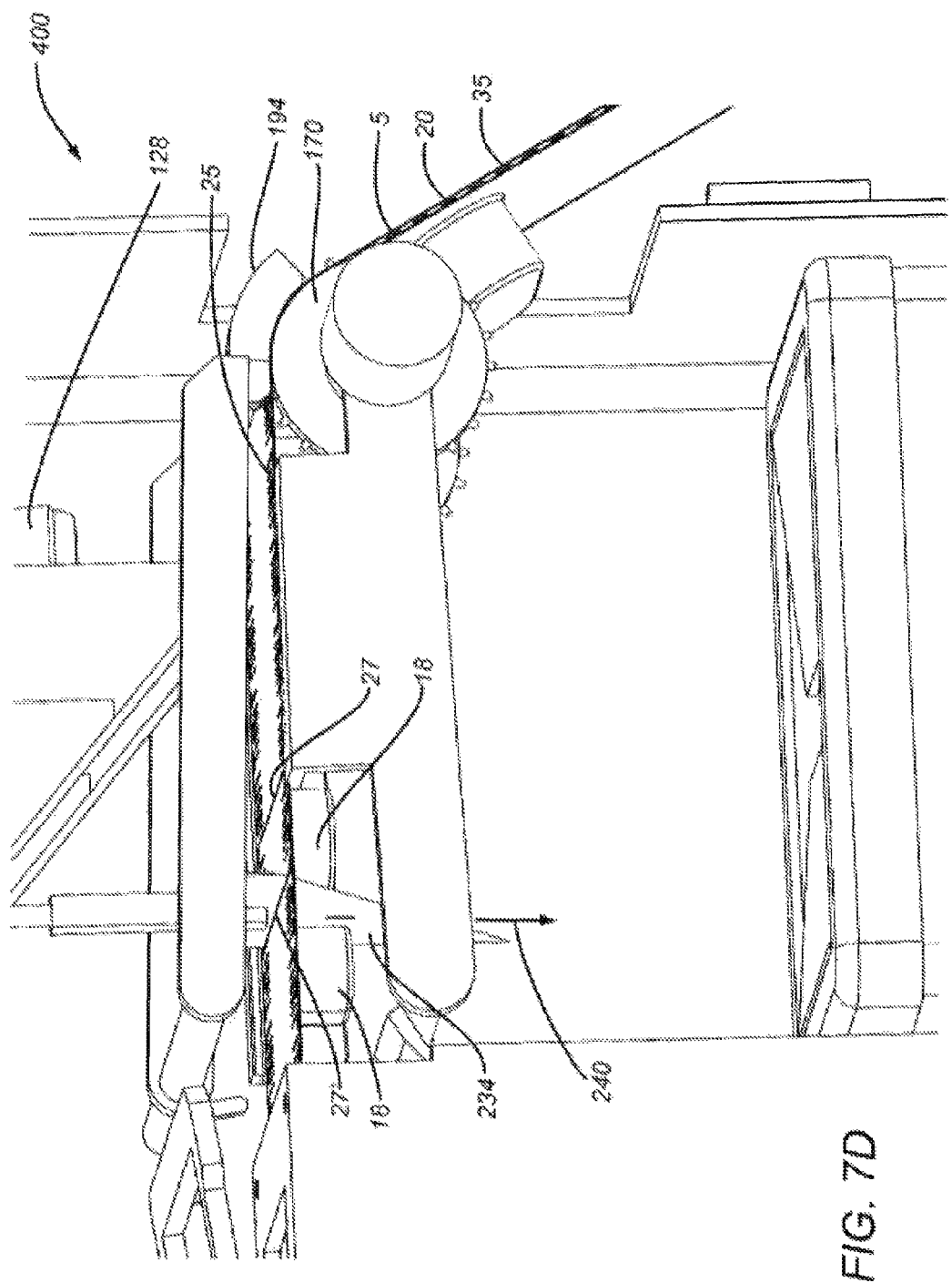
Figure 7E:
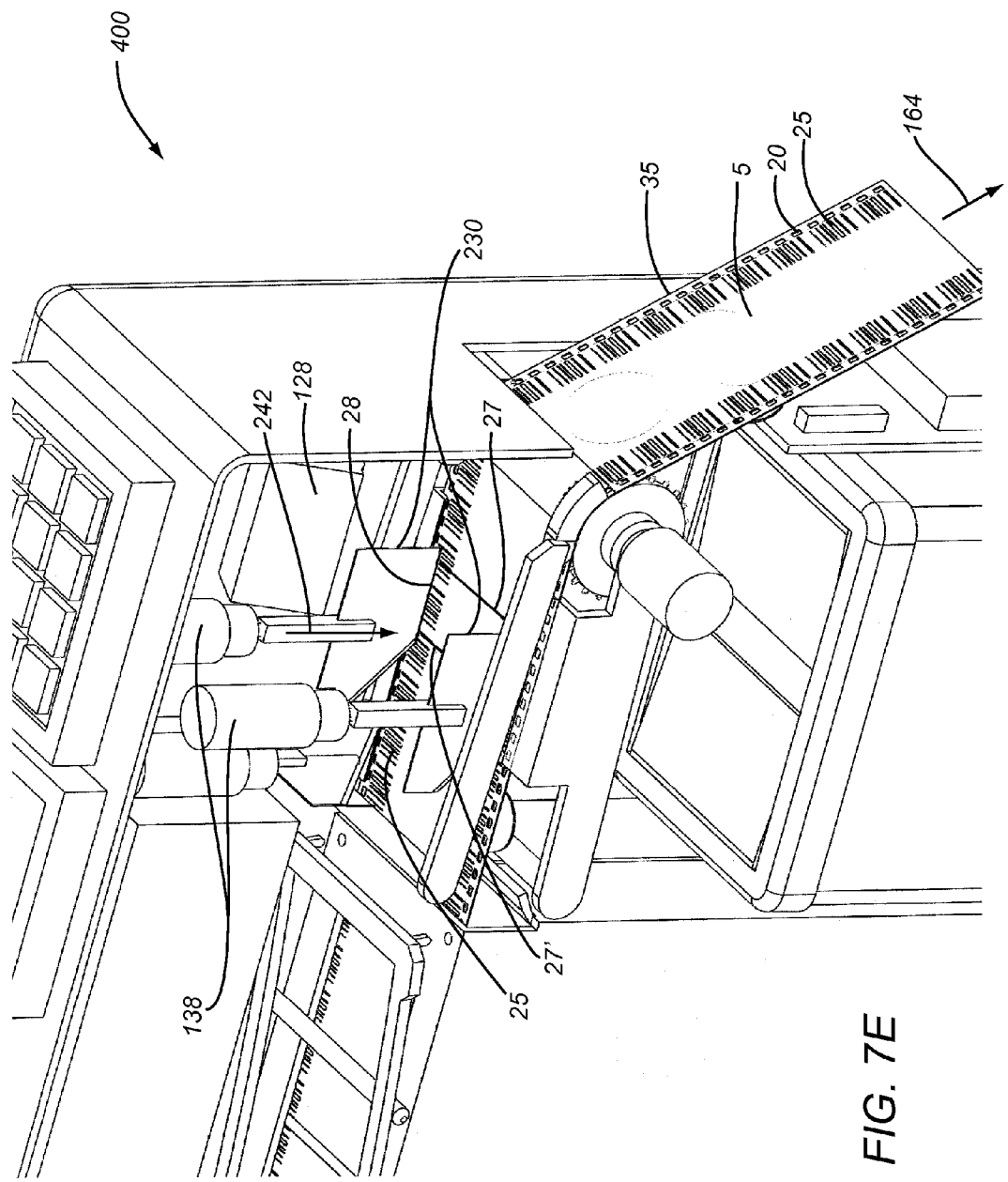

Referring to FIG. 7C, the cross blade 240, attached to actuator 138, advances along cross cut path 240 to create cross cuts 27, 27,' which straddle the blister 18, as shown in FIG. 1C. Further clarification is provided by FIG. 7D, which shows the cross blade 234 cutting through the dose package 5 to create cross cut 27.' Once the cross cuts 27, 27' have been made, longitudinal cuts 28 are made by longitudinal blades 230, e.g., as shown in FIGS. 7E and 7F (a section view through the center of the strip 35). The longitudinal blades 230, attached to actuators 138, are advanced along longitudinal cut path 242 to create longitudinal cuts 28, which straddle the blister 18, e.g., as shown in FIG. 1C.

FIG. 7G shows a section view through the center of the strip 35, illustrating the separation of a blister 18' containing an unwanted item 19' from the dose package 5. The blister 18' falls out of the dose package 5 approximately along drop path 250 into the waste receptacle 154. Once the unwanted item 19' has been thus removed from the dose package 5, the controller 119 may advance the strip 35 to dispense the dose package 5. Various alternatives to blades for cutting unwanted items out of the dose package 5 are contemplated, including Lasers and ultrasonic cutters.

In another embodiment, one or more cutting elements may be provided to create partial cuts (not shown) through the strip 35 around blisters of unwanted items, leaving enough material intact to retain the blister(s). The dispenser 400 may then advance the strip 35 to dispense the dose package 5 without removing the weakened blister. The user may subsequently remove the undesired blister easily by hand. Alternatively, the cuts may be configured to allow the user to peel the cover 10 off of dose package 5, while leaving at least a portion of cover 10 attached to the unwanted blister to retain the undesired item within the blister, thereby not administering the unwanted item.

Figure 8A:
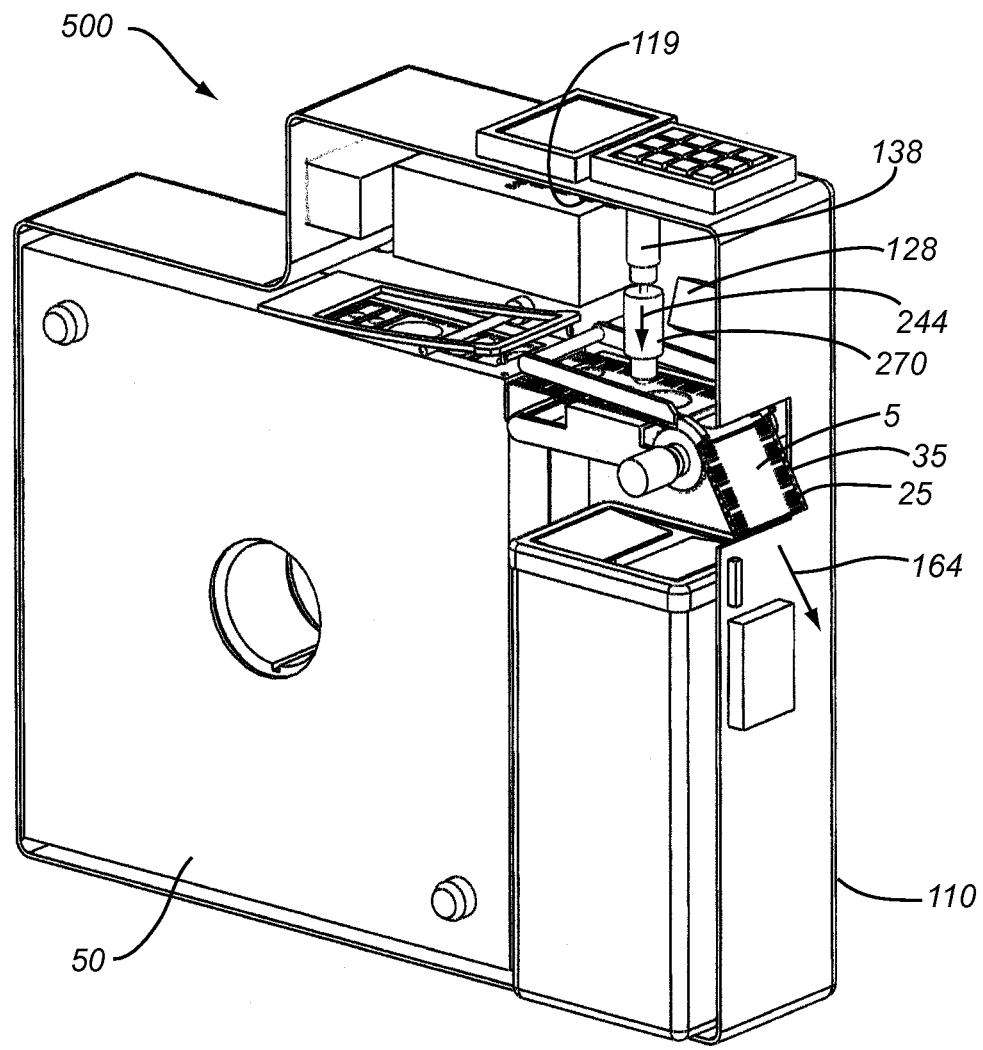
FIGS. 8A and 8B are perspective views of another embodiment of a dispenser with a portion of the outer housing removed to show an internal marking device, showing a method for marking an unwanted blister from a dose package using the marking device before dispensing the dose package from the dispenser.
Figure 8B:
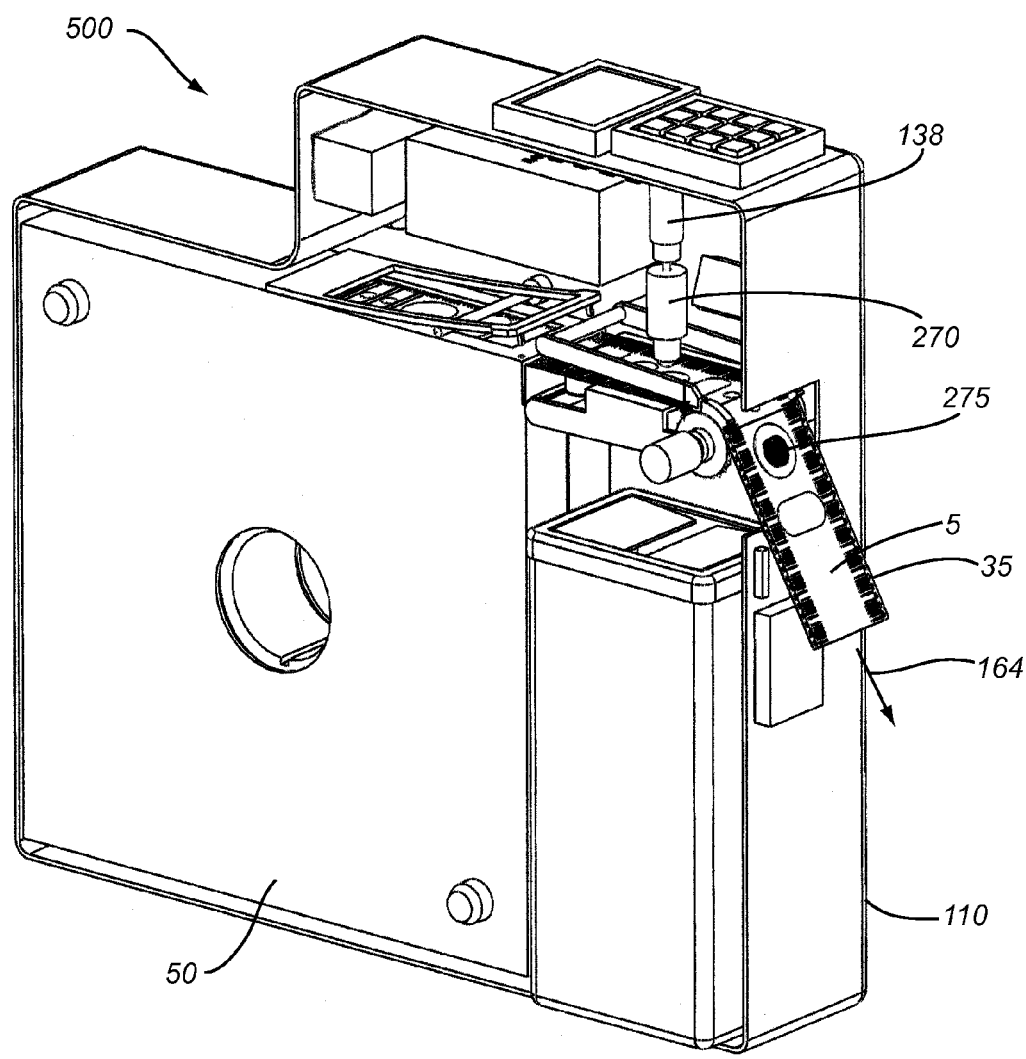

In yet another embodiment, a system and method for marking unwanted items is illustrated in FIGS. 8A and 8B. Dispenser 500, which may be otherwise similar to other embodiments herein, includes a marking device 270, attached to an actuator 138 operated by controller 119. The actuator 138, which actuates the marking device 270, may be solenoid, motorized, electric, pneumatic, or otherwise actuated. As the strip 35 advances along dispense path 164, machine code sensor 128 (for example, a barcode reader) may monitor the machine-readable information 25 on the dose package 5, in order to locate any unwanted items 19 in the dose package 5. Once an unwanted item 19 has been located and positioned, the controller may stop advancement of the strip 35 with unwanted item 19 in the dose package 5 in position under the marking device 270.

The marking device 270 is driven by the actuator 138 approximately along marking path 244 and contacts the dose package 5. As shown in FIG. 8B, the marking device 270 is retracted by the actuator 138, and the strip 35 is advanced along the dispense path 164 to dispense the dose package 5. An indicator feature 275, created by the marking device 270, is located on the dose package 5 to indicate to the user which blister(s) 18 contains unwanted item 19, so the unwanted item(s) 19 may be removed and discarded, rather than administered to the patient.

Figure 9A:
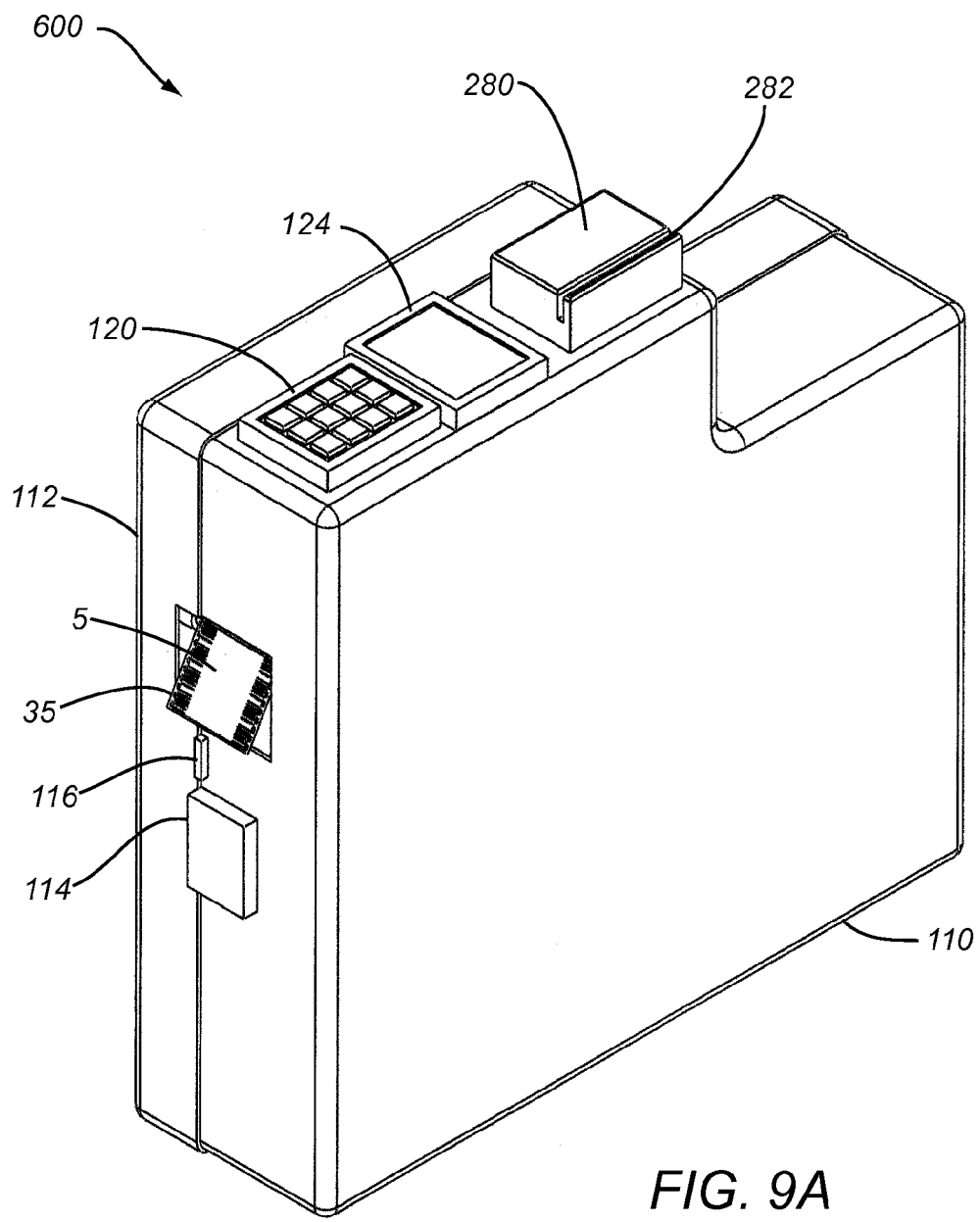
FIGS. 9A and 9B are perspective views of yet another embodiment of a dispenser including an access device for limiting use of the dispenser only to authorized users.

Additional optional features may be desirable in any of the dispensers described herein. For example, FIG. 9A shows a dispenser 600 that includes an access device 280, e.g., used to restrict access to the control functions of the dispenser 600 and/or to identify users who access the packages and medications dispensed by the dispenser 600. Examples of such control functions may be to indicate which items 19 are undesirable (and should be removed prior to dispensing the dose package 5) or to permit a user to remove multiple dose packages 5. In an exemplary embodiment, the access device 280 may be a reader slot 282 to permit magnetic card reading. The access device 280 may also be configured to read other identification devices, such as barcodes or RFID devices, or any other features of identifying the user's identity. Alternatively, a keypad 120 may be used to identify a user and/or enter a security code to permit access to the control functions of the dispenser 600.

Figure 9B:
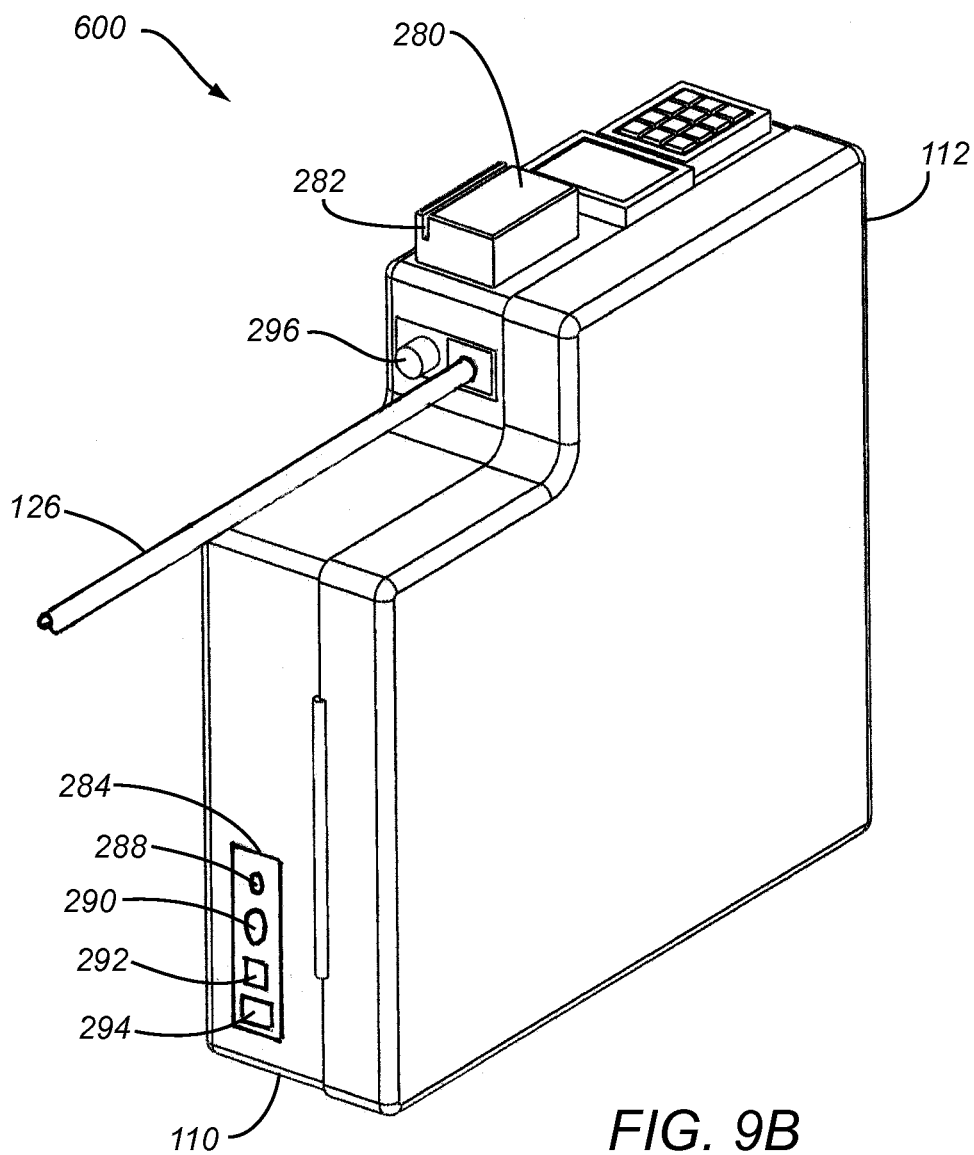

Referring to FIG. 9B, an optional communication panel 284 is shown on the dispenser 600 that may be coupled to one or more communications interfaces (not shown) within the dispenser 600, e.g., coupled to the controller 119 (also not shown). The communication panel 284 may provide a connection point for various communication technologies to the dispenser 600, e.g., for transmitting or receiving data between the controller 119 and/or internal memory of the dispenser 600 and external devices, e.g., remote from the dispenser 600. For example, cables may be attached at CAT5 connector 294 or telephone jack 292. A custom jack 290 may allow attachment of proprietary cables. In addition or alternatively, a wireless connection 288 may permit connection to one or multiple wireless devices remote from the dispenser 600. In addition or alternatively, other communication interfaces are contemplated, for example, cellular telephone transceivers, modems, and the like. In some cases related biometric equipment, such as blood monitoring devices (not shown), may interface with the dispenser 600, as desired.

Figure 10A:
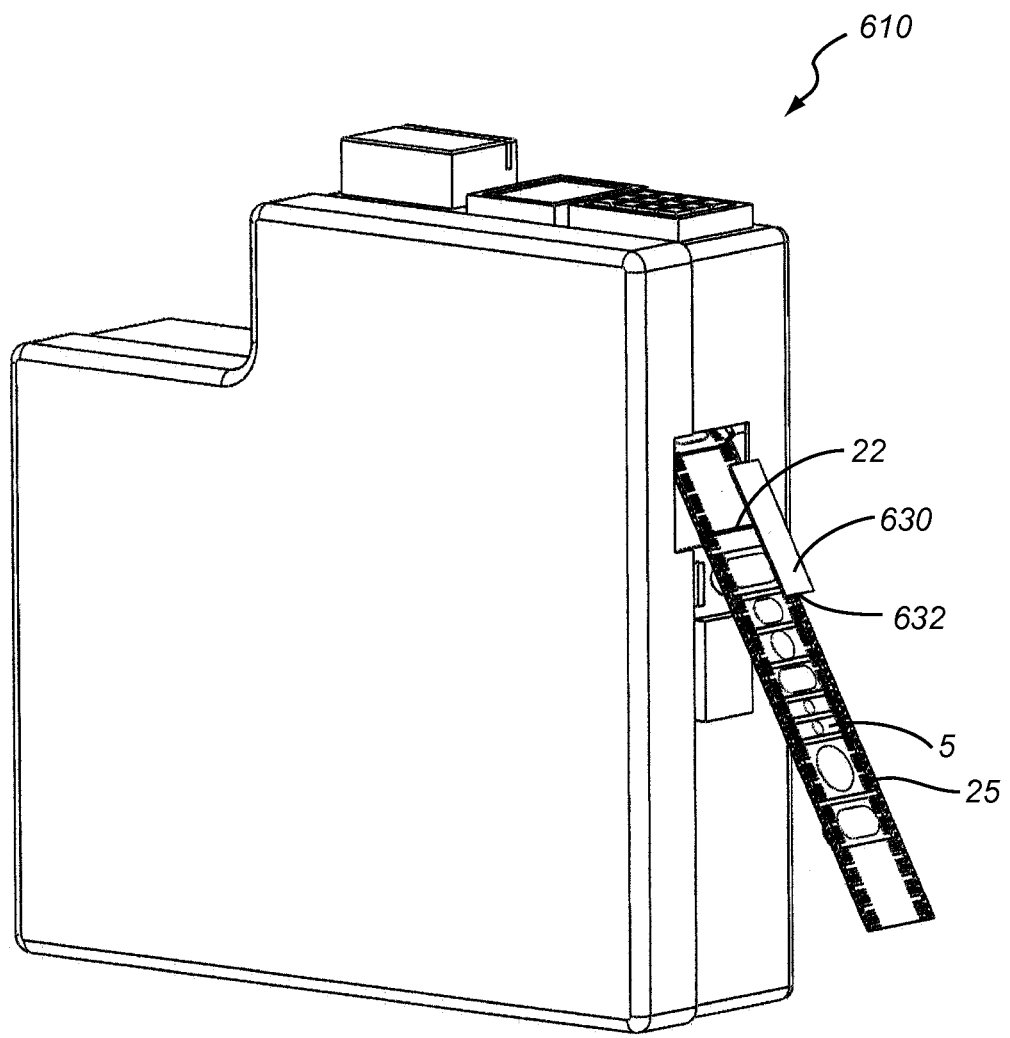
FIGS. 10A and 10B are perspective views of another embodiment of a dispenser including a detach detector that confirms when a presented dose package is removed from the dispenser.
Figure 10B:
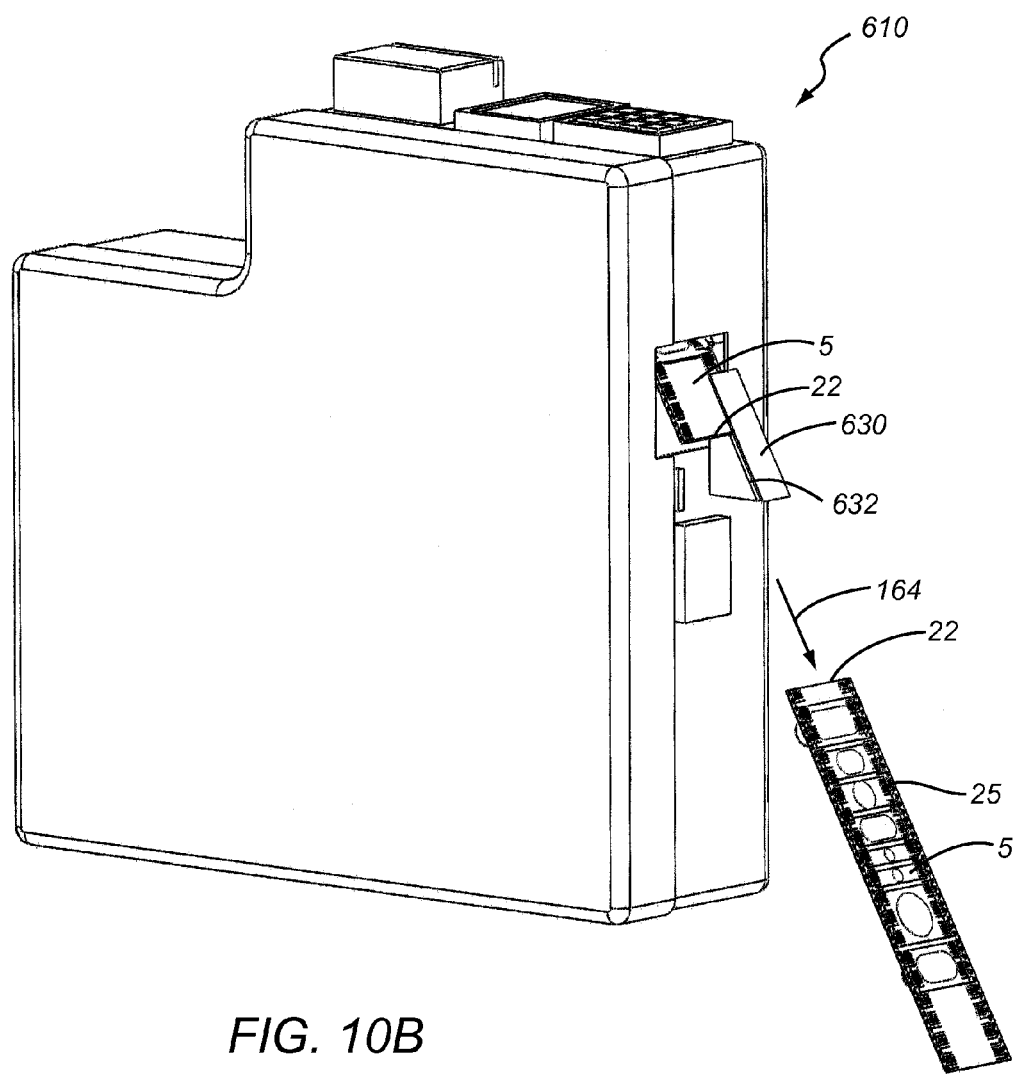

Turning to FIGS. 10A and 10B, in some cases, it may be advantageous to confirm that the user has removed a dose package 5 dispensed from a dispenser. For example, as shown in FIG. 10A, a dispenser 610 has dispensed a dose package 5, which is ready for the user to detach it at weakened region or other connection feature on the trailing end 22. A detach detector 630 is in proximity to the dose package 5, and an optional detach detector slot 632 shrouds a portion of the dose package 5. The detach detector 630 may detect the dispensed dose package 5 using optical, barcode, magnetic, RFID, or other reading technologies. Once the user has detached the dose package 5, e.g., by tearing weakened region or other connection feature across the trailing end 22, the detach detector 630 may sense the absence of the dose package 5.

If the user fails to detach the dose package 5 within a predetermined time, a controller (not shown) may detect that the detach detector 630 has not provided a confirmation signal. Consequently, the controller may activate an indicator (not shown), e.g. to give an audible or visual alarm. In addition or alternatively, the controller may contact an appropriate caregiver (e.g., family, nurse, pharmacist, doctor, service center, etc.), e.g., sending an appropriate communication using any of the communications interfaces described elsewhere herein.

Figure 11A:
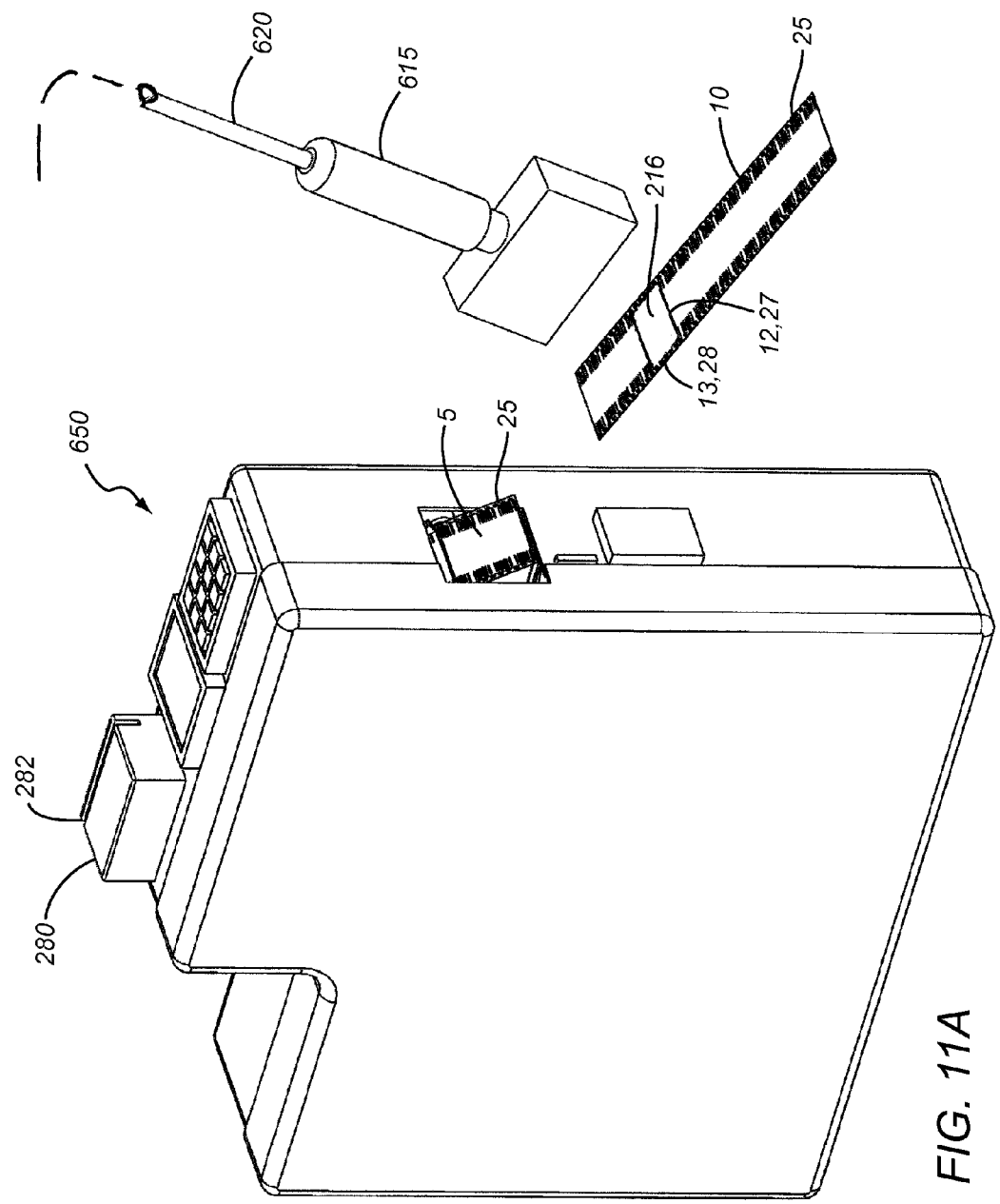
FIGS. 11A and 11B are perspective views of an exemplary embodiment of a system including a dispenser, such as that shown in FIGS. 9A and 9B, and a reader for scanning dose packages removed from the dispenser.
Figure 11B:
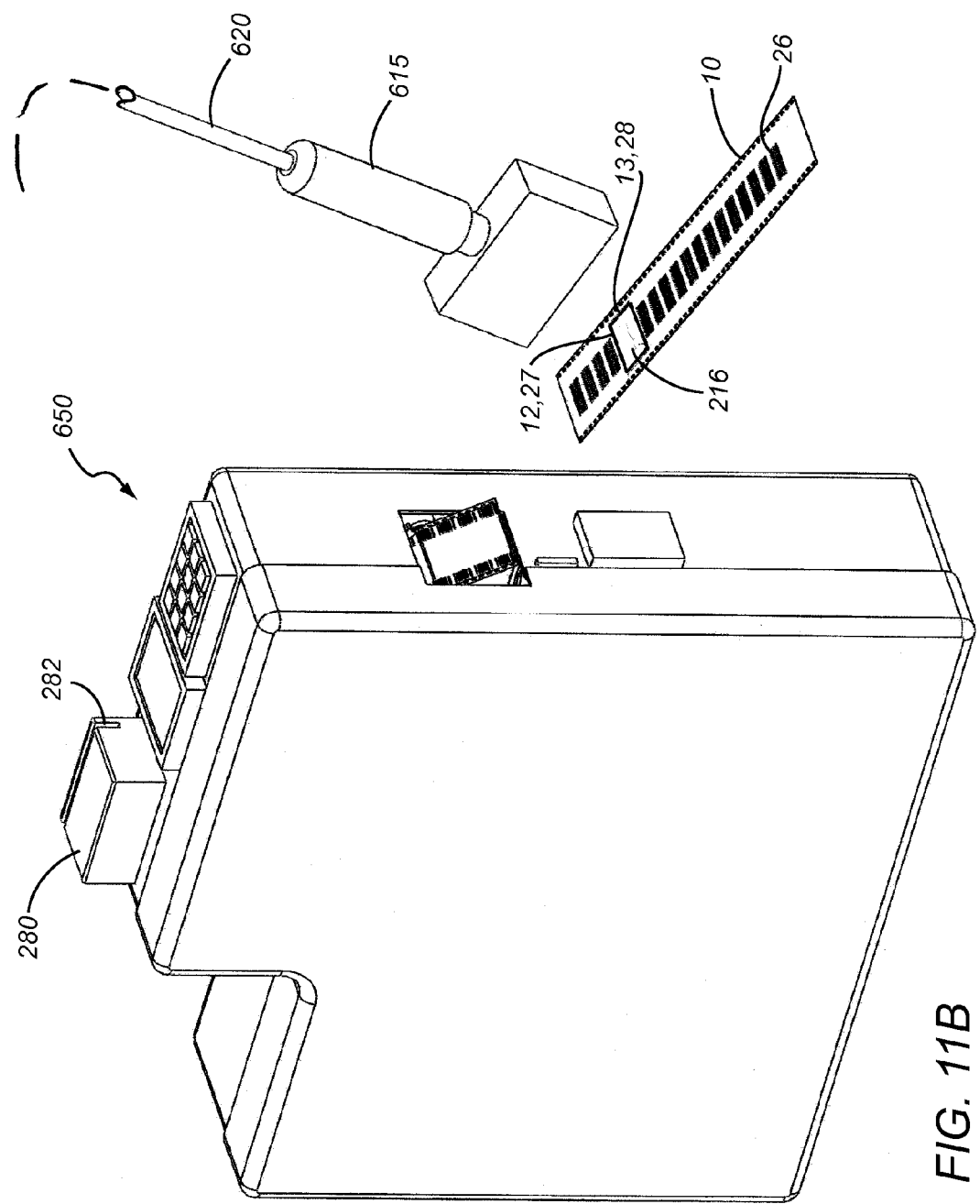

Turning to FIGS. 11A-12B, in another embodiment, it may be advantageous to confirm that the contents of the dose package 5 dispensed from any of the dispensers described herein have been delivered to the patient. For example, FIG. 11A shows a system that includes a dispenser 650 that may be used in conjunction with a reader device for acquiring machine-readable information from a dose package. In one embodiment, an external reader 615 is used to record machine-readable information 25 on the cover 10. For example, the external reader 615 may be a hand-held barcode reader.

Once a caregiver administers the medications in a dispensed dose package to the intended patient, he/she may use the external reader 615 to scan the machine-readable information 25 on the cover 10, which has been peeled off of the base 15 (not shown) to access the medications. An aperture 216 in the cover 10, the result of an unwanted item 19 being removed (as described above), interrupts machine-readable information 25, thereby indicating that the unwanted item 19 was not administered. The external reader 615 may be connected to the dispenser 650, e.g., by a cable 620, or may be a separate device, e.g., communicating with the dispenser 650 and/or other remote devices wirelessly. Alternately, the access device 280 may be used to acquire machine-readable information 25 once the dose has been administered.

In addition, the system may be used to confirm that the cover 10 has been removed from the base 15 (i.e., that the dose package 5 has been opened). For example, as described above, a machine-readable confirmation code 26 may be provided on the inside of the cover 10 (see FIG. 1D). Once the cover 10 has been separated from the base to administer the medications, the confirmation code 26 may be visible, allowing the reader 615 to be used to scan and transmit or record the confirmation code 26, requiring the dose package 5 to be opened for confirmation of the dose being administered, which may increase compliance of dose administration.

Figure 12A:
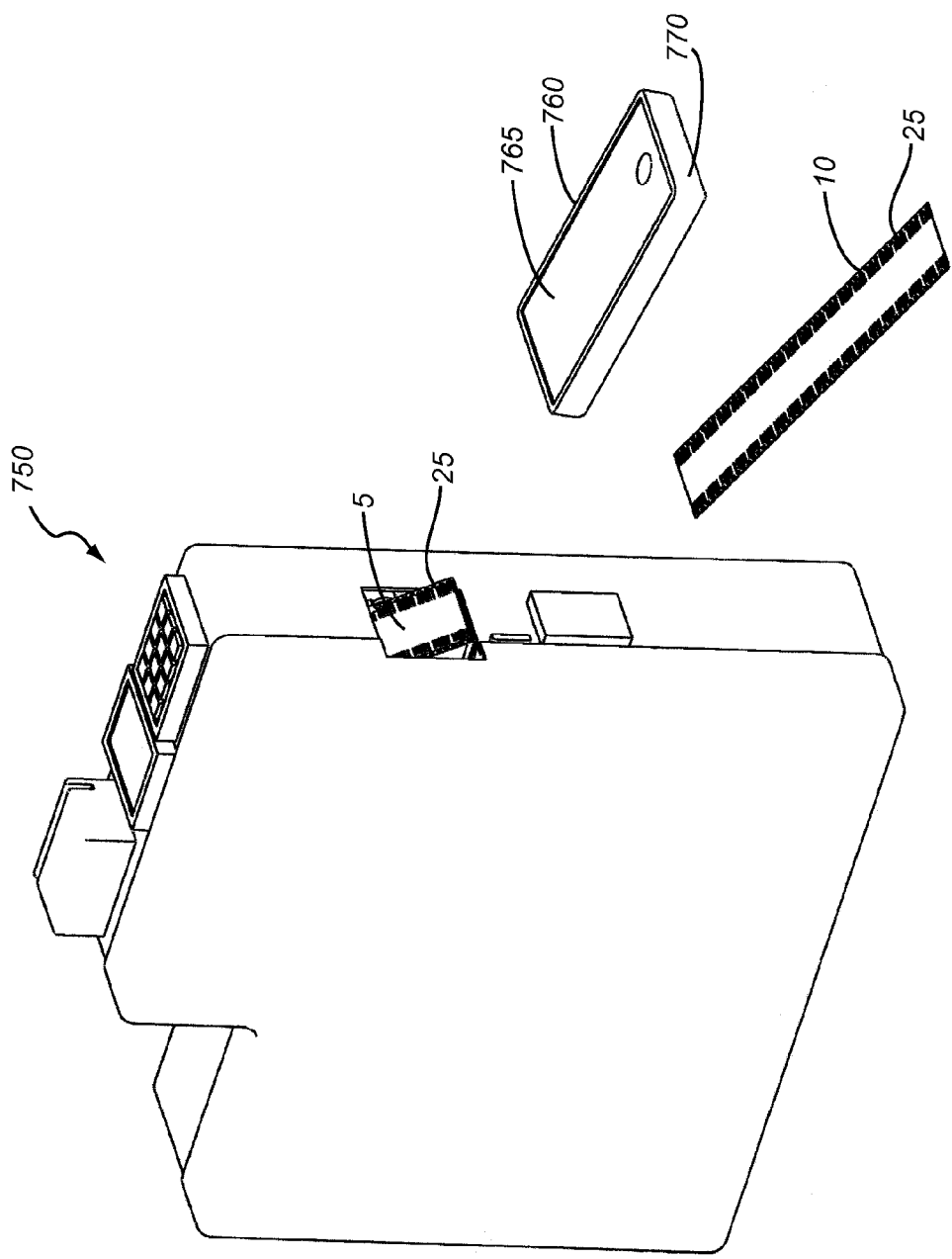
FIGS. 12A and 12B are perspective views of another exemplary embodiment of a system including a dispenser, such as that shown in FIGS. 9A and 9B, and a reader for scanning dose packages removed from the dispenser, such as a cell phone.
Figure 12B:
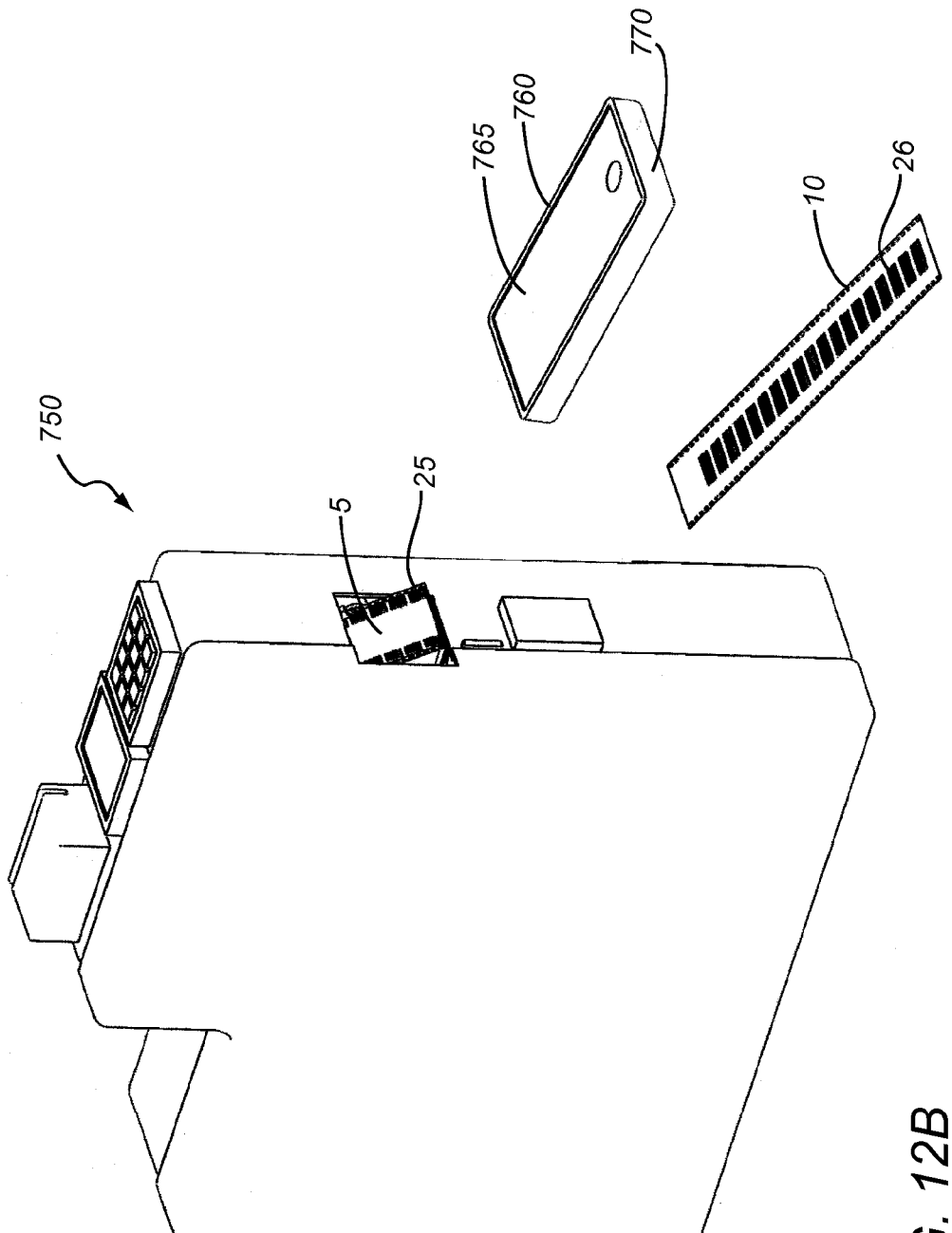

Turning to FIGS. 12A and 12B, another embodiment of a system is shown including a dispenser 750 (including features similar to one or more of the other embodiments herein) capable of dispensing dose packages 5 with machine readable features 25, and a handheld reading device 760. In an exemplary embodiment, the reading device may be a cell phone or other electronic device 760 that includes a software application or other components to "read" machine-readable feature(s) 25 on a cover 10, as shown in FIG. 12A. For example, a camera (not shown) on the cell phone 760 may be used to take a photo or other image of the cover 10, and the application may extract the machine-readable features 25 from the image, and process and/or communicate corresponding information via a communication interface, e.g., existing communication systems, such as Bluetooth protocols, SMS, and the like. Similarly, as shown in FIG. 12B, the application may extract a confirmation code 26 on an inner surface of the cover 10 after opening a dispensed dose package, and transmit the confirmation code to the dispenser 750 or to a remote device, such as an administrative server, as described further elsewhere herein. A confirmation or other information may be presented on a display 765 of the cell phone 760. In this manner, a user provide verification that the medications were administered to the intended patient.

Figure 13A:
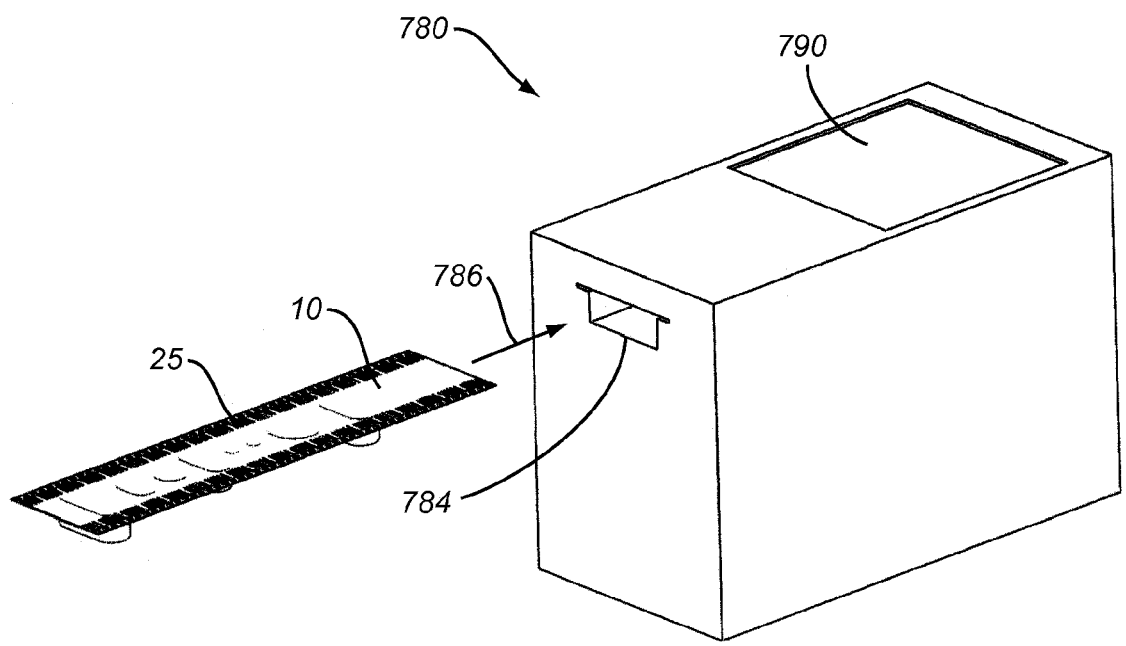
FIGS. 13A and 13B are perspective views of an exemplary embodiment of a reader that may be used to read machine readable data on a dose package dispensed and separated from a dispenser (not shown).
Figure 13B:
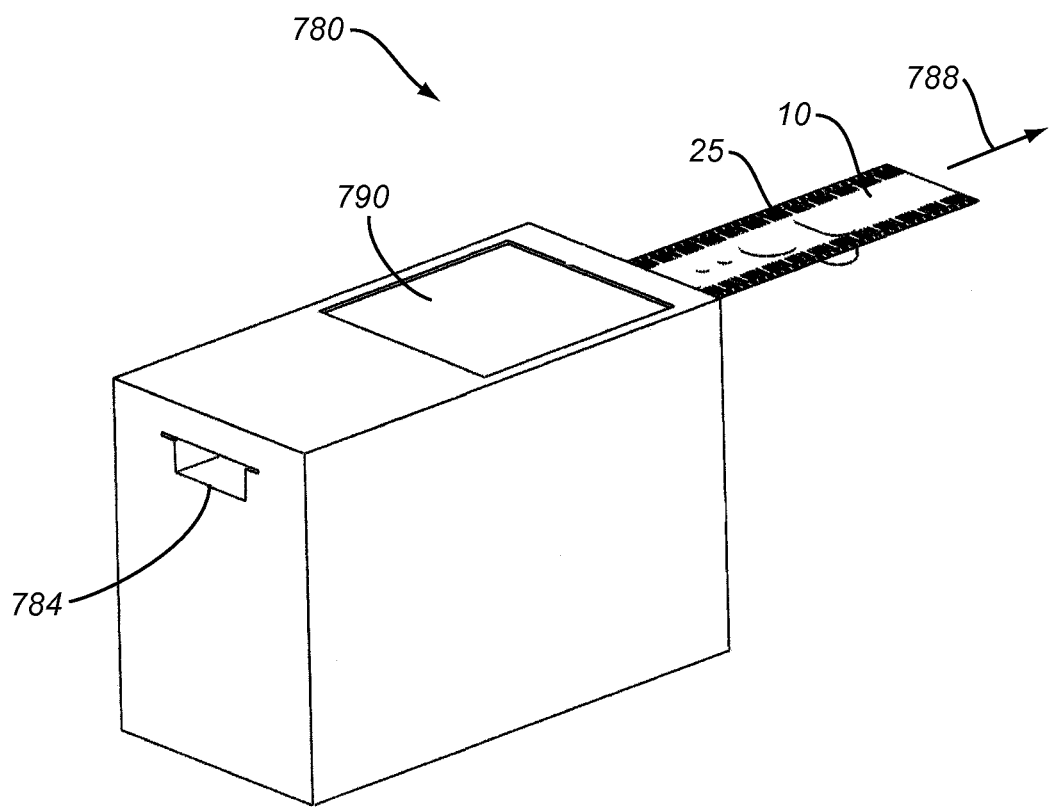

Turning to FIGS. 13A and 13B, in another embodiment, an external dedicated reading device 780 may be used to "read" machine readable feature(s) 25 on cover 10. The cover 10 alone or the entire dose package may be loaded into an access slot 784 of the external dedicated reading device 780 along path 786. The cover 10 and or/package may be automatically or manually driven through the external dedicated reading device 780 for "reading," and may exit along path 788, as shown in FIG. 13B. The user may verify operation, e.g., confirm the identity of the intended patient, the scheduled time and date for administration of the medications in the dose package using a display 790 of the reading device 780.

Figure 14:
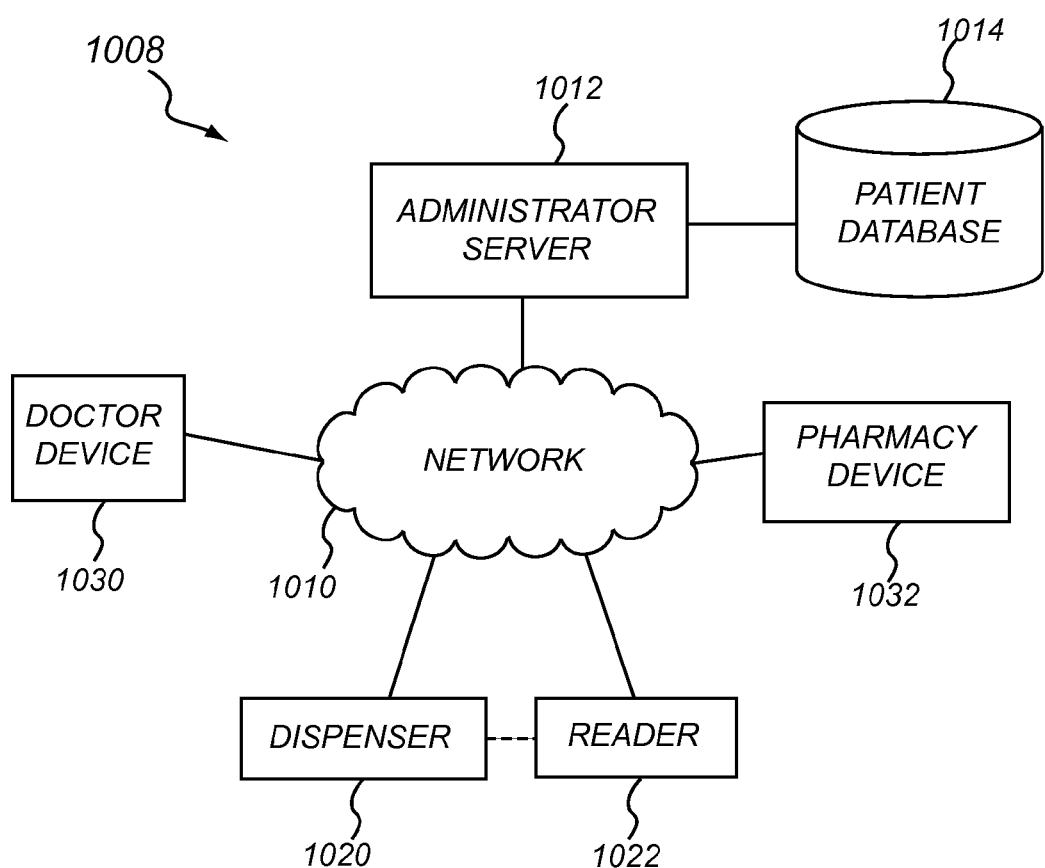
FIG. 14 is a schematic drawing showing a network architecture providing an exemplary embodiment of a system for managing administration of medications to one or more patients.

Turning to FIG. 14, the apparatus, systems, and methods herein may be part of a system 1008 for managing administration of medications to one or more patients, e.g., via a network 1010. In exemplary embodiments, the network 1010 may be a telecommunications network, including a wide area network ("WAN"), a local area network ("LAN"), an intranet, a wireless network, and/or a telephony network. For example, the network 1010 may incorporate several different types of networks including a WAN, a LAN, and/or a wireless network; one such network including multiple different types of networks is the Internet.

As shown, the system 1008 generally includes one or more administrative or other servers 1012 including a patient database 1014, and one or more dispenser devices 1020 (one shown for simplicity), which may be assigned to respective patients (not shown). Each dispenser device 1020 may be any of the embodiments (or combinations of embodiments) described elsewhere herein. It will be appreciated that multiple dispenser devices 1020 may be provided, e.g., assigned to individual patients, who may be at a single physical location or at different physical locations.

Optionally, a reader device 1022 may be provided, e.g., assigned to individual dispenser devices or to physical locations where multiple dispenser devices may be used. As described elsewhere herein, the reader 1022 may be a specialized and/or dedicated device or may be an electronic device, such as a cellular phone, tablet device, laptop computer, desktop computer, and the like, e.g., including an application for performing the various functions of the reader 1022 and/or capable of communicating directly with the dispenser device 1020 and/or with other devices via the network 1010.

The administrative server 1012 may include one or more computer systems including one or more processors, memory and/or storage devices, and communication interfaces (not shown) for communicating via the network 1010, e.g., with the dispenser device 1020 and/or other devices via the network 1010. The administrative server 1012 may include one or more hardware-based components and/or software-based modules for performing the various functions related to the system 1008, as described elsewhere herein.

As shown, the administrative server 1012 may communicate directly with the patient database 1014, e.g., if the administrative server 1012 is at the same physical location as the patient database 1014. Alternatively, the administrative server 1012 and patient database 1014 may be located on one or more different locations from one another, and may communicate via the network 1010. Although only one administrative server 1012 and patient database 1014 are shown, it will be appreciated that one or more administrative servers 1012 may communicate with multiple patient databases 1014 (not shown), e.g., each database responsible for different sets of patients, medical institutions, and the like.

In addition, if desired, one or more doctor electronic devices 1030, pharmacy electronic devices 1032, and the like may also be provided as part of the system. For example, a doctor device 1030 may be used by a patient's physician to update prescriptions or other medication information for the patient. Such information may be communicated by the doctor device 1030 to the administrative server 1012, which may updated the information in the patient database 1014. In addition, the doctor device 1030 and/or pharmacy device 1032 may receive communications from the dispenser device 1020 and/or reader 1022, e.g., confirming administration of medications and/or providing warnings or messages related to compliance, as described elsewhere wherein.

Figure 15:
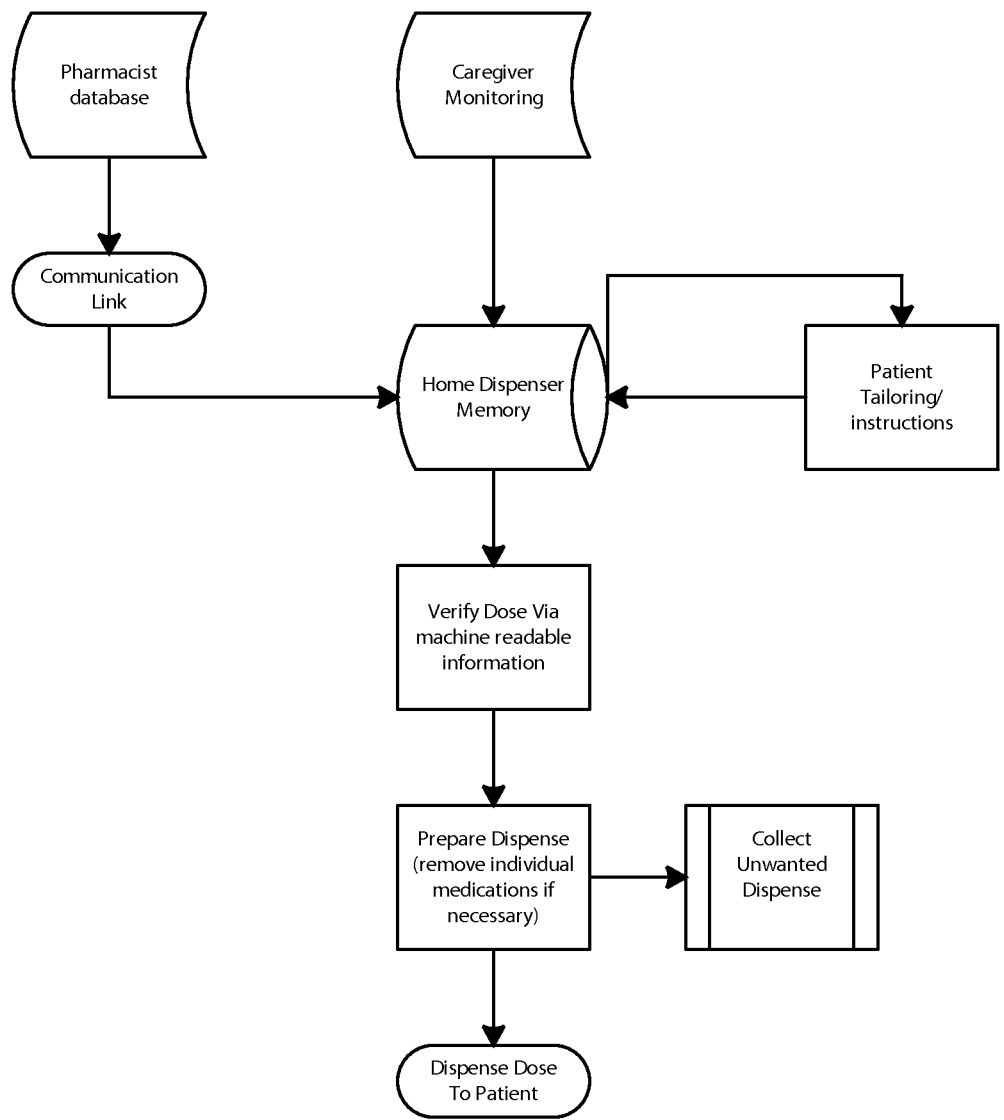
FIG. 15 is a flow chart showing an exemplary system and method for monitoring administration of medications to a patient.

FIGS. 15-19 include flowcharts showing exemplary methods for using a packaging and/or dispensing system, e.g., including a cassette therein with a plurality of single-use packages, such as those described herein. For example, FIG. 15 shows an exemplary initial process overview of how an external caregiver(s) and/or care provider(s) may interact with a dispenser system from a remote location, e.g., via the network 1010 of FIG. 14. A communication link, e.g., including one or more of a telephony network, a wireless network, a computer network, such as the Internet, and the like, provides the ability to remotely monitor and/or control in real time a dispenser, e.g., to dispense items, such as prescription medication, supplements, and the like. The same type of functionality may also be provided via a user interface on the dispenser itself, e.g., a touchpad, keyboard, touch screen, and the like, for use by a caregiver or patient. The dispenser may be capable of performing operations such as dispense verification, dispense modification, and/or collection of unused items from dispensed packages, e.g., in a secure manner. The dispenser may provide information as well as use information from both internal and external sources.

Figure 16:
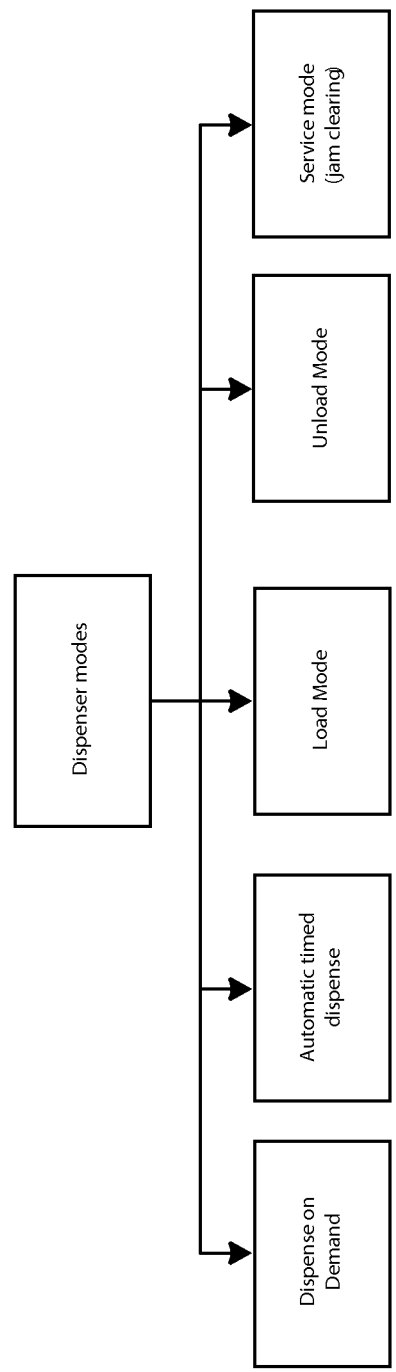
FIG. 16 is a flow chart showing exemplary configurations for operating a dispenser.

FIG. 16 illustrates exemplary modes between which the dispenser may be selectively directed. For example, in a first "on-demand" mode, a patient or caregiver may operate the dispenser to dispense a single or plurality of dosages, e.g., to allow multiple packages to be dispensed for several future scheduled doses, which may facilitate dispensing a plurality of doses for an intended trip rather than taking the entire dispenser. Other possible modes include a "load" mode and/or an unload" mode, which may allow a user to load/reload a cassette or unload a cassette, e.g., to take the entire cassette along for manual dispensing during travel or other activities. Another available mode may be automatic timed dispense, which may facilitate patient compliance, e.g., by automatically dispensing at prescribed time intervals.

If the dispenser is a stand-alone device, the dispenser may include a clock and may dispense dose packages based on times associated with each dose package, e.g., identified on labels of the dose packages. For example, a controller of the dispenser may compare scheduled administration times for successive dose packages and compare the times with the clock. When the scheduled time for the current dose package is reached on the clock, the controller may notify the administrator or may automatically dispense the scheduled dose package.

Alternatively, if the dispenser communicates with a remote server, such as the administrative server 1012 shown in FIG. 14, the dispenser may simply acquire data from the current dose package, e.g., a unique package identified label, and the like, and communicate the data to the administrative server 1012 via the network 1010. The administrative server 1012 may communicate a scheduled administration time for the current dose package, e.g., by comparing the data for the current dose package with data in the patient database. The dispenser may then store the scheduled administration time and dispense the current dose package when the scheduled administration time is reached, e.g., based on the dispenser's clock.

In another alternative, the dispenser may simply wait until instructions are received from the administrative server 1012 to dispense the current dose package. For example, the administrative server 1012 may identify the scheduled administration time and wait until that time is reached on its clock, and then send a command to the dispenser to dispense the current dose package at that time. Other modes may include a service mode, e.g., for clearing jams or other maintenance.

Figure 17:
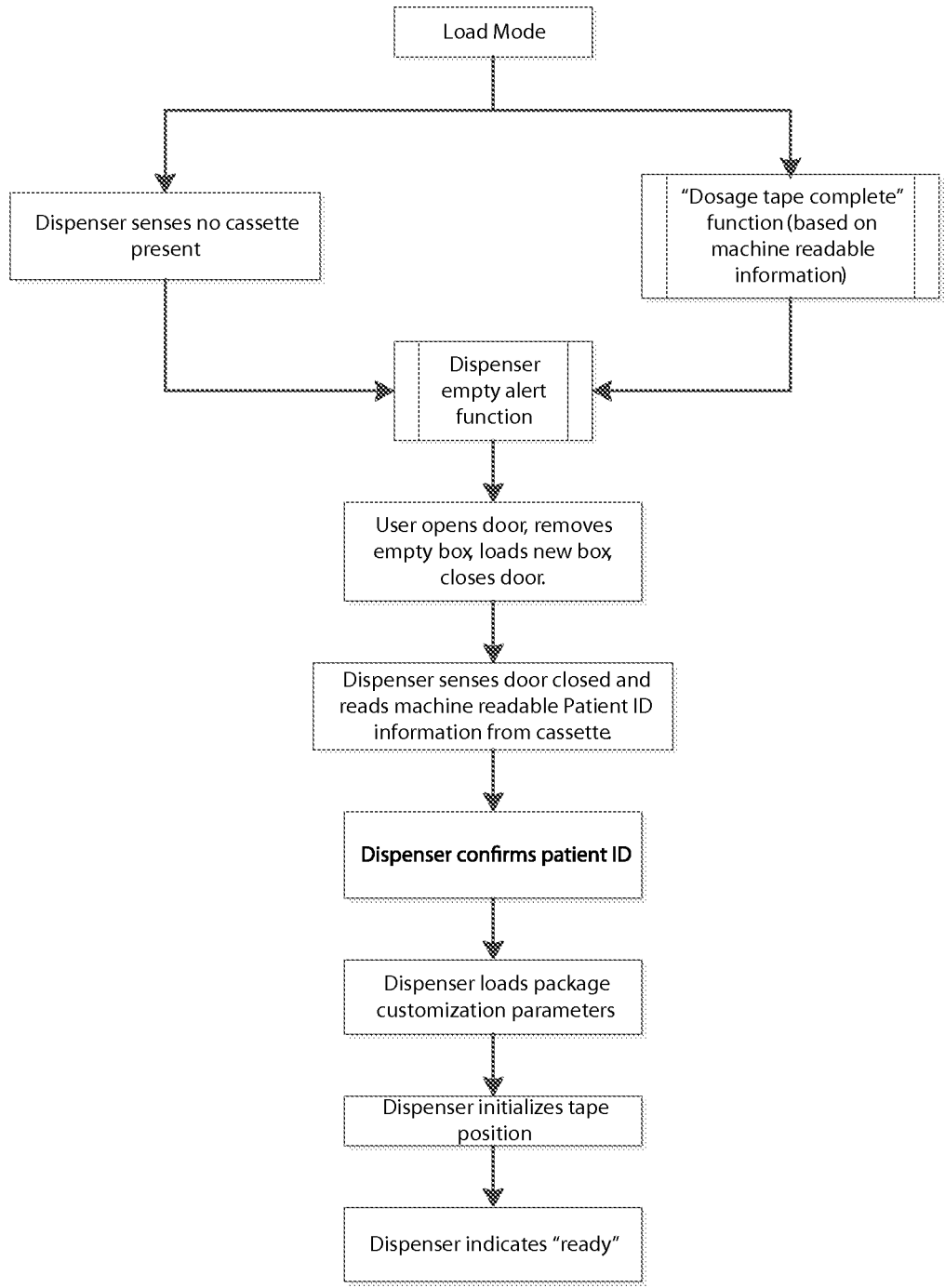
FIG. 17 is a flow chart showing an exemplary method for loading a dispenser with a sequence of dose packages.

FIG. 17 shows an exemplary method for loading a cassette. For example, the dispenser may alert a user when the cassette is empty or missing. The user may then load or reload the cassette when desired and the dispenser may commence an initialization sequence. After one or more desired confirmations have been received, e.g., matching patient and/or user information, the dispenser may be ready for use. Optionally, the dispenser may allow customization of items dispensed from the dispenser, e.g., from both internal and external sources. Dispensers may utilize dispense parameters to determine dispense content.

Figure 18:
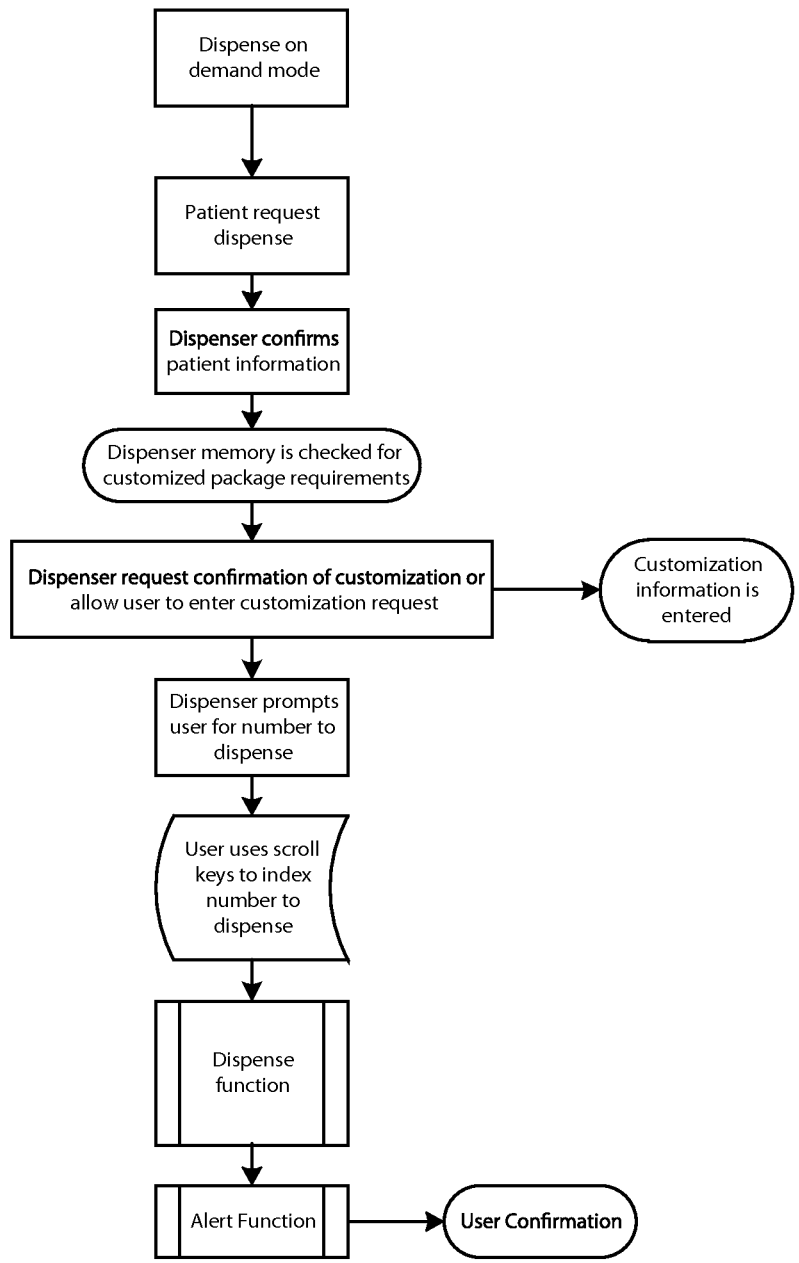
FIG. 18 is a flow chart showing an exemplary method for sequentially dispensing dose packages from a dispenser.

FIG. 18 illustrates an exemplary dispensing on demand sequence. The user may desire this function to generate multiple packages, e.g., to allow for extended time away from the dispenser. The steps shown may allow a user to select the number of dispenses and the content of each dispense. The dispenser may alert the user of the dispense event and/or request user confirmation.

Figure 19:
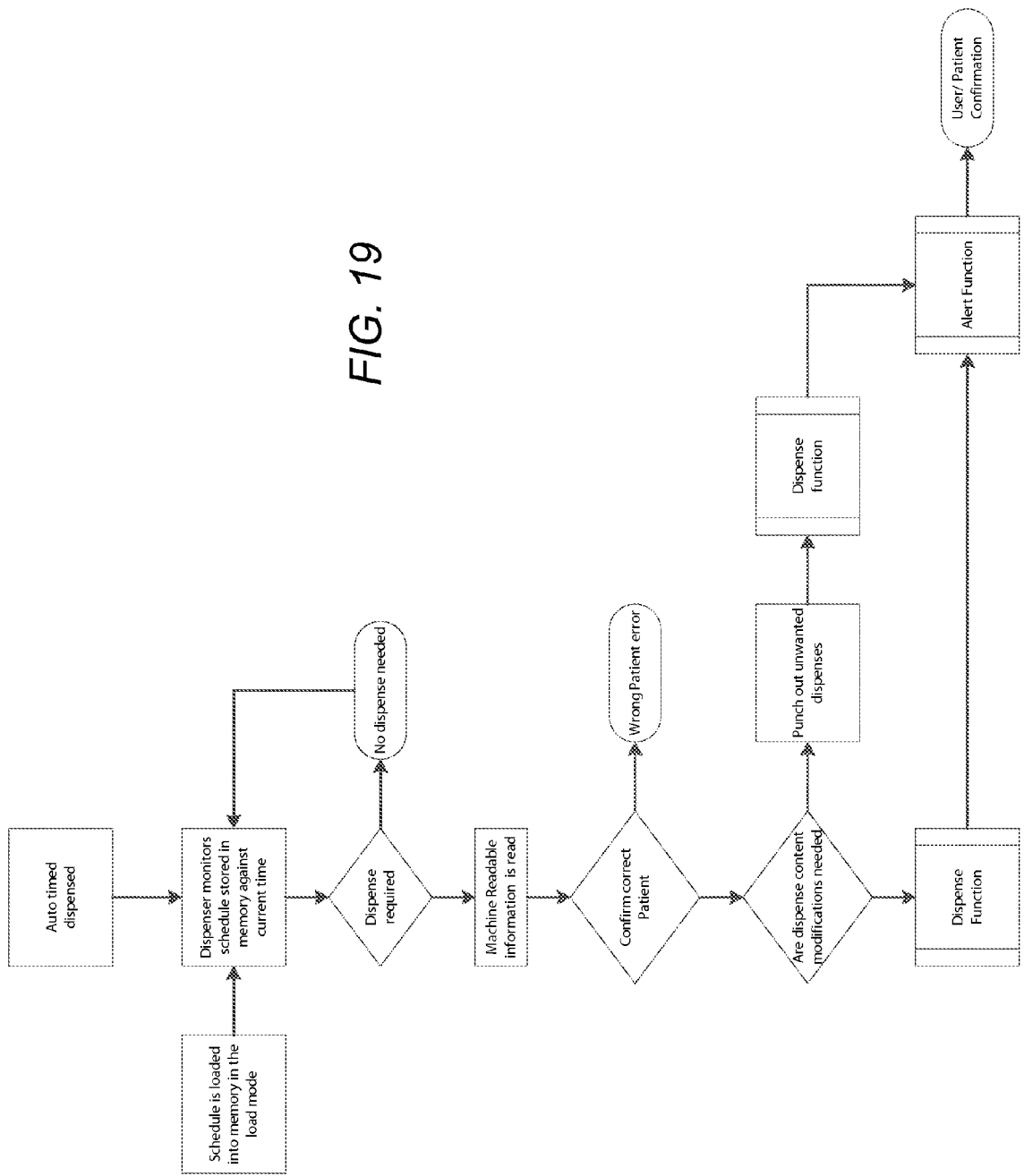
FIG. 19 is a flow chart showing another exemplary method for automatically dispensing dose packages from a dispenser.

FIG. 19 shows an exemplary method for Auto Timed dispense operation. The sequence shown illustrates one such sequence of how the dispenser may utilize machine readable information located on the cassette to dispense in accordance with a prescribed schedule. Included in this sequence are the ability to use a time-based or event-driven stimulus to generate a dispense event. As shown in FIG. 19, the dispenser may provide an alert to the user and/or the user may provide a confirmation.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for administering medications to a patient, comprising:
    a strip comprising a first dispensing end, a second end, and a plurality of blisters aligned in single file generally along a longitudinal axis between the first and second ends and arranged in single-dose packages adjacent one another, at least some of the single-dose packages including a plurality of blisters having different types of medications therein;
    a housing for receiving the strip therein such that the first dispensing end extends from an outlet of the housing;
    a drive mechanism within the housing and coupled to the strip for selectively advancing the strip to dispense single-dose packages sequentially from the outlet;
    a reader adjacent the outlet for reading one or more labels on each of the single-dose packages;
    a controller coupled to the reader and the drive mechanism for analyzing a label on a first single-dose package adjacent the outlet to determine a scheduled administration time for medications in the first single-dose package and for actuating the drive mechanism to dispense the first single-dose package from the outlet at or about the scheduled administration time;
    a communication interface coupled to the controller for accessing a patient database or other information source, the controller analyzing information from the one or more labels using the reader to identify medications in the first single-dose package and acquire an intended patient identity for the identified medications, the controller comparing the medications in the first single-dose package with a schedule of medications for the intended patient stored in the patient database to confirm whether all of the medications are scheduled to be administered to the intended patient; and
    a marker device coupled to the controller, the controller activating the marker device to label one or more blisters of the first single-dose package if medications within the one or more blisters are no longer scheduled to be administered to the intended patient before actuating the drive mechanism to dispense the first single-dose package.

2. An apparatus for administering medications to a patient, comprising:
    a strip comprising a first dispensing end, a second end, and a plurality of blisters aligned in single file generally along a longitudinal axis between the first and second ends and arranged in single-dose packages adjacent one another, at least some of the single-dose packages including a plurality of blisters having different types of medications therein;
    a housing for receiving the strip therein such that the first dispensing end extends from an outlet of the housing;
    a drive mechanism within the housing and coupled to the strip for selectively advancing the strip to dispense single-dose packages sequentially from the outlet;
    a reader adjacent the outlet for reading one or more labels on each of the single-dose packages;
    a controller coupled to the reader and the drive mechanism for analyzing a label on a first single-dose package adjacent the outlet to determine a scheduled administration time for medications in the first single-dose package and for actuating the drive mechanism to dispense the first single-dose package from the outlet at or about the scheduled administration time;
    a communication interface coupled to the controller for accessing a patient database or other information source, the controller analyzing information from the one or more labels using the reader to identify medications in the first single-dose package and acquire an intended patient identity for the identified medications, the controller comparing the medications in the first single-dose package with a schedule of medications for the intended patient stored in the patient database to confirm whether all of the medications are scheduled to be administered to the intended patient; and
    a separation mechanism coupled to the controller, the controller activating the separation mechanism to separate one or more blisters of the first single-dose package from remaining blisters if medications within the one or more blisters are no longer scheduled to be administered to the intended patient before actuating the drive mechanism to dispense the first single-dose package.

3. The apparatus of claim 2, wherein the separation mechanism comprises one or more of punches and wherein the strip comprises weakened regions surrounding each blister such that actuation of one or more punches causes the weakened regions to separate a targeted blister from the first single-dose package.

4. The apparatus of claim 2, wherein the separation mechanism comprises one or more of cutting elements such that activation of one or more cutting elements cuts through the strip to separate a targeted blister from the first single-dose package.

5. The apparatus of claim 2, further comprising a waste receptacle adjacent the separation mechanism for receiving one or more blisters separated from the first single-dose package.

* * * * *